(12) United States Patent
Greshock et al.

(10) Patent No.: US 10,968,210 B2
(45) Date of Patent: *Apr. 6, 2021

(54) DIAMINO-ALKYLAMINO-LINKED ARYLSULFONAMIDE COMPOUNDS WITH SELECTIVE ACTIVITY IN VOLTAGE-GATED SODIUM CHANNELS

(71) Applicants: Merck Sharp & Dohme Corp., Rahway, NJ (US); Thomas J. Greshock, Collegeville, PA (US); James Mulhearn, North Wales, PA (US); Anthony J. Roecker, West Point, PA (US); Tianying Jian, Westfield, NJ (US); Gang Zhou, Bridgewater, NJ (US); Liangqin Guo, Edison, NJ (US); Walter Won, San Carlos, CA (US); Ting Zhang, Princeton Junction, NJ (US); Rajan Anand, Fanwood, NJ (US); John E. Stelmach, Westfield, NJ (US); Deping Wang, Furlong, PA (US); Ronald M. Kim, Summit, NJ (US); Mark E. Layton, Harleysville, PA (US); Christopher S. Burgey, Philadelphia, PA (US); Philippe G. Nantermet, North Wales, PA (US)

(72) Inventors: Thomas J. Greshock, Collegeville, PA (US); James Mulhearn, North Wales, PA (US); Anthony J. Roecker, West Point, PA (US); Tianying Jian, Westfield, NJ (US); Gang Zhou, Bridgewater, NJ (US); Liangqin Guo, Edison, NJ (US); Walter Won, San Carlos, CA (US); Ting Zhang, Princeton Junction, NJ (US); Rajan Anand, Fanwood, NJ (US); John E. Stelmach, Westfield, NJ (US); Deping Wang, Furlong, PA (US); Ronald M. Kim, Summit, NJ (US); Mark E. Layton, Harleysville, PA (US); Christopher S. Burgey, Philadelphia, PA (US); Philippe G. Nantermet, North Wales, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 87 days.

This patent is subject to a terminal disclaimer.

(21) Appl. No.: 16/345,913
(22) PCT Filed: Nov. 13, 2017
(86) PCT No.: PCT/US2017/061221
§ 371 (c)(1),
(2) Date: Apr. 29, 2019

(87) PCT Pub. No.: WO2018/093694
PCT Pub. Date: May 24, 2018

(65) Prior Publication Data
US 2020/0131167 A1 Apr. 30, 2020

Related U.S. Application Data

(60) Provisional application No. 62/423,411, filed on Nov. 17, 2016.

(51) Int. Cl.
C07D 417/12 (2006.01)
C07D 417/14 (2006.01)
(Continued)

(52) U.S. Cl.
CPC ......... C07D 417/12 (2013.01); C07D 277/52 (2013.01); C07D 401/12 (2013.01);
(Continued)

(58) Field of Classification Search
CPC .. C07D 417/12; C07D 417/14; C07D 277/52; C07D 471/04; C07D 487/10; C07D 401/12
See application file for complete search history.

(56) References Cited

U.S. PATENT DOCUMENTS 10,519,147 B2 * 12/2019 Greshock ............. C07D 417/12
2009/0131440 A1 5/2009 Stamos
(Continued)

FOREIGN PATENT DOCUMENTS

WO 2015077905 A1 6/2015
WO 2017/106409 A1 6/2017

OTHER PUBLICATIONS

Aoldin et al., Nomenclature of Voltage-Gated Sodium Channels, Neuron, 2000, 365-368, 28.
(Continued)

Primary Examiner — Laura L Stockton
(74) Attorney, Agent, or Firm — Sylvia A. Ayler; Catherine D. Fitch

(57) ABSTRACT

Disclosed are compounds of Formula A, or a salt thereof: Formula (A), wherein: Het, Q and $R^{1A}$ to $R^{4A}$ are defined herein, which compounds have properties for blocking $Na_v$ 1.7 ion channels found in peripheral and sympathetic neurons. Also described are pharmaceutical formulations comprising the compounds of Formula A or their salts, and methods of treating cough, itch, acute pain and neuropathic pain disorders using the same.

(A)

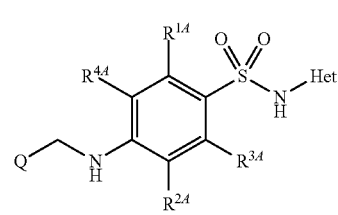

19 Claims, No Drawings

(51) Int. Cl.
  *C07D 277/52* (2006.01)
  *C07D 471/04* (2006.01)
  *C07D 487/10* (2006.01)
  *C07D 401/12* (2006.01)
  *C07D 471/08* (2006.01)
  *C07D 471/10* (2006.01)
  *C07D 487/04* (2006.01)
  *C07D 487/08* (2006.01)

(52) U.S. Cl.
  CPC ......... *C07D 417/14* (2013.01); *C07D 471/04* (2013.01); *C07D 471/08* (2013.01); *C07D 471/10* (2013.01); *C07D 487/04* (2013.01); *C07D 487/08* (2013.01); *C07D 487/10* (2013.01)

(56) References Cited

U.S. PATENT DOCUMENTS

| | | |
|---|---|---|
| 2012/0149742 A1 | 6/2012 | Hilgraf et al. |
| 2013/0035310 A1 | 2/2013 | Martinborough et al. |
| 2017/0174674 A1 | 6/2017 | Greshock et al. |

OTHER PUBLICATIONS

Baker et al., Involvement of Na + Channels in Pain Pathways, Trends in Pharmacological Sciences, 2001, 27-31, 22, No. 1.
Benyamin et al., Opioid Complications and Side Effects, Pain Physician, 2008, 105-120, 11.
Berge, S.M., et al.,, "Pharmaceutical Salts", J. Pharm. Sci, 1977, pp. 1-19, vol. 66, No. 1.
Bingham, A.L., et al.,, "Over One Hundred Solvates of sulfathiazole", Chem. Commun., 2001, pp. 603-604.
Caira, M.R., et al.,, "Preparation and Crystal Characterization of a Polymorph,a Monohydrate, and an Ethyl Acetate Solvate of the Antifungal Fluconazole", J. Pharmaceutical Sci., 2004, pp. 601-611, vol. 93, No. 3.
Carter et al., Advances in the Management of Neuropathic Pain, Physical Medicine and Rehabilitation Clinics of North America, 2001, 447-459, 12(2).
Chong et al., Comparison of Lidocaine and Bronchodilator Inhalation Treatments for Cough Suppression in Patients with Chronic Obstructive Pulmonary Disease, Emerg Med J., 2005, 429-432, 6.
Clare et al., Voltage Gated Sodium Channels as Therapeutic Targets, Therapeutic Focus, 2000, 506-520, 5.
Cox et al., Toxicity of Local Anaesthetics, Best Practices & Research Clinicial Anaesthesiology, 2003, 111-136, 17, No. 1.
Devigili et al., Paroxysmal Itch Caused by Gain of Function Nav1/7 Mutation, Pain, 2014, 1702-1707, 155.
Faber et al., Gain of Function Nav1.8 Mutations in Painful Neuropathy, PNAS, 2012, 19444-19449, 109, 47.
Fischer et al., Familial Pain Syndromes from Mutations of the Nav 1.7 Sodium Channel, Ann. N.Y. Acad. Sci., 2010, 196-207, 1184.
Flaxman et al., Years Lived with Disability (YLDs) for 1160 Sequelae of 289 Diseases and Injuries 1990-2010: A Systematic Analysis for the Global Burden of Disease Study 2010, Lancet, 2012, 2163-2196, 380.
Goldberg et al., Loss of Function Mutations in the Nav1.7 Gene Underlie Congenital Indifference to Pain in Multiple Human Populations, Clin Genet, 2007, 311-319, 71.

Goldin, Diveristy of Mammalian Voltage-Gated Sodium Channels, Ann NY Acad Sci., 1999, 38-50, 30, 868.
Gould, Salt selection for basic drugs, International J. of Pharmaceutics, 1986, 201-217, 33.
Hansson et al., Effects of Inhaled Lignocaine and Adrenaline on Capsaicin Induced Cough in Humans, Thorax, 1994, 1166-168, 49.
Ikoma et al., The Neurobiology of Itch, Nature Reviews, 2006, 535-547, 7.
Irwin et al., The Diagnosis and Treatment of Cough, New England J. of Medicine, 2000, 1715-1721, 343 (23).
Klinger et al., Sea-Anemone Toxin ATX-II Elicits A-Fiber-Dependent Pain and Enhances Resurgent and Persistent Sodium Currents in large Sensory Neurons, Molecular Pain, 2012, 1-17, 8:69.
Lee et al., A Monoclonal Antibody that Targets a Nav1.7 Channel Voltage Sensor for Pain and Itch Relief, Cell, 2014, 1-12, 157.
Loey et al., Itching Following Burns: Epidemiology and Predictors, British J. Dermatology, 2008, 95-100, 158.
McMahon et al., Itching for an Explanation, Trends Neuroscience, 1992, 497-501, 15.
Meissner et al., Improving the Management of Post Operative Acute Pain: Priorities for Change, Current Medical Research & Opinion, 2015, 2131-2143, 31 No. 11.
Morice et al., Opiate Therapy in Chronic Cough, Am J. Respir Crit Care Med., 2007, 312-315, 175.
Muroi et al., Selective Inhibition of Vagal Afferent Nerve Pathways Regulating Cough Using Nav 1.7 shRNA Silencing in Guinea Pig Nodose Ganglia, Am. J. Physiol Regul Interg Comp Physiol, 2013, R1017-R1023, 301.
Muroi et al., Targeting Voltage Gated Sodium Channels Nav1.7 Nav 1.8, and Nav 1.9 for Treatment of Pathological Cough, Lung, 2014, 15-20, 192.
Nasra et al., Modulation of Sensory Nerve Function and the Cough Reflex: Understanding Disease Pathogenesis, Pharmacology & Therapeutics, 2009, 354-375, 124.
Niassar et al., Nociceptor Specific Gene Deletion REveals a Major Role for Nav1.7 (PN1) in Acute and Inflammatory Pain, Proc. Nat. Acad. Sci, 2004, 12706-12711, 101 (34).
Rook et al., Biology of Cardiac Sodium Channel Nav1.5 Expression, Cardiovascular Research, 2012, 12-23, 93.
Schmelz et al., Specific C-Receptors for Itch in Human Skin, J. of Neuroscience, 1997, 8003-8008, 17(20).
Smith et al., Effect of Codeine on Objective Measurement of Cough in Chronic Obstructive Pulmonary Disease, J. of Allergy and Clinical, 2006, 831-835, 117.
Takahama et al., Central and Peripheral Mechanisms of Narcotic Antitussives: Codeine Sensitive and Resistant Coughs, Cough, 2007, 1-8, 3:8.
Van Tonder, E.C., et al.,, "Preparation and Physicochemical Characterization of 5 Niclosamide Solvates and 1 Hemisolvate", AAPS Pharm Sci Tech, 2004, pp. 1-10, vol. 5, No., US.
Waxman et al., Na, 1.7-Related Small Fiber Neuropathy, Neurology, 2012, 1635-1643, 78 (21).
Wood et al., Voltage-Gated Sodium Channels and Pain Pathways, J. Neurobiol., 2004, 55-71, 61.
Yu et al., Overview of the Voltage-Gated Sodium Channel Family, Genome Biology, 2003, 207, 4.
Zhang et al., Gain of Function Mutations in SCN11A Cause Familial Episodic Pain, American J. of Human Genetics,- 2013, 957-966, 93 (5).

* cited by examiner

DIAMINO-ALKYLAMINO-LINKED ARYLSULFONAMIDE COMPOUNDS WITH SELECTIVE ACTIVITY IN VOLTAGE-GATED SODIUM CHANNELS

CROSS REFERENCE TO RELATED APPLICATIONS

This application is the National Stage of International Application No. PCT/US17/061221, filed Nov. 13, 2017 which claims priority to U.S. Ser. No. 62/423,411 filed Nov. 17, 2016.

BACKGROUND

Voltage-gated sodium channels play a central role in initiating and propagating action potentials in electrically excitable cells such as neurons and muscle, see for example Yu and Catterall, Genome Biology 4:207 (2003) and references therein. Voltage-gated sodium channels are multimeric complexes characterized by an Alpha-subunit which encompasses an ion-conducting aqueous pore, and is the site of the essential features of the channel, and at least one Beta-subunit that modifies the kinetics and voltage-dependence of the channel gating. These structures are ubiquitous in the central and peripheral nervous system where they play a central role in the initiation and propagation of action potentials, and also in skeletal and cardiac muscle where the action potential triggers cellular contraction. (see Goldin, Ann NY Acad Sci. 30; 868:38-50 (1999)).

Sensory neurons are also responsible for conveying information from the periphery e.g. skin, muscle and joints to the central nervous system (spinal cord). Sodium channels are integral to this process as sodium channel activity is required for initiation and propagation of action potentials triggered by noxious stimuli (thermal, mechanical and chemical) activating peripheral nocipceptors.

Nine different Alpha-subunits have been identified and characterized in mammalian voltage-gated sodium channels. These structures are designated $Na_v$ 1.X sodium channels (X=1 to 9) in accordance with currently accepted nomenclature practice, designating their ion selectivity (Na), the physiological regulator ('v', potential, i.e. voltage), and the gene subfamily encoding them (1.), with the number designator X (1 to 9) being assigned for the alpha subunit present in the structure (see Aoldin et al., Neuron, 28:365-368 (2000)). $Na_v$1.7 voltage-gated sodium ion channels (herein designated "$Na_v$ 1.7 channels" in some instances for convenience) are expressed primarily in sensory and sympathetic neurons, are believed to play a role in various maladies, for example, nociception, cough, and itch, and in particular have a central role in inflammatory pain perception, (see Wood et al. J. Neurobiol. 61: pp55-71 (2004), Nassar et al., *Proc. Nat. Acad. Sci.* 101(34): pp12706-12711 (2004), Klinger et. al., Molecular Pain, 8:69 (2012), see Devigili et. al., Pain, 155(9); pp 1702-7 (2014), Lee et. al., Cell, 157:1-12 (2014), Muroi et. al., Lung, 192:15-20 (2014), Muroi et. al., Am J Physiol Regul Integr Comp Physiol 304:R1017-R1023 (2013)).

Loss of function mutations in $Na_v$1.7 lead to Cogenital Insensitivity to Pain (CIP), where patients exhibit a lack of pain sensation for a variety of noxious stimuli (Goldberg et al., Clinical Genetics, 71(4): 311-319 (2007)). Gain of function mutations in $Na_v$ 1.7, $Na_v$ 1.8, and $Na_v$ 1.9 manifest in a variety of pain syndromes where patients experience pain without an external stimulus (Fischer and Waxman, Annals of the New York Academy of Sciences, 1184:196-207 (2010), Faber et al., PNAS 109(47): 19444-19449) (2012), Zhang et al., American Journal of Human Genetics, 93(5):957-966 (2013)).

Accordingly, it is believed that identification and administration of agents which interact to block $Na_v$ 1.7 voltage-gated sodium ion channels represents a rational approach which may provide treatment or therapy for disorders involving $Na_v$ 1.7 receptors, for example, but not limited to, acute pain, preoperative pain, perioperative pain, post-operative pain, neuropathic pain, cough, or itch disorders, as well as those stemming specifically from dysfunction of $Na_v$ 1.7 voltage-gated sodium ion channels, see Clare et al., Drug Discovery Today, 5: pp506-520 (2000)).

It has been shown in human patients as well as in animal models of neuropathic pain that damage to primary afferent sensory neurons can lead to neuroma formation and spontaneous activity, as well as evoked activity in response to normally innocuous stimuli. [Carter, G. T. and Galer, B. S., Advances in the Management of Neuropathic Pain, Physical Medicine and Rehabilitation Clinics of North America, 2001, 12(2): pp 447 to 459]. Injuries of the peripheral nervous system often result in neuropathic pain persisting long after an initial injury resolves. Examples of neuropathic pain include, for example, post herpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias. The ectopic activity of normally silent sensory neurons is thought to contribute to the generation and maintenance of neuropathic pain, which is generally assumed to be associated with an increase in sodium channel activity in the injured nerve. [Baker, M. D. and Wood, J. N., Involvement of Na Channels in Pain Pathways, TRENDS is Pharmacological Sciences, 2001, 22(1): pp27 to 31].

Nociception is essential for survival and often serves a protective function. However, the pain associated with surgical procedures and current therapies to relieve that pain, can delay recovery after surgery and increase the length of hospital stays. As many as 80% of surgical patients experience post-operative pain, which arises as a result of tissue damage, including damage to peripheral nerves and subsequent inflammation). Furthermore, 10-50% of surgical patients will develop chronic pain after surgery often because the nerve damage results in lasting neuropathic pain once the wound has healed (Meissner et al., Current Medical Research and Opinion, 31(11):2131-2143 (2015)).

Cough is one of the most prevalent symptoms for which patients seek the attention of their primary care physicians; chronic cough for example is estimated to affect approximately 40% of the population. The fundamental mechanisms of the cough reflex are complex and involve an array of events initiated by the activation of airway sensory nerves that physically results in a forced expiration of the airways. This protective reflex is necessary to remove foreign material and secretions from the airways, however, chronic, non-protective cough results in a dramatic negative impact on quality of life (see Nasra et. al., Pharmacology & Therapeutics, 124(3):354-375 (2009)).

Cough symptoms can arise from the common cold, allergic and vasomotor rhinitis, acute and chronic bacterial sinusitis, exacerbation of chronic obstructive pulmonary disease, *Bordetella pertussis* infection, asthma, postnasal-drip syndromes, gastroesophageal reflux disease, eosinophilic and chronic bronchitis, and angiotensin-converting-enzyme inhibitors, cough is categorically described as acute, subacute, or chronic, respectively lasting less than three weeks, three to eight weeks, and more than eight weeks in duration (see Irwin et. al., The New England Journal of Medicine, 343(23):1715-1721 (2000)).

Current standard of care for the treatment of cough consists of centrally and peripherally acting suppressants such as opioids and local anesthetics respectively, both of which are dose-limited by side-effects (see Cox et. al., Best Practice & Research Clinical Anaesthesiology, 117(1):111-136 (2003) and Benyamin et. al., Pain Physician, 11:S105-S120 (2008)). Opioids primarily act on t-opioid receptors of the central nervous system, and in some reports, also on peripheral afferents of the cough reflex arc—they exhibit varied degrees of efficacy and are limited by side-effects such as sedation, physical dependence, and gastrointestinal problems; morphine has shown to be an effective treatment for chronic cough (see Morice et. al., Am J Respir Crit Care Med 175:312-315 (2007) and Takahama et. al., Cough 3:8 (2007)), but is generally restricted to patients with terminal illness such as lung cancer. Codeine, found in some cough syrups, and also administered systemically, was found no more effective than placebo (see Smith et. al., Journal of Allergy and Clinical Immunology, 117:831-835 (2006). Local anesthetics act peripherally by reducing the generation of action potentials in sensory nerves of the airway as a result of non-selectively inhibiting all voltage gated sodium channel subtypes and have demonstrated varied degrees of efficacy in treating cough. These compounds are often found in over-the-counter lozenges and have been shown to relieve cough when administered via nebulisation (see Nasra et. al., Pharmacology & Therapeutics, 124(3):354-375 (2009) and Hansson et. al., Thorax, 49(11): 1166-1168 (1994)). However, in a study with chronic obstructive pulminary disease patients, lidocaine was not effective (see Chong et. al., Emerg Med J, 22(6):429-32 (2005)).

In pre-clinical animals, $Na_v 1.7$, $Na_v 1.8$, and $Na_v 1.9$ were determined to be the primary voltage-gated sodium channels expressed in the afferent nerves of the respiratory tract (see Muroi et. al., Lung, 192:15-20 (2014)) and in animal models of cough, suppression of $Na_v 1.7$ function resulted in a marked decrease in number of coughs (see Muroi et. al., Am J Physiol Regul integr Comp Physiol, 304:R1017-R0123 (2013)), thus, combined with previous evidence that local anesthetics can be effective antitussive agents, the targeted blockade of $Na_v 1.7$ channels is believed to represent a rational approach for the treatment of cough with a preferential side-effect profile as compared to local anesthetics. Local anesthetics undesirably inhibit all voltage gated sodium channels, such as $Na_v 1.5$ channels which are found in heart muscle (see Rook et. al., Cardiovascular Research 93:12-23 (2012)).

Pruritus, also commonly known as itch, affects approximately 4% of the global population (see Flaxman et. al., Lancet, 380:2163-2196 (2012)) is "an unpleasant sensation that elicits the desire or reflex to scratch" and is regarded as closely related to pain. Theories on the origin of itch implicate the subtle, low-frequency activation of nociceptors (pain-sensing neurons), however, it has been described that some afferents preferentially respond to histamine, which induces itch (see Schmelz et. al., J Neuroscience, 17(20): 8003-8008 (1997)). At the same time, it has been found that histamine-responding neurons also respond to capsaicin which produces pain (see McMahon et. al., Trends. Neurosci., 15:497-501 (1992)). Members of the transient receptor potential (TRP) family, and nerve growth factor (NGF) are both known to play a role in itch and pain, and clinically, both maladies are treated with therapeutic agents such as gabapentin and antidepressants—as such, it continues to be accepted that the underlying mechanisms of pain and itch are highly interwoven and complex, and distinguishing pan-selective or itch-selective pathways remains ambiguous (see Ikoma et. al., Nature Reviews Neuroscience, 7:535-547 (2006)).

Itch, both chronic and acute, can arise from many different insults and diseases and may be classified as dermal or pruriceptive, neurogenic, neuropathic, or psychogenic: itch can arise from both systemic disorders, skin disorders, as well as physical or chemical insult to the dermis. Pathologically, conditions such as dry skin, eczema, psoriasis, varicella zoster, urticaria, scabies, renal failure, cirrhosis, lymphoma, iron deficiency, diabetes, menopause, polycythemia, uremia, and hyperthyroidism can cause itch, as can diseases of the nervous system such as tumors, multiple sclerosis, peripheral neuropathy, nerve compression, and delusions related to obsessive-compulsive disorders. In skin, pruritogens are released from keratinocytes, lymphocytes, mast cells, and eosinophils during inflammation. These molecules act directly on free nerve endings to induce itch; medicines such as opioids and chloroquine can also trigger itch (see Ikoma et. al., Nature Reviews Neuroscience, 7:535-547 (2006)). Itching following burn is also an extremely serious clinical problem as it hampers the healing process, results in permanent scaring, and negatively impacts quality of life (see Loey et. al., British Journal of Dermatology, 158:95-100 (2008)).

Gain of function mutations of $Na_v 1.7$ have been found in approximately 28% of patients with idiopathic small fiber neuropathy (I-SFN); these mutations were found to render dorsal root ganglia neurons hyperexcitable, reducing the threshold of activation and increasing the frequency of evoked firing (see Waxman et. al., Neurology, 78(21): 1635-1643 (2012)). Severe, uncontrollable itch has also been genetically linked to a gain-of-function mutation (1739V) in the sodium channel $Na_v 1.7$ in man (see see Devigili et. al., Pain, 155(9); pp 1702-7 (2014)). Additionally, the sea-anemone toxin ATX-II has been found to elicit pain and itch in human volunteers after intradermal injection on the forearm; electrophysiology studies revealed that ATX-II enhanced $Na_v 1.7$ and $Na_v 1.6$ resurgent currents (see Klinger et. al., Molecular Pain, 8:69 (2012)). It has been demonstrated in animal models that selective blockade of $Na_v 1.7$ channels can effectively suppress both inflammatory and neuropathic pain, as well as acute and chronic itch, thus blockade of $Na_v 1.7$ channels is believed to represent a rational approach to treatment of pain and itch disorders (see Lee et. al., Cell, 157:1-12 (2014)).

Because voltage gated sodium ion channels are ubiquitous in the central and peripheral nervous system, as well as in both cardiac and skeletal muscle, and conservation of structures in the various Alpha-subunits characterizing voltage-gated sodium ion channels implicates the potential for producing serious side effects when utilizing therapeutic agents having a mechanism of action that target inhibition of voltage-gated sodium ion channels, for example, therapeutic agents suitable for use in addressing nociception, cough, or itch disorders, requires therapeutic agents having specificity in their action, for example, discriminating between action upon $Na_v 1.5$ sodium ion channels, thought to be important in regulation of cardiac function and action upon $Na_v 1.7$ sodium ion channels, thought to be central in inflammatory nociception, cough, or itch and disorders arising from dysfunctional $Na_v 1.7$ sodium ion channels.

There remains a need for additional compounds having high potency for inhibiting $Na_v 1.7$ sodium ion channels and selective activity for $Na_v 1.7$ sodium ion channels providing structural variety to facilitate rational development of therapeutic agents for use as a selective Na$_v$ 1.7 sodium ion channel inhibitor.

SUMMARY OF THE INVENTION

In one aspect, the invention provides compounds having selective activity as Na$_v$ 1.7 sodium ion channel inhibitors which have the structure of Formula A$^1$, or a salt thereof:

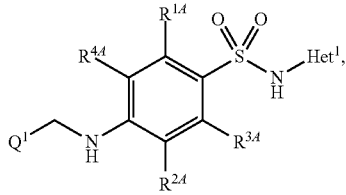

Formula A$^1$ wherein:
Het$^1$ is a five or six member heteroaryl moiety comprising up to five carbon atoms and one or more heteroatoms selected from N and S, which is optionally substituted on any ring carbon thereof by a halogen or methyl, which methyl moiety may optionally be fluorine substituted, but is not selected to be a moiety of the following formula:

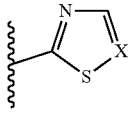

wherein X is —N= or —C(R$^{18A}$)=, wherein R$^{18A}$ is H, —Cl or —F;
R$^{1A}$ to R$^{4A}$ are independently —F, —Cl, —Br, —CN, —H, or a linear, branched or cyclic alkyl of up to 4 carbon atoms which may optionally be substituted on any carbon thereof with one or more fluorine, with the proviso that at least one of R$^{1A}$ to R$^{4A}$ is not —H and at least two of R$^{1A}$ to R$^{4A}$ are selected to be —H;
Q$^1$ is
(a) a moiety of the formula A$^1$-NH—X$^1$—, wherein:
X$^1$ is:
(i) alkyl of three or four carbon atoms which is optionally substituted on one or more carbon atoms thereof with halogen, benzyl, aryl, or a linear or branched alkyl of up to 4 carbon atoms; or
(ii) a moiety of the formula:

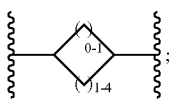

A$^1$ is:
(i) R$^{1b}$—CHR$^{2b}$—, wherein
R$^{2b}$ is: (ai) -aryl; (aii) —CH$_3$; (aiii) —H; or (aiv) halogen; and R$^{1b}$ is:
(ai) a moiety of the formula:

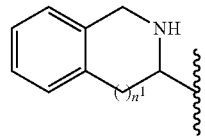

wherein n$^1$ is 0 or 1;
(aii) a moiety of the formula:

R$^{3b}$NH—CH$_2$—(CHR$^{4b}$)$_{0-3}$—, wherein:
(ai) R$^{3b}$ is —H; linear or branched alkyl of up to 4 carbon, or a moiety of the formula:

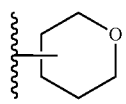

wherein the moiety is bonded via a carbon beta or gamma to the oxygen; and
(aii) R$^{4b}$ is —H or —F;
(aiii) a moiety of the formula:

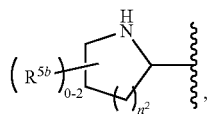

wherein:
n$^2$ is 1 or 2; and
R$^{5b}$ is up to two optional substituents bonded to one or more available ring carbon atoms which are independently for each occurrence: —F; —O-aryl; aryl; —CN; —O—CH$_3$; or

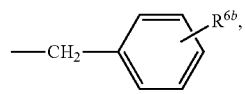

wherein R$^{6b}$ is an is an optional substituent bonded to an available ring carbon atom which, if present, is halogen or —O—CH$_3$, and if selected to be halogen is preferably F or Cl; or
(aiv) aryl, which is substituted on one ring carbon atom thereof with —CH$_2$NH$_2$;
(ii) a moiety of the formula:

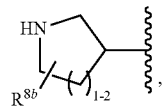

wherein $R^{8b}$ is —H or aryl;
(iii) a moiety of the formula: or

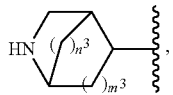

wherein $n^3$ is 1 or 2 and $m^3$ is 0 or 1;
(iv) adamantyl bonded to the nitrogen via any available carbon atom;
(b) a moiety of the formula:

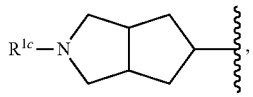

wherein $R^{1c}$ is a moiety of the formula:

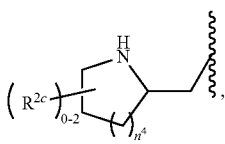

wherein:
$n^4$ is 1 or 2; and
$R^{2c}$ is up to two optional substituents which are independently for each occurrence: —F; —O-aryl; aryl; —CN; —O—CH$_3$; or

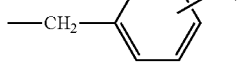

wherein $R^{3c}$ is an optional substituent bonded to an available ring carbon atom which, if present, is —O—CH$_3$; or
(c) a moiety of the formula $A^2$-$X^2$—, wherein:
$X^2$ is a linear or branched alkyl of three or four carbon atoms; and
$A^2$ is:
(i) a moiety of the formula:

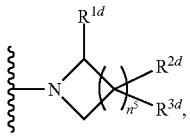

wherein:
$n^5$=1-4;
$R^{1d}$ is —H or —CH$_2$NH$_2$; and
$R^{2d}$ and $R^{3d}$ are selected as follows:
if $R^{1d}$ is selected to be —CH$_2$—NH$_2$, then for all occurrences, $R^{2d}$ and $R^{3d}$ are —H; or if $R^{1d}$ is —H, then at least one of $R^{2d}$ or $R^{3d}$ is: (ai) —CH$_2$—NH$_2$; (aii) —NH—CH$_3$; or (aiii) —NH$_2$, and the others of $R^{2d}$ and $R^{3d}$ are independently for each occurrence: (ai) —H; (ii) linear-, branched, or cyclic alkyl of up to 6 carbon atoms; or (aiii) aryl;
(ii) a moiety of the formula:

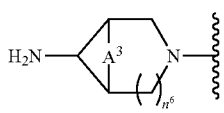

wherein:
$n^6$ is 0 or 1;
if $n^6$=0, then $A^3$ is —(CH$_2$)$_2$—;
if $n^6$=1, then $A^3$ is a bond between the two ring carbon atoms;
(iii) a moiety of the formula:

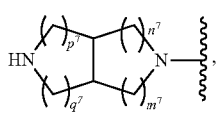

wherein:
p=1-3;
$q^7$ and $m^7$ are independently=0 or 1;
$n^7$=1 or 2;
(iv) a moiety of the formula:

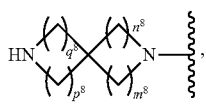

wherein:
$m^8$ and $q^8$ are independently 1, 2 or 3;
$n^8$ and $p^8$ are independently 0 or 1; and
m+n≤4; or
(v) a moiety of the formula:

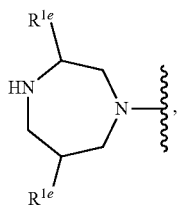

Wherein: (i) both $R^{1e}$ are —H; or (ii) both $R^{1e}$ taken together form a bridge of the formula —(CH$_2$)$_{1-3}$.

In one aspect, the invention provides compounds having selective activity as Na$_v$ 1.7 sodium ion channel inhibitors which have the structure of Formula $A^2$, or a salt thereof:

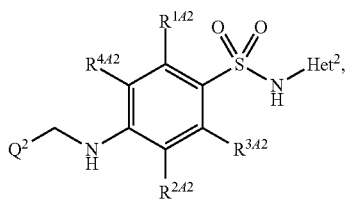

Formula A² wherein:
Het² is a five or six member heteroaryl moiety comprising up to five carbon atoms and one or more heteroatoms selected from N and S, which is optionally substituted on any ring carbon thereof by a halogen or methyl, which methyl may optionally be fluorine substituted;
$R^{1A2}$ to $R^{4A2}$ are independently —F, —Cl, —Br, —CN, —H, or a linear, branched or cyclic alkyl of up to 4 carbon atoms which may optionally be substituted on any carbon thereof with one or more fluorine, with the following provisos: (i) at least one of $R^{1A2}$ to $R^{4A2}$ is not —H; (ii) at least two of $R^{1A2}$ to $R^{4A2}$ are selected to be —H; and (iii) $R^{1A2}$ is not selected to be —F if $R^{2A2}$ is —F, —Cl or Br;
Q² is
(a) a moiety of the formula $A^{1b}$-NH—$X^{1b}$—, wherein:
  $X^{1b}$ is:
    (i) alkyl of three or four carbon atoms which is optionally substituted on one or more carbon atoms thereof with halogen, benzyl, aryl, or linear or branched alkyl of up to 4 carbon atoms; or
    (ii) a moiety of the formula:

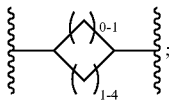

and
$A^{1b}$ is:
  (i) $R^{1b}$—$CHR^{2b}$—, wherein
    $R^{2b}$ is: (ai) -aryl; (aii) —CH₃; (aiii) —H; or (aiv) halogen; and
    $R^{1b}$ is:
      (ai) a moiety of the formula:

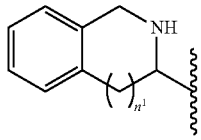

wherein n¹ is 0 or 1;
    (aii) a moiety of the formula:
    $R^{3b}$NH—CH₂—$(CHR^{4b})_{0-3}$—,
    wherein:
      (ai) $R^{3b}$ is —H; linear or branched alkyl of up to 4 carbon atoms, or a moiety of the formula:

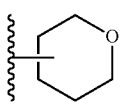

wherein the moiety is bonded via a carbon beta or gamma to the oxygen; and
    (aii) $R^{4b}$ is —H or —F;
  (aiii) a moiety of the formula:

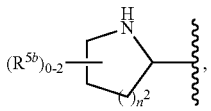

wherein:
    n² is 1 or 2; and
    $R^{5b}$ is up to two optional substituents bonded to one or more available ring carbon atoms which are independently for each occurrence: —F; —O-aryl; aryl; —CN; —O—CH₃; or

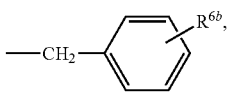

wherein $R^{6b}$ is an is an optional substituent bonded to an available ring carbon atom which, if present, is is halogen or —O—CH₃, and if sleeted to be halogen is preferably F or Cl; or
  (aiv) aryl, which is substituted on one ring carbon atom thereof with —CH₂NH₂;
  (ii) a moiety of the formula:

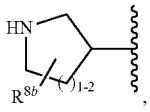

wherein $R^{8b}$ is —H or aryl;
  (iii) a moiety of the formula: or

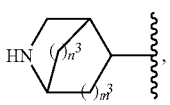

wherein n³ is 1 or 2 and m³ is 0 or 1;
  (iv) adamantyl bonded to the nitrogen via any available carbon atom;
(b) a moiety of the formula:

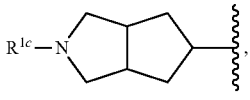

wherein $R^{1c}$ is a moiety of the formula:

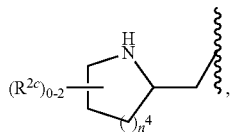

wherein:
n⁴ is 1 or 2; and
$R^{2c}$ is up to two optional substituents which are independently for each occurrence: —F; —O-aryl; aryl; —CN; —O—$CH_3$; or

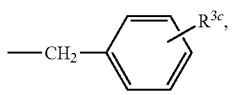

wherein $R^{3c}$ is an optional substituent bonded to an available ring carbon atom which, if present, is —O—$CH_3$; or
(c) a moiety of the formula $A^2$-$X^2$—, wherein:
$X^2$ is a linear or branched alkyl of three or four carbon atoms; and
$A^2$ is:
(i) a moiety of the formula:

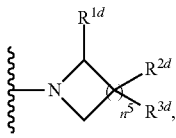

wherein:
n=1-4;
$R^{1d}$ is —H or —$CH_2NH_2$; and
$R^{2d}$ and $R^{3d}$ are selected as follows:
if $R^{1d}$ is selected to be —$CH_2$—$NH_2$, then for all occurrences, $R^{2d}$ and $R^{3d}$ are —H; or if $R^{1d}$ is —H, then at least one of $R^{2d}$ or $R^{3d}$ is: (ai) —$CH_2$—$NH_2$; (aii) —NH—$CH_3$; or (aiii) —$NH_2$, and the others of $R^{2d}$ and $R^{3d}$ are independently for each occurrence: (ai) —H; (ii) linear-, branched, or cyclic alkyl of up to 6 carbon atoms; or (aiii) aryl;
(ii) a moiety of the formula:

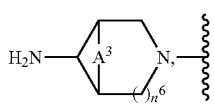

wherein:
n⁶ is 0 or 1;
if n⁶=0, then $A^3$ is —$(CH_2)_2$—;
if n⁶=1, then $A^3$ is a bond between the two ring carbon atoms;

(iii) a moiety of the formula:

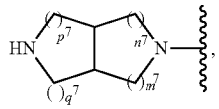

wherein:
p=1-3;
q⁷ and m⁷ are independently=0 or 1;
n⁷=1 or 2;
(iv) a moiety of the formula:

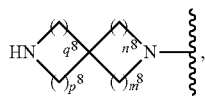

wherein:
m⁸ and q⁸ are independently 1, 2 or 3;
n⁸ and p⁸ are independently 0 or 1; and
m+n≤4; or
(v) a moiety of the formula:

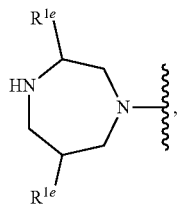

wherein: (i) both $R^{1e}$ are —H; or (ii) both $R^{1e}$ taken together form a bridge of the formula —$(CH_2)_{1-3}$—.

In one aspect, the invention provides compounds having selective activity as $Na_v$ 1.7 sodium ion channel inhibitors which have the structure of Formula $A^3$, or a salt thereof:

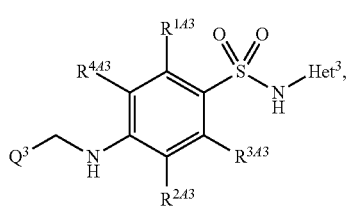

Formula $A^3$ wherein:
$Het^3$ is a five or six member heteroaryl moiety comprising up to 5 carbon atoms and one or more heteroatoms selected from N and S, which is optionally substituted on any ring carbon thereof by a halogen or methyl, which methyl may optionally be fluorine substituted;
$R^{1A3}$ to $R^{4A3}$ are independently —F, —Cl, —Br, —CN, —H, or a linear, branched or cyclic alkyl of up to 4 carbon atoms which may optionally be substituted on any carbon thereof with one or more fluorine, with the proviso that at least one of $R^{1A3}$ to $R^{4A3}$ is not —H and at least two of $R^{1A3}$ to $R^{4A3}$ are selected to be —H;

$Q^3$ is (a) a moiety of the formula $A^{1c}$-NH—$X^{1c}$—, wherein:

$X^{1c}$ is:
(i) alkyl of three or four carbon atoms which is optionally substituted on one or more carbon atoms thereof with halogen, benzyl, aryl, or linear or branched alkyl of up to 4 carbon atoms with the proviso that $X^1$ is not —CH(Y)—CH$_2$—CH$_2$— wherein Y is —H or CH$_3$; or (ii) a moiety of the formula:

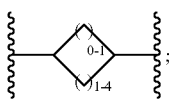

and $A^{1c}$ is:
(i) $R^{1b}$—CHR$^{2b}$—, wherein
$R^{2b}$ is: (ai) -aryl; (aii) —CH$_3$; (aiii) —H; or (aiv) halogen; and
$R^{1b}$ is:
(ai) a moiety of the formula:

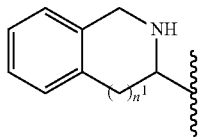

wherein $n^1$ is 0 or 1;
(aii) a moiety of the formula:

$R^{3b}$NH—CH$_2$—(CHR$^{4b}$)$_{0-3}$—, wherein:
(ai) $R^{3b}$ is —H; linear or branched alkyl of up to 4 carbon atoms, or a moiety of the formula:

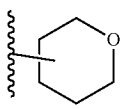

wherein the moiety is bonded via a carbon beta or gamma to the oxygen; and
(aii) $R^{4b}$ is —H or —F;
(aiii) a moiety of the formula:

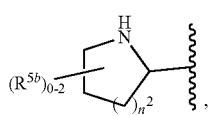

wherein:
$n^2$ is 1 or 2; and
$R^{5b}$ is up to two optional substituents bonded to one or more available ring carbon atoms which are independently for each occurrence: —F; —O-aryl; aryl; —CN; —O—CH$_3$; or

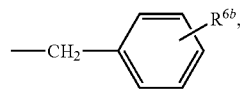

wherein $R^{6b}$ is an is an optional substituent bonded to an available ring carbon atom which, if present, is halogen or —O—CH$_3$, and if sleeted to be halogen is preferably F or Cl; or
(aiv) aryl, which is substituted on one ring carbon atom thereof with —CH$_2$NH$_2$;
(ii) a moiety of the formula:

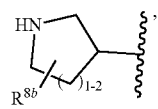

wherein $R^{8b}$ is —H or aryl;
(iii) a moiety of the formula: or

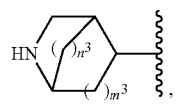

wherein $n^3$ is 1 or 2 and $m^3$ is 0 or 1;
(iv) adamantyl bonded to the nitrogen via any available carbon atom;

(b) a moiety of the formula:

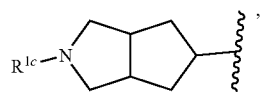

wherein $R^{1c}$ is a moiety of the formula:

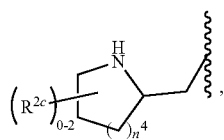

wherein:
$n^4$ is 1 or 2; and
$R^{2c}$ is up to two optional substituents which are independently for each occurrence: —F; —O-aryl; aryl; —CN; —O—CH$_3$; or

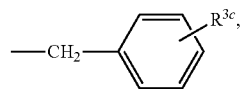

wherein $R^{3c}$ is an optional substituent bonded to an available ring carbon atom which, if present, is —O—CH$_3$; or (c) a moiety of the formula $A^2$-$X^2$—, wherein:
  $X^2$ is a linear or branched alkyl three or four carbon atoms; and
  $A^2$ is:
    (i) a moiety of the formula:

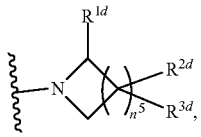

wherein:
  $n^5$=1-4;
  $R^{1d}$ is —H or —$CH_2NH_2$; and
  $R^{2d}$ and $R^{3d}$ are selected as follows:
    if $R^{1d}$ is selected to be —$CH_2$—$NH_2$, then for all occurrences, $R^{2d}$ and $R^{3d}$ are —H; or if $R^{1d}$ is —H, then at least one of $R^{2d}$ or $R^{3d}$ is: (ai) —$CH_2$—$NH_2$; (aii) —NH—$CH_3$; or (aiii) —$NH_2$, and the others of $R^{2d}$ and $R^{3d}$ are independently for each occurrence: (ai) —H; (ii) linear-, branched, or cyclic alkyl of up to 6 carbon atoms; or (aiii) aryl;
(ii) a moiety of the formula:

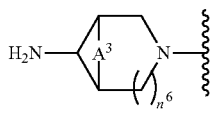

wherein:
  $n^6$ is 0 or 1;
  if $n^6$=0, then $A^3$ is —$(CH_2)_2$—;
  if $n^6$=1, then $A^3$ is a bond between the two ring carbon atoms;
(iii) a moiety of the formula:

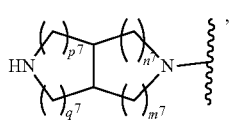

wherein:
  p=1-3;
  $q^7$ and $m^7$ are independently=0 or 1;
  $n^7$=1 or 2;
(iv) a moiety of the formula:

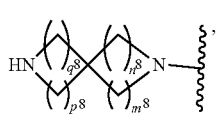

wherein:
  $m^8$ and $q^8$ are independently 1, 2 or 3;
  $n^8$ and $p^8$ are independently 0 or 1; and
  m+n≤4; or (v) a moiety of the formula:

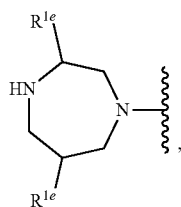

wherein: (i) both $R^{1e}$ are —H; or (ii) both $R^{1e}$ taken together form a bridge of the formula —$(CH_2)_{1-3}$—.

In some embodiments, the salt of a compound of Formula A is preferably a pharmaceutically acceptable salt.

In some embodiments, preferably $R^{1A}$, $R^{2A}$ and $R^{3A}$ are —H, and $R^{4A}$ is —Cl.

In some embodiments, preferably $R^{1A}$, $R^{3A}$ and $R^{4A}$ are —H, and $R^{2A}$ is —$CF_3$.

In some embodiments, preferably $R^{1A}$ and $R^{2A}$ are —H, and $R^{3A}$ and $R^{4A}$ are —F.

In some embodiments where Q is $Q^1$-NH—$X^1$, it is preferred for $X^1$ to be selected to provide a moiety of the formula:

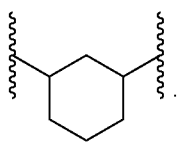 [SMILES: *C1CCCC(*)C1]

In some embodiments where Q is a moiety of the formula:

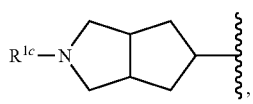

it is preferred for $R^{1c}$ to be

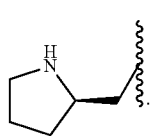 [SMILES: *C[C@H]1CCCN1]

In some embodiments it is preferred for the inventive compound to be:
4-[(4-{[2-(benzylamino)ethyl]amino}butyl)amino]-5-chloro-2-fluoro-N-1,3-thiazol-2-ylbenzenesulfonamide;
5-chloro-2-fluoro-4-[(4-{[(3R,5S)-5-phenylpyrrolidin-3-yl]amino}butyl)amino]-N-1,3-thiazol-2-ylbenzenesulfonamide;
5-chloro-2-fluoro-4-({4-[(1,2,3,4-tetrahydroisoquinolin-3-ylmethyl)amino]butyl}amino)-N-1,3-thiazol-2-ylbenzenesulfonamide;
4-({4-[(3S)-3-aminopyrrolidin-1-yl]butyl}amino)-5-chloro-2-fluoro-N-1,3-thiazol-2-ylbenzenesulfonamide;
5-chloro-4-{[4-(1,7-diazaspiro[4.4]non-1-yl)butyl]amino}-2-fluoro-N-1,3-thiazol-2-ylbenzenesulfonamide;
5-chloro-2-fluoro-4-{[4-(octahydro-6H-pyrrolo[3,4-b]pyridin-6-yl)butyl]amino}-N-1,3-thiazol-2-ylbenzenesulfonamide;

5-chloro-4-{[4-(1,8-diazaspiro[4.5]dec-8-yl)butyl]amino}-2-fluoro-N-1,3-thiazol-2-ylbenzenesulfonamide;
(R)-5-chloro-2-fluoro-4-{[4-({[2-(4-methoxybenzyl)pyrrolidin-2-yl]methyl}amino)butyl]amino]-N-1,3-thiazol-2-ylbenzenesulfonamide;
(S)-5-chloro-2-fluoro-4-{[4-({[2-(4-methoxybenzyl)pyrrolidin-2-yl]methyl}amino)butyl]amino]-N-1,3-thiazol-2-ylbenzenesulfonamide;
5-chloro-2-fluoro-4-{[4-({[2-(4-methoxybenzyl)pyrrolidin-2-yl]methyl}amino)butyl]amino}-N-1,3-thiazol-2-ylbenzenesulfonamide;
4-({4-[(1R,4R,7S)-2-azabicyclo[2.2.1]hept-7-ylamino]butyl}amino)-5-chloro-2-fluoro-N-1,3-thiazol-2-ylbenzenesulfonamide;
(R) 5-chloro-2-fluoro-4-({4-[(1,2,3,4-tetrahydroisoquinolin-3-ylmethyl)amino]butyl}amino)-N-1,3-thiazol-2-ylbenzenesulfonamide;
(S) 5-chloro-2-fluoro-4-({4-[(1,2,3,4-tetrahydroisoquinolin-3-ylmethyl)amino]butyl}amino)-N-1,3-thiazol-2-ylbenzenesulfonamide;
5-chloro-2-fluoro-4-({4-[(1,2,3,4-tetrahydroisoquinolin-3-ylmethyl)amino]butyl}amino)-N-1,3-thiazol-2-ylbenzenesulfonamide;
4-({4-[(1R,4R,7S)-7-amino-2-azabicyclo[2.2.1]hept-2-yl]butyl}amino)-5-chloro-2-fluoro-N-1,3-thiazol-2-ylbenzenesulfonamide;
5-chloro-2-fluoro-4-({4-[(3aS,7aR)-octahydro-1H-pyrrolo[2,3-c]pyridin-1-yl]butyl}amino)-N-1,3-thiazol-2-ylbenzenesulfonamide;
5-chloro-2-fluoro-4-({4-[(3aR,6aS)-hexahydropyrrolo[3,4-c]pyrrol-2(1H)-yl]butyl}amino)-N-1,3-thiazol-2-ylbenzenesulfonamide;
5-chloro-2-fluoro-4-({4-[(3aR,7aR)-octahydro-2H-pyrrolo[3,4-c]pyridin-2-yl]butyl}amino)-N-1,3-thiazol-2-ylbenzenesulfonamide;
4-({4-[(1S,4S)-2-azabicyclo[2.2.1]hept-5-ylamino]butyl}amino)-5-chloro-2-fluoro-N-1,3-thiazol-2-ylbenzenesulfonamide;
4-({4-[(1S,4S,7R)-2-azabicyclo[2.2.1]hept-7-ylamino]butyl}amino)-5-chloro-2-fluoro-N-1,3-thiazol-2-ylbenzenesulfonamide;
5-chloro-2-fluoro-4-[(4-{[(1R)-1-methyl-2-(tetrahydro-2H-pyran-4-ylamino)ethyl]amino}butyl)amino]-N-1,3-thiazol-2-ylbenzenesulfonamide;
5-chloro-2-fluoro-4-({4-[(5-phenylpiperidin-3-yl)amino]butyl}amino)-N-1,3-thiazol-2-ylbenzenesulfonamide;
4-({4-[(2-amino-1-phenylethyl)amino]butyl}amino)-5-chloro-N-1,3-thiazol-2-ylbenzenesulfonamide;
5-chloro-2-fluoro-4-{[4-({[2-(3-methoxybenzyl)pyrrolidin-2-yl]methyl}amino)butyl]amino}-N-1,3-thiazol-2-ylbenzenesulfonamide;
4-({4-[(3R)-3-aminopiperidin-1-yl]butyl}amino)-5-chloro-2-fluoro-N-1,3-thiazol-2-ylbenzenesulfonamide;
4-({4-[(3R)-3-aminopyrrolidin-1-yl]butyl}amino)-5-chloro-2-fluoro-N-1,3-thiazol-2-ylbenzenesulfonamide;
4-({4-[(3S)-3-aminopiperidin-1-yl]butyl}amino)-5-chloro-2-fluoro-N-1,3-thiazol-2-ylbenzenesulfonamide;
5-chloro-4-{[4-(2,7-diazaspiro[4.4]non-2-yl)butyl]amino}-2-fluoro-N-1,3-thiazol-2-ylbenzenesulfonamide;
5-chloro-4-{[4-(1,7-diazaspiro[4.5]dec-7-yl)butyl]amino}-2-fluoro-N-1,3-thiazol-2-ylbenzenesulfonamide;
5-chloro-4-{[4-(1,6-diazaspiro[3.5]non-1-yl)butyl]amino}-2-fluoro-N-1,3-thiazol-2-ylbenzenesulfonamide;
4-({4-[(2R)-2-(aminomethyl)pyrrolidin-1-yl]butyl}amino)-5-chloro-2-fluoro-N-1,3-thiazol-2-ylbenzenesulfonamide;
4-{[4-(6-amino-3-azabicyclo[3.1.0]hex-3-yl)butyl]amino}-5-chloro-2-fluoro-N-1,3-thiazol-2-ylbenzenesulfonamide;
4-{[4-(4-aminoazepan-1-yl)butyl]amino}-5-chloro-2-fluoro-N-1,3-thiazol-2-ylbenzenesulfonamide;
4-{[4-(3-aminoazetidin-1-yl)butyl]amino}-5-chloro-2-fluoro-N-1,3-thiazol-2-ylbenzenesulfonamide;
4-({4-[4-(aminomethyl)-4-phenylpiperidin-1-yl]butyl}amino)-5-chloro-2-fluoro-N-1,3-thiazol-2-ylbenzenesulfonamide;
4-({4-[3-(aminomethyl)piperidin-1-yl]butyl}amino)-5-chloro-2-fluoro-N-1,3-thiazol-2-ylbenzenesulfonamide;
4-({4-[3-(aminomethyl)pyrrolidin-1-yl]butyl}amino)-5-chloro-2-fluoro-N-1,3-thiazol-2-ylbenzenesulfonamide;
5-chloro-2-fluoro-4-{[4-(octahydro-5H-pyrrolo[3,4-c]pyridin-5-yl)butyl]amino}-N-1,3-thiazol-2-ylbenzenesulfonamide;
4-{[4-(4-aminopiperidin-1-yl)butyl]amino}-5-chloro-2-fluoro-N-1,3-thiazol-2-ylbenzenesulfonamide;
4-({4-[3-(aminomethyl)-3-phenylpyrrolidin-1-yl]butyl}amino)-5-chloro-2-fluoro-N-1,3-thiazol-2-ylbenzenesulfonamide;
4-({4-[3-(aminomethyl)azetidin-1-yl]butyl}amino)-5-chloro-2-fluoro-N-1,3-thiazol-2-ylbenzenesulfonamide;
5-chloro-4-{[4-(3,9-diazabicyclo[4.2.1]non-3-yl)butyl]amino}-2-fluoro-N-1,3-thiazol-2-ylbenzenesulfonamide;
5-chloro-4-{[4-(1,4-diazepan-1-yl)butyl]amino}-2-fluoro-N-1,3-thiazol-2-ylbenzenesulfonamide;
(R)-5-chloro-2-fluoro-4-((4-((isoindolin-1-ylmethyl)amino)butyl)amino)-N-(thiazol-2-yl)benzenesulfonamide;
(S)-5-chloro-2-fluoro-4-((4-((isoindolin-1-ylmethyl)amino)butyl)amino)-N-(thiazol-2-yl)benzenesulfonamide;
5-chloro-2-fluoro-4-((4-((isoindolin-1-ylmethyl)amino)butyl)amino)-N-(thiazol-2-yl)benzenesulfonamide;
4-((4-((2-(aminomethyl)benzyl)amino)butyl)amino)-5-chloro-2-fluoro-N-(thiazol-2-yl)benzenesulfonamide;
5-chloro-2-fluoro-4-((((1S,3R)-3-(((S)-pyrrolidin-2-ylmethyl)amino)cyclohexyl)methyl)amino)-N-(thiazol-2-yl)benzenesulfonamide;
5-chloro-2-fluoro-4-((((1R,3S)-3-(((S)-pyrrolidin-2-ylmethyl)amino)cyclohexyl)methyl)amino)-N-(thiazol-2-yl)benzenesulfonamide;
5-chloro-2-fluoro-4-[({(3aR,5R,6aS)-2-[(2S)-pyrrolidin-2-ylmethyl]octahydro-cyclopenta[c]pyrrol-5-yl}methyl)amino]-N-1,3-thiazol-2-ylbenzenesulfonamide;
5-chloro-2-fluoro-4-[(5-phenyl-4-{[(2S)-pyrrolidin-2-ylmethyl]amino}pentyl)amino]-N-1,3-thiazol-2-ylbenzenesulfonamide;
4-[(4-1{[(2S)-pyrrolidin-2-ylmethyl]amino}butyl)amino]-N-1,3-thiazol-2-yl-3-(trifluoromethyl)benzenesulfonamide;
2,5-difluoro-4-[(4-{[(2S)-pyrrolidin-2-ylmethyl]amino}butyl)amino]-N-1,2,4-thiadiazol-5-ylbenzenesulfonamide;
3-chloro-4-[(4-{[(2S)-pyrrolidin-2-ylmethyl]amino}butyl)amino]-N-1,3-thiazol-2-ylbenzenesulfonamide;
3-chloro-N-(5-fluoro-1,3-thiazol-2-yl)-4-[(4-{[(2S)-pyrrolidin-2-ylmethyl]amino}butyl)amino]benzenesulfonamide;
(S)-5-chloro-4-((4-(((4,4-difluoropyrrolidin-2-yl)methyl)amino)butyl)amino)-2-fluoro-N-(thiazol-2-yl)benzenesulfonamide;
5-chloro-2-fluoro-4-{[4-({[(2S,5R)-5-phenylpyrrolidin-2-yl]methyl}amino)butyl]amino}-N-1,3-thiazol-2-ylbenzenesulfonamide;

5-chloro-2-fluoro-4-{[4-({[(2S,4S)-4-phenylpyrrolidin-2-yl]methyl}amino)butyl]amino}-N-1,3-thiazol-2-ylbenzenesulfonamide;
5-chloro-2-fluoro-4-{[4-({[(2S,4S)-4-phenoxypyrrolidin-2-yl]methyl}amino)butyl]amino}-N-1,3-thiazol-2-ylbenzenesulfonamide;
5-chloro-2-fluoro-4-{[4-({[(2S,3R)-3-phenylpyrrolidin-2-yl]methyl}amino)butyl]amino}-N-1,3-thiazol-2-ylbenzenesulfonamide;
5-chloro-4-{[4-({[(2S,4R)-4-cyanopyrrolidin-2-yl]methyl}amino)butyl]amino}-2-fluoro-N-1,3-thiazol-2-ylbenzenesulfonamide;
5-chloro-2-fluoro-4-{[4-({[(2R,4S)-4-phenylpyrrolidin-2-yl]methyl}amino)butyl]amino}-N-1,3-thiazol-2-ylbenzenesulfonamide;
5-chloro-2-fluoro-4-{[4-({[(2S,4R)-4-phenylpyrrolidin-2-yl]methyl}amino)butyl]amino}-N-1,3-thiazol-2-ylbenzenesulfonamide;
5-chloro-2-fluoro-4-[(4-{[(5-phenylpiperidin-2-yl)methyl]amino}butyl)amino]-N-1,3-thiazol-2-ylbenzenesulfonamide;
5-chloro-4-{[4-({[(2R)-4,4-difluoropyrrolidin-2-yl]methyl}amino)butyl]amino}-2-fluoro-N-1,3-thiazol-2-ylbenzenesulfonamide;
5-chloro-2-fluoro-4-{[4-({[(2S,4R)-4-methoxypyrrolidin-2-yl]methyl}amino)butyl]amino}-N-1,3-thiazol-2-ylbenzenesulfonamide;
(S)-5-chloro-2-fluoro-N-(6-fluoropyridin-2-yl)-4-((5-((pyrrolidin-2-ylmethyl)amino)pentyl)-amino)benzenesulfonamide;
5-chloro-2-fluoro-4-({5-[(piperidin-2-ylmethyl)-amino]pentyl}amino)-N-1,3-thiazol-2-yl-benzenesulfonamide;
5-chloro-2-fluoro-4-({5-[(piperidin-3-ylmethyl)-amino]-pentyl}amino)-N-1,3-thiazol-2-yl-benzenesulfonamide;
4-[(5-{[(2R)-2-aminopropyl]-amino}pentyl)amino]-5-chloro-2-fluoro-N-1,3-thiazol-2-yl-benzenesulfonamide;
4-({5-[(azetidin-2-ylmethyl)amino]-pentyl}amino)-5-chloro-2-fluoro-N-1,3-thiazol-2-yl-benzenesulfonamide;
5-chloro-2-fluoro-4-((2-phenyl-4-(((S)-pyrrolidin-2-ylmethyl)amino)butyl)amino)-N-(thiazol-2-yl)benzenesulfonamide;
5-chloro-4-[(2,2-difluoro-4-{[(2R)-pyrrolidin-2-ylmethyl]amino}butyl)amino]-2-fluoro-N-1,3-thiazol-2-ylbenzenesulfonamide;
5-chloro-4-[(2,2-difluoro-4-{[(2S)-pyrrolidin-2-ylmethyl]amino}butyl)amino]-2-fluoro-N-1,3-thiazol-2-ylbenzenesulfonamide,
4-({4-[(2R)-2-(aminomethyl)azetidin-1-yl]butyl}amino)-5-chloro-2-fluoro-N-1,2,4-thiadiazol-5-ylbenzene-sulfonamide;
5-chloro-2-fluoro-4-({4-[(3R)-3-(methylamino)pyrrolidin-1-yl]butyl}-amino)-N-1,2,4-thiadiazol-5-ylbenzenesulfonamide;
5-chloro-2-fluoro-N-(5-fluoro-1,3-thiazol-2-yl)-4-[(4-{[2-(tricyclo[3.3.1.1~3,7~]dec-2-ylamino)-ethyl]amino}butyl)amino]benzene-sulfonamide;
4-({4-[(2R)-2-(aminomethyl)azetidin-1-yl]butyl}amino)-5-chloro-2-fluoro-N-(5-fluoro-1,3-thiazol-2-yl)benzenesulfonamide;
4-({4-[(2S)-2-(aminomethyl)azetidin-1-yl]butyl}amino)-5-chloro-2-fluoro-N-(5-fluoro-1,3-thiazol-2-yl)benzenesulfonamide;
5-chloro-2-fluoro-N-(5-fluoro-1,3-thiazol-2-yl)-4-({4-[(4aR,7aR)-octahydro-6H-pyrrolo[3,4-b]pyridin-6-yl]butyl}amino)benzene-sulfonamide;

5-chloro-2-fluoro-4-({4-[(4aR,7aR)-octahydro-6H-pyrrolo[3,4-b]pyridin-6-yl]-butyl}amino)-N-1,2,4-thiadiazol-5-ylbenzene-sulfonamide;
4-((4-(3-(aminomethyl)azetidin-1-yl)butyl)amino)-5-bromo-2-fluoro-N-(1,2,4-thiadiazol-5-yl)benzenesulfonamide;
4-{[4-(3-aminoazetidin-1-yl)-butyl]amino}-5-chloro-2-fluoro-N-1,2,4-thiadiazol-5-yl-benzenesulfonamide;
5-cyano-2-fluoro-4-({4-[(3R)-pyrrolidin-3-ylamino]-butyl}amino)-N-1,3-thiazol-2-yl-benzenesulfonamide;
5-cyano-2-fluoro-N-(5-fluoro-1,3-thiazol-2-yl)-4-({4-[(3R)-pyrrolidin-3-yl-amino]butyl}amino)benzene-sulfonamide;
4-({4-[(1S,4R)-2-azabicyclo[2.2.1]hept-6-yl-amino]butyl}amino)-5-chloro-2-fluoro-N-1,3-thiazol-2-ylbenzene-sulfonamide;
2-fluoro-N-(5-fluoro-1,3-thiazol-2-yl)-5-methyl-4-({4-[(3R)-pyrrolidin-3-ylamino]-butyl}amino)benzene-sulfonamide;
5-bromo-2-fluoro-N-(5-fluoro-1,3-thiazol-2-yl)-4-({4-[(4aR,7aR)-octahydro-6H-pyrrolo[3,4-b]pyridin-6-yl]butyl}amino)benzene-sulfonamide;
5-cyano-2-fluoro-4-({4-[(3R)-pyrrolidin-3-yl-amino]butyl}amino)-N-1,2,4-thiadiazol-5-ylbenzene-sulfonamide;
4-({4-[(3-amino-2-fluoro-propyl)amino]butyl}amino)-5-chloro-2-fluoro-N-(5-fluoro-1,3-thiazol-2-yl)-benzenesulfonamide;
2,5-difluoro-4-[(4-{[2-(methylamino)ethyl]amino}-butyl)amino]-N-1,2,4-thiadiazol-5-ylbenzene-sulfonamide;
5-chloro-2-fluoro-4-[(4-{[2-(methylamino)ethyl]amino}-butyl)amino]-N-(4-methyl-1,3-thiazol-2-yl)benzenesulfonamide
(R) 4-({4-[2-(aminomethyl)-azetidin-1-yl]butyl}amino)-5-chloro-2-fluoro-N-1,3-thiazol-2-ylbenzene-sulfonamide;
(S) 4-({4-[2-(aminomethyl)-azetidin-1-yl]butyl}amino)-5-chloro-2-fluoro-N-1,3-thiazol-2-ylbenzene-sulfonamide;
4-({4-[2-(aminomethyl)-azetidin-1-yl]butyl}amino)-5-chloro-2-fluoro-N-1,3-thiazol-2-ylbenzene-sulfonamide; or
5-chloro-2-fluoro-N-(5-fluoro-1,3-thiazol-2-yl)-4-({4-[(3R)-3-(methylamino)-pyrrolidin-1-yl]butyl}-amino)-benzenesulfonamide,
or a pharmaceutically acceptable salt of any thereof.

In one aspect the invention provides a pharmaceutical composition comprising at least one compound of Formula A, or a salt thereof, and at least one pharmaceutically acceptable excipient adapted for administration to a patient via any pharmaceutically acceptable route, including dosage forms for oral, intravenous, subcutaneous, transcutaneous, intramuscular, intradermal, transmucosal, or intramucosal routes of administration.

In one aspect this invention provides also a pharmaceutical composition comprising a pharmaceutical carrier, an effective amount of at least one compound of Formula A, or a salt thereof, an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP, acetaminophen), and a pharmaceutically acceptable carrier.

In one aspect the invention provides also a method of treatment, management, alleviation or amelioration of conditions or disease states which can be treated, managed, alleviated or ameliorated by specific inhibiting of Nav 1.7 channel activity, the method comprising administering to a patient in need thereof a composition comprising at least one compound of Formula A, or a salt thereof, in an amount providing a serum level of at least one said compound sufficient to effect said treatment, management, alleviation or amelioration of said conditions or disease states. Preferably the condition or disease state to be treated, managed, alleviated or ameliorated include itch, cough, or pain, for example, acute pain or a chronic pain disorder. In some embodiments, the condition is preferably pain, more preferably, acute pain, peri-operative pain, post-operative pain or chronic pain.

DETAILED DESCRIPTION OF THE INVENTION

As mentioned above, the invention provides compounds believed to have selective activity as $Na_v$ 1.7 sodium ion channel inhibitors which have the structure of Formula A, or a salt thereof:

Formula A, or a salt thereof:

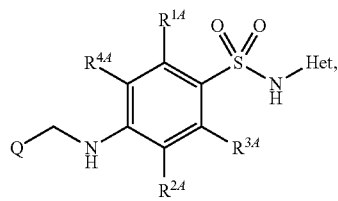

Formula A wherein:
Het, Q and $R^{1A}$ to $R^{4A}$ are defined herein.

Preferred compounds of the invention exhibit a potency (IC50) of less than about 500 nanomolar when assayed in accordance with IonWorks® assay technique described herein, and exhibit at least 50-fold selectivity for Nav 1.7 sodium channels over Nav 1.5 sodium channels, more preferably at least 500-fold selectivity for Nav 1.7 sodium channels over Nav 1.5 sodium channels when functional potency for each channel are compared using the IonWorks® assay technique described herein.

Compounds of the invention and formulations comprising compounds of the invention are believed to be useful in providing treatment, management, alleviation or amelioration of conditions or disease states which can be treated, managed, alleviated or ameliorated by specific inhibiting of Nav 1.7 channel activity. Examples of disease states which are believed to be desirably affected using such therapy include, but are not limited to, inhibiting acute pain, peri-operative, post-operative and neuropathic pain, for example, postherpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias, pruritus or cough.

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the Methyl group is emerging from the plane of the paper and the ethyl group is descending into the plane of the paper with the cyclohexene ring in the plane of the paper.

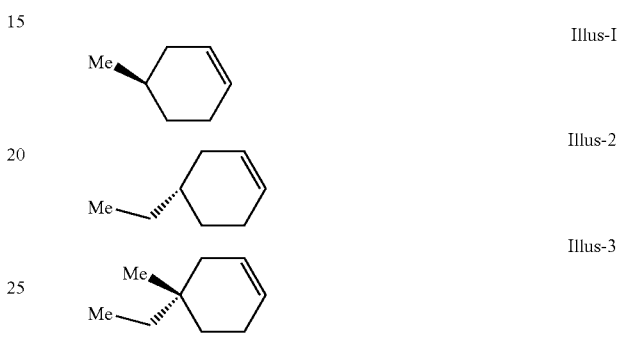

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents on a compound or moiety appended to the core structure of a compound means that one substituent of the group of substituents specified is present, and more than one substituent may be bonded to any of the chemically accessible bonding points of the core.

whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating central nervous system diseases or disorders with one or more of the compounds described herein "effective amount" (or "therapeutically effective amount") means, for example, providing the amount of at least one compound of Formula A that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula A to a compound of Formula A, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

The term "substituted" means that one or more of the enumerated substituents can occupy one or more of the bonding positions on the substrate typically occupied by "—H", provided that such substitution does not exceed the normal valency rules for the atom in the bonding configuration presented in the substrate, and that the substitution ultimately provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated substituents for the specified substrate can be present on the substrate in a bonding position normally occupied by the default substituent normally occupying that position. For example, a default substituent on the carbon atoms of an alkyl moiety is a hydrogen atom, an optional substituent can replace the default substituent.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, an "acyl" substituent may be equivalently described herein by the term "acyl", by typographical representations "R'—(C═O)—" or "R'—C(O)—", or by a structural representation:

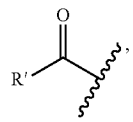

equally, with no differentiation implied using any or all of these representations;

alkyl" (including the alkyl portions of other moieties, such as trifluoromethyl-alkyl- and alkoxy-) means an aliphatic hydrocarbon moiety comprising up to about 20 carbon atoms (for example, a designation of "$C_{1-20}$-alkyl" indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms and may also be designated herein "$C_{1-8}$-alkyl". The term "alkyl" is further defined by "Linear", "Branched" or "Cyclic. Where the term "alkyl" is indicated with two hyphens (i.e., "-alkyl-" it indicates that the alkyl moiety is bonded in a manner that the alkyl moiety connects the substituents on either side of it, for example, "-alkyl-Cl" indicates an alkyl moiety connecting a chloride substituent to the moiety to which the alkyl is bonded on the other end.

The term "linear-alkyl" includes alkyl moieties which comprise a hydrocarbon chain with no aliphatic hydrocarbon "branches" appended to it, although other substituents may replace a C—H bond on the hydrocarbon chain. Examples of linear alkyl include, but are not limited to, methyl-, ethyl-, n-propyl-, n-butyl-, n-pentyl- or n-hexyl-.

The term "branched-alkyl" is a moiety comprising a main hydrocarbon chain of up to the maximum specified number of carbon atoms with a linear-, branched-, or cyclic-alkyl chain of up to 6 carbon atoms appended to one or more of the carbon atoms comprising, but not terminating, the main hydrocarbon chain. A branched alkyl moiety therefore comprises at least 3 carbon atoms in the main chain. Examples of branched alkyl moieties include, but are not limited to, t-butyl-, neopentyl-, or 2-methyl-4-ethyl-hexyl- The term "cyclic-alkyl" (equivalently "cycloalkyl") means a moiety having a main hydrocarbon chain forming a mono- or bicyclo-cyclic aliphatic moiety comprising at least 3 carbon atoms (the minimum number necessary to provide a monocyclic moiety) up to the maximum number of specified carbon atoms, generally 8 for a monocyclic moiety and 10 for a bicyclic moiety. Examples of cycloalkyl moieties include, but are not limited to, cyclopropyl, cyclobutyl, cyclopentyl or cyclohexyl. The term cyclic-alkyl (equivalently "cycloalkyl") also includes non-aromatic, fused multicyclic ring system comprising up to 20 carbon atoms which may optionally be substituted;

"aryl" (sometimes abbreviated "ar") means an aromatic monocyclic or multicyclic ring system comprising about 6 to about 14 carbon atoms (denoted herein also as "$C_{6-14}$-aryl"), preferably about 6 to about 10 carbon atoms ("$C_{6-10}$-aryl"); Non-limiting examples of suitable aryl groups include phenyl

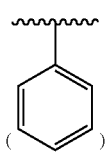

and naphthyl

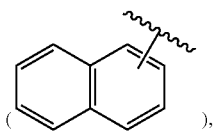

wherein bonding can be through any of the carbons in the aromatic ring, and wherein any ring carbon atoms not participating in a bond to the substrate may have bonded to it a substituent other than —H, independently selected in each instance from the list of "ring-system substituents" defined herein, or as defined in each instance where the term is used in conjunction with an enumerated list of substituents;

"halogen" means fluorine, chlorine, bromine, or iodine; preferred halogens, unless specified otherwise where the term is used, are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —CF$_3$;

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; the "heteroaryl" can be optionally substituted at chemically available ring atoms by one or more independently selected "ring system substituents" (defined below); the prefix aza, azo, oxa, oxo, thia or thio before the heteroaryl root name means that at least a nitrogen, oxygen or sulfur atom, respectively, is present as a ring atom, and in some embodiments 2 or more heteroatoms are present in a ring, for example, a pyrazole or a thiazole moiety; a nitrogen atom of a heteroaryl can be optionally oxidized to the corresponding N-oxide; non-limiting examples of heteroaryl moieties include: pyridyl-,

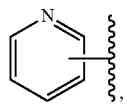

thiopenyl-,

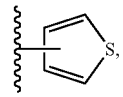

furanyl-,

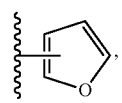

pyrazinyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, and, for example, heteroaryl moieties of the following structure (which are meant to exemplify, but not limit the definition):

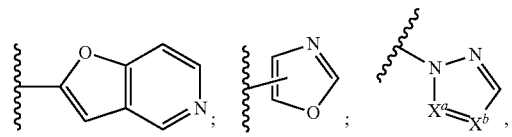

where one of $X^a$ or $X^b$ is —CH= or —N= and the other is —CH=, and, for example, heteroaryl moieties of the following structure:

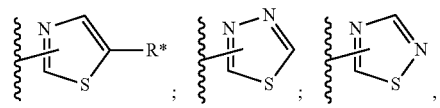

and the like, (unless otherwise indicated, such moieties may be bonded to the substrate through any available ring atom that results in a stable bonding arrangement);

"heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen (e.g. piperidyl- or pyrrolidinyl), oxygen (e.g. furanyl and tetrahydropyranyl) or sulfur (e.g. tetrahydrothiopheneyl and tetrahydrothiopyranyl); and wherein the heteroatoms can be alone or in combination provided that the moiety does not contain adjacent oxygen and/or sulfur atoms present in the ring system; preferred heterocyclyl moieties contain about 5 to about 6 ring atoms; the prefix aza, oxa or thia before the heterocyclyl root name means that at least one nitrogen, oxygen or sulfur atom, respectively, is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide (SO$_2$);

non-limiting examples of suitable monocyclic heterocyclyl rings include piperidyl, pyrrolidinyl, piperazinyl, morpholinyl—

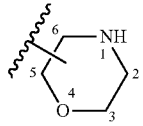

(where unless otherwise noted the moiety is bonded to the substrate through any of ring carbon atoms C2, C3, C5, or C6), thiomorpholinyl, thiazolidinyl, 1,3-dioxolanyl, 1,4-dioxanyl, tetrahydrofuranyl, tetrahydrothiophenyl, tetrahydrothiopyranyl, and the like; and polycyclicheterocyclyl compounds, for example, a bicyclo moiety of the structure:

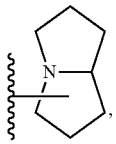

and a bridged, bicyclo moiety of the structure:

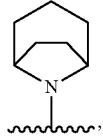

and the like.

"tetrahydropyranyl" moiety means a 6-member cyclic ether of the formula:

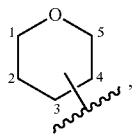

where, the bond line having an open end in the center of the structure and terminated at the other end with a wavy line indicates that the substituent is bonded to the substrate to which it is attached through any of carbon atoms 1 to 5, and wherein any of the bonding positions on carbons 1 to 5 normally occupied by a hydrogen atom, that is, the bonding positions on carbon atoms 1 to 5 which are not occupied by the bond to the substrate can optionally be occupied by specified or optional substituents;

bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

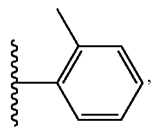

indicates that the methylphenyl moiety is bonded to a substrate through a carbon atom ortho to the methyl substituent, while a bond representation terminated with a wavy line and drawn into a structure without any particular indication of a atom to which it is bonded indicates that the moiety may be bonded to a substrate via any of the atoms in the moiety which are available for bonding as described in the examples above.

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.,* 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.,* 5(1), article 12 (2004); and A. L. Bingham et al, *Chem. Commun.,* 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

This invention also includes the compounds of this invention in isolated and purified form obtained by routine techniques. Polymorphic forms of the compounds of Formula A, and of the salts, solvates and prodrugs of the compounds of Formula A, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

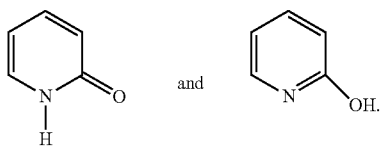 [SMILES: O=c1cccc[nH]1 ; Oc1ccccn1]

In some examples, compounds of the invention are presented herein which, for example, have a portion of their structure represented by either of the structural drawings A, shown below, contemplate including also the tautomeric form represented in structural drawing B:

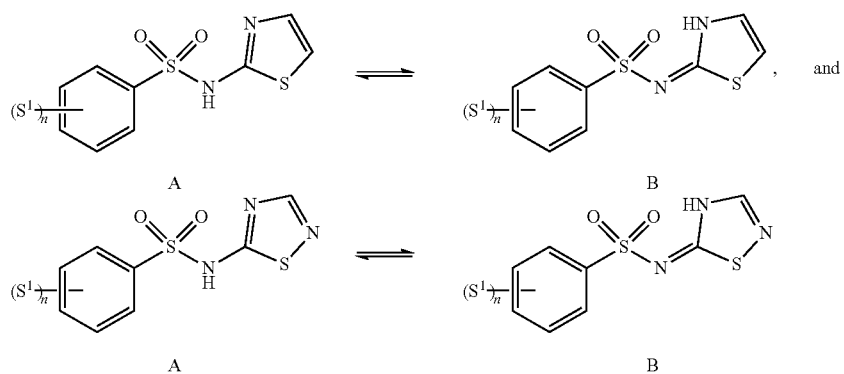

where $(S1)_n$ represents the various substituents which may be found on the aryl ring.

Where there are lone electron pairs having sufficient base character in a structure, for example, an oxygen atom which can be protonated or a nitrogen atom which can be quaternized, a structure represented with or without a cation coordinated to the lone pair contemplates both coordinated lone pair and uncoordinated lone pair, for example, the protonated form A and unprotonated form B of the amine illustrated below are both contemplated by either structural representation:

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al. The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

In general, salts of compounds are intended to be pharmaceutically acceptable salts within the scope of the invention and all acid and base salts are considered equivalent to the free forms of the corresponding compounds for purposes of the invention. Many of the compounds exemplified herein are isolated in the form of a hydrochloride, trifluoro acetate, or formate salt. As described in the Examples, herein, such salts may readily be converted to the free-base form of the compound by elution from an appropriate media using an appropriate base solution followed by chromatographic separation on a column of appropriate polarity.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups are known, for example, as by reference to standard textbooks, for example, T. W. Greene et al, Protective Groups in organic Synthesis (1991), Wiley, New York.

When a variable (e.g., aryl, cycloalkyl, $R^{XY}$, etc.) appears more than once in any moiety or in any compound of the invention, the selection of moieties defining that variable at each occurrence is independent of its definition at every other occurrence unless specified otherwise in the local variable definition.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, and $^{36}Cl$, $^{123}I$ and $^{125}I$. It will be appreciated that other isotopes may be incorporated by know means also.

Certain isotopically-labeled compounds of the invention (e.g., those labeled with $^{3}H$, $^{11}C$ and $^{14}C$) are recognized as being particularly useful in compound and/or substrate tissue distribution assays using a variety of known techniques. Tritiated (i.e., $^{3}H$) and carbon-14 (i.e., $^{14}C$) isotopes are particularly preferred for their ease of preparation and detection. Further, substitution of a naturally abundant isotope with a heavier isotope, for example, substitution of protium with deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

As used herein, the term "pharmaceutical composition" comprises at least one pharmaceutically active compound and at least one excipient, and is intended to encompass both the combination of the specified ingredients in the specified amounts, and any product which results, directly or indirectly, from combination of the specified ingredients in the specified amounts. As will be appreciated by the ordinarily skilled artisan, excipients are any constituent which adapts the composition to a particular route of administration or aids the processing of a composition into a dosage form without itself exerting an active pharmaceutical effect. A bulk composition is material that has not yet been formed into individual units for administration.

As mentioned above, in one aspect the invention provides compositions suitable for use in selectively inhibiting Nav 1.7 sodium channels found in sensory and sympathetic neurons, comprising at least one compound of the invention (as defined herein, for example one or more compounds of Formula A, or a salt thereof) and at least one pharmaceutically acceptable carrier (described below). It will be appreciated that pharmaceutical formulations of the invention may comprise more than one compound of the invention, for example, the combination of two or three compounds of the invention, each present by adding to the formulation the desired amount of the compound in a pharmaceutically acceptably pure form. It will be appreciated that compositions of the invention may comprise, in addition to one or more of the compounds of the invention, one or more additional compounds which also have pharmacological activity, for example, as described herein. Such formulations are believed to have utility in the treatment, management, amelioration or in providing therapy for diseases or conditions related to pain, for example, acute pain, chronic pain, inflammatory pain, or neuropathic pain disorders, or related to pruritic disorders, or cough disorders.

In one aspect this invention provides also pharmaceutical compositions which comprise in addition to at least one pharmaceutically acceptable carrier and an effective amount of at least one compound of the invention (e.g, a compound of Formula A or a salt thereof), an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP, acetaminophen), and a pharmaceutically acceptable carrier.

While compositions of the invention may be employed in bulk form, it will be appreciated that for most applications compositions will be incorporated into a dosage form suitable for administration to a patient, each dosage form comprising an amount of the selected composition which contains an effective amount of said one or more compounds of Formula A. Examples of suitable dosage forms include, but are not limited to, dosage forms adapted for: (i) intravenous (IV) infusion, for example, over a prolonged period using an I.V. infusion pump; (ii) a dosage form adapted for intramuscular administration (IM), for example, an injectable solution or suspension, and which may be adapted to form a depot having extended release properties; (iii) a dosage form adapted for drip intravenous administration (IV), for example, a solution or suspension, for example, as an IV solution or a concentrate to be injected into a saline IV bag; or (iv) a dosage form adapted for subcutaneous administration. Other dosage forms which may be contemplated include, but are not limited to: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for administration through tissues of the oral cavity, for example, a rapidly dissolving tablet, a lozenge, a solution, a gel, a sachets or a needle array suitable for providing intramucosal administration; (iii) a dosage form adapted for administration via the mucosa of the nasal or upper respiratory cavity, for example a solution, suspension or emulsion formulation for dispersion in the nose or airway; (iv) a dosage form adapted for transdermal administration, for example, a patch, cream or gel; (v) a dosage form adapted for intradermal administration, for example, a microneedle array; and (vi) a dosage form adapted for delivery via rectal or vaginal mucosa, for example, a suppository.

For preparing pharmaceutical compositions containing compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or for example, solution stabilizing or emulsifying agents which may adapt the formulation to a desired route of administration, for example, which provide a formulation for injection, for example, intramuscular or intravenous routes of administration or administration via IV or diffusion pump infusion or other form parenteral administration, or for oral administration, for example, via absorption from the gastrointestinal tract, or for transdermal or transmucosal administration, for example, via adhesive skin "patch" or buccal administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, minitablets, beads, which can be used, for example, for tableting, encapsulation, or direct administration. Liquid form preparations include, but are not limited to, solutions, suspensions and emulsions which for example, but not exclusively, can be employed in the preparation of formulations intended for intravenous administration (IV), for example, but not limited to, administration via drip IV or infusion pump, intramuscular injection (IM), for example, of a bolus which is released over an extended duration, direct IV injection, or adapted to subcutaneous routes of administration. Other routes of administration which may be contemplated include intranasal administration, or for administration to some other mucosal membrane. Formulations prepared for administration to various mucosal membranes may also include additional components adapting them for such administration, for example, viscosity modifiers.

Although in some embodiments, compositions suitable for use in an IV administration, for example, IV drip or infusion pump or injection, or for subcutaneous routes of administration are preferable, a composition of the invention may be formulated for administration via other routes. Examples include aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

For example, the compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, $20^{th}$ Edition, (2000), Lippincott Williams & Wilkins, Baltimore, Md.

The actual dosage employed may be varied depending upon the requirements of the patient and the severity of the condition being treated. Determination of the proper dosage regimen for a particular situation is within the skill in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56th Edition, 2002 (published by Medical Economics company, Inc. Montvale, N.J. 07645-1742), or the Physician's Desk Reference, 57th Edition, 2003 (published by Thompson P D R, Montvale, N.J. 07645-1742); the disclosures of which is incorporated herein by reference thereto. For convenience, the total daily dosage may be divided and administered in portions during the day as required or delivered continuously.

In general, in whatever form administered, the dosage form administered will contain an amount of at least one compound of the invention, or a salt thereof, which will provide a therapeutically effective serum level of the compound meeting or exceeding the minimum therapeutically effective serum level on a continuous basis throughout the period during which treatment is administered. As mentioned above, a composition of the invention can incorporate additional pharmaceutically active components or be administered simultaneously, contemporaneously, or sequentially with other pharmaceutically active compositions as may be additionally needed in the course of providing treatment.

In another embodiment the present invention is believed to provide for treatment, management, prevention, alleviation or amelioration of conditions or disease states which can be treated, managed, prevented, alleviated or ameliorated by specific inhibition of Nav 1.7 channel activity. Some examples are pain conditions, pruritic conditions and cough conditions. Examples of pain conditions include, but are not limited to, acute pain, perioperative pain, preoperative pain, postoperative pain, neuropathic pain, for example, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with cancer and chemotherapy, pain associated with HIV, and HIV treatment-induced neuropathy, nerve injury, root avulsions, painful traumatic mononeuropathy, painful polyneuropathy, erythromyelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmenorrhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain, pruritic conditions, and cough conditions.

In some embodiments in which it is desired to treat a pain disorder, preferably the disorder is acute pain, peri-operative pain, post-operative pain, inflammatory pain or neuropathic pain, more preferably the disorder is acute pain, peri-operative pain or post-operative pain.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during the treatment cycle.

Those skilled in the art will appreciate that treatment protocols utilizing at least one compound of the invention can be varied according to the needs of the patient. Thus, compounds of the invention used in the methods of the invention can be administered in variations of the protocols described herein.

As mentioned above, the invention provides compounds believed to have selective activity as $Na_v$ 1.7 Sodium Ion channel blockers which have the structure of Formula A, or a salt thereof:

Formula A, or a salt thereof:

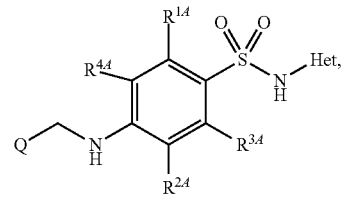

Formula A wherein Q, $R^{1A}$ to $R^{4A}$, and Het are defined herein.

In some embodiments, a compound of Formula A is preferably a compound of the Formula:

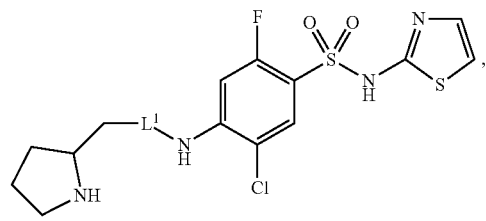

or a salt thereof, wherein:

$L^1$ is:

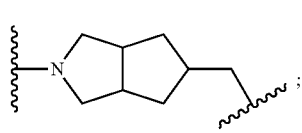

(i)

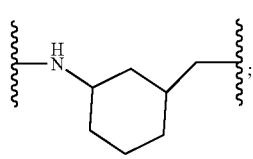

(ii)

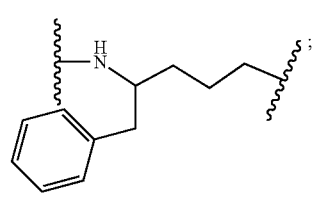

(iii)

-continued (iv)
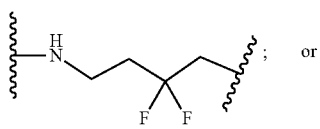
or (v)
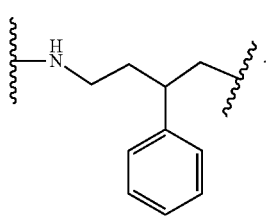

In some embodiments, the compound of Formula A is preferably a compound of the formula:

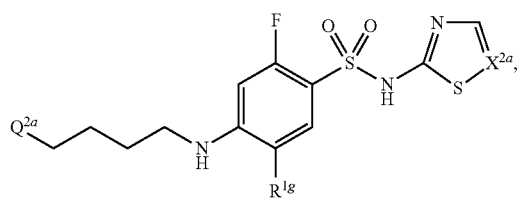

or a salt thereof,
wherein
$X^{2a}$ is —N=, —CH=, or —CF=;
$R^{1g}$ is —Cl or —Br; and
$Q^2a$ is:
(i) a heterocycl of the formula:

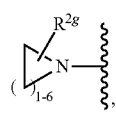

where $R^{2g}$ is optionally bonded to any carbon at any available position and is independently for each occurrence: (ai) —CH$_2$—NH$_2$; (aii) —NH—CH$_3$; (aiii) aryl; or (aiv) —NH$_2$;
(ii) a heterocycl of the formula:

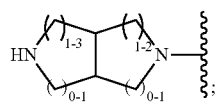

(iii) a heterocycl of the formula:

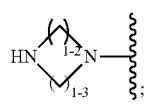

(iv) a heterocycl of the formula:

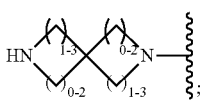

or
(v) a heterocycl of the formula:

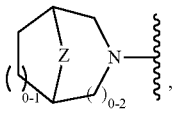

wherein Z is: —NH—; CR$^{3g}$H—, wherein $R^{3g}$ is —H or —NH$_2$; or a bond.

In some embodiments, the compound of Formula A is preferably a compound of the formula:

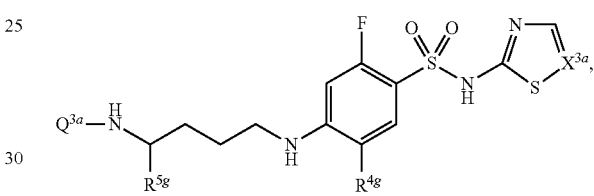

or a salt thereof,
wherein:
$R^{4g}$ is —Cl or —Br;
$R^{5g}$ is —H or —CH$_3$;
$X^{3a}$ is:
N=; or
—C(R$^{6g}$)=, wherein $R^{6g}$ is: (i) —H; (ii) —CH$_3$; (iii) —Cl; or (iv) —F; and
$Q^{3a}$ is:
(a) a bridged heterocycl comprising a central ring of at least one nitrogen atom and up to 7 carbon atoms, and wherein a linear or branched alkyl of up to 3 carbon atoms forms a "bridge" between any two non-adjacent ring carbon atoms, and wherein said heterocycle is bonded to the nitrogen via any carbon atom therein which is not adjacent to a heteroatom therein, in some embodiments said bridged heterocycle is preferably a moiety of the formula:

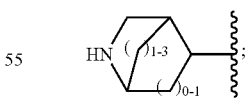

(b) a heterocycle comprising at least one nitrogen atom and up to 6 carbon atoms which is substituted on at least one carbon thereof with aryl, and which is bonded via a carbon atom that is not adjacent to a ring heteroatom;
(c) a linear, branched or cyclic alkyl which is substituted on at least one carbon atom thereof with: (ai) —F; (aii) aryl; (aiii) tetrahydropyranyl; or (aiv) benzyl, and on another carbon atom thereof is substituted with (R$^{7g}$)$_2$N—, wherein R$^{7g}$ is independently —H, or lower alkyl;

(d) a linear or branched alkyl of up to 5 carbon atoms which is substituted on at least one carbon thereof with:
  (i) a heterocycl bonded via any available ring carbon atom, said heterocycl comprising a ring of up to 6 carbon atoms and at least one nitrogen atom, which said heterocycl is substituted on at least one ring carbon atom with:
    (ai) aryl which is optionally substituted with a linear-, branched- or cyclic-alkoxy of up to 6 carbon atoms;
    (aii) —F;
    (aiii) —O-aryl;
    (aiv) —O-alkyl;
    (av) —CN;
    (avi) benzyl which is optionally substituted on any available ring carbon with a linear-, branched- or cyclic-alkoxy of up to 6 carbon atoms;
  (ii) $R^{8g}$—NH—, wherein $R^{8g}$ is:
    (ai) aryl;
    (aii) benzyl;
    (aiii) adamantyl; or
    (aiv) tetrahydropyran.
(e) $R^{9g}$—NH—$(C(R^{10g})_2)_{2-4}$—, wherein:
  at least one $R^{10g}$ is —F, aryl, or —CN, and the others of $R^{10g}$ are independently —H, —F, aryl, benzyl, or lower alkyl; and
  $R^{9g}$ is:
    (ai) —H; or
    (aii) a linear, branched or cyclic alkyl of up to 6 carbon atoms which is optionally substituted on one or more carbon atoms thereof with —F.

In the examples that follow certain of the exemplified compounds, or salts thereof, are prepared as pure enantiomers, or prepared from enantiopure precursors, or are isolated using chiral separation methods after synthesis, for example, chiral chromatography. After isolation of chiral compounds the absolute stereochemistry of the isolated compound was not determined in every example. Accordingly, where pure isomers have been prepared but the absolute configuration has not been verified, the enantiomer isolated in pure form is specified by the following convention.

Unless indicated otherwise in the text, where present, isomers of example compounds were not separated. Unless indicated otherwise in the text, where isomers were separated into fractions containing an excess of a particular isomer, for example, a fraction containing an excess of an optical isomer, which separation may be accomplished, for example, by super critical fluid chromatography, absolute stereochemistry of separated isomers was not determined unless indicated otherwise.

Where a reaction scheme appearing in an example employs a compound having one or more stereocenters, the stereocenters are indicated with an asterisk, as shown below in illustration compound Def-1.

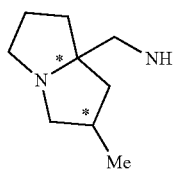

Def-1

Accordingly, Def-1 consists of the following pairs of isomers: (i) Trans-isomers ((2R,7aS)-2-methylhexahydro-1H-pyrrolizin-7a-yl)methanamine (Compound ABC-1) and ((2S,7aR)-2-methylhexahydro-1H-pyrrolizin-7a-yl)methanamine (Compound ABC-2); and (ii) Cis-isomers ((2R,7aR)-2-methylhexahydro-1H-pyrrolizin-7a-yl)methanamine (Compound ABC-3) and ((2S,7aS)-2-methylhexahydro-1H-pyrrolizin-7a-yl)methanamine (Compound ABC-4).

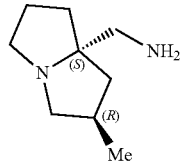

ABC-1

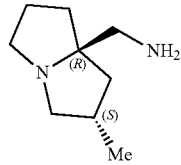

ABC-2

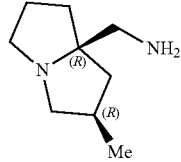

ABC-3

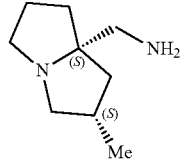

ABC-4

When the compound is prepared and separated into pure enantiomers, albeit without determining the absolute configuration of each enantiomer of the compound, the product will be identified in the title using both enantiomer names, e.g., where ABC-1 and ABC-2 are prepared and separated into pure enantiomers, the title will read "preparation of ((2R,7aS)-2-methylhexahydro-1H-pyrrolizin-7a-yl)methanamine and ((2S,7aR)-2-methylhexahydro-1H-pyrrolizin-7a-yl)methanamine. In some instances where enantiomeric compounds are prepared the designation (Cis) or (Trans) may be appended to the name to clarify the relationship of the stereo centers present in the two stereoisomers. As will be appreciated, identification of each product in the experimental preparation as "ABC-enantiomer A" or "ABC-enantiomer B" is not an association of the enantiomer prepared and isolated with any stereospecific name, only that both said enantiomers were prepared and isolated in increased enantiopurity without determination of the absolute configuration of either compound thus prepared.

Where isomeric compounds are prepared in a racemic mixture, asterisks will be inserted into the structural representation to indicate the stereocenters, but the title will reference the preparation of both enantiomers, e.g., where ABC-3 and ABC-4 are prepared as a racemate, the title will read "preparation of ((2R,7aR and 2S,7aS)-2-methylhexahydro-1H-pyrrolizin-7a-yl)methanamine".

The following examples are presented to further illustrate compounds of the invention, but, with reference to the general formula presented above, they are not presented as limiting the invention to these specifically exemplified compounds.

Examples

Examples of the preparation of compounds of the invention are shown next. In each of the Examples, the identity of the compounds prepared were confirmed by a variety of techniques. In all cases the compounds were analyzed by LC/MS or HPLC.

In many of the examples, isolation of the compound is accomplished by a chromatographic technique which results in the isolation of a salt of the compound, for example, an acetate, trifluoroacetate, hydrochloride, or formate salt. It will be appreciated that the free-base of the compound may be prepared from such a salt form by ordinary techniques, for example, as shown in the following scheme.

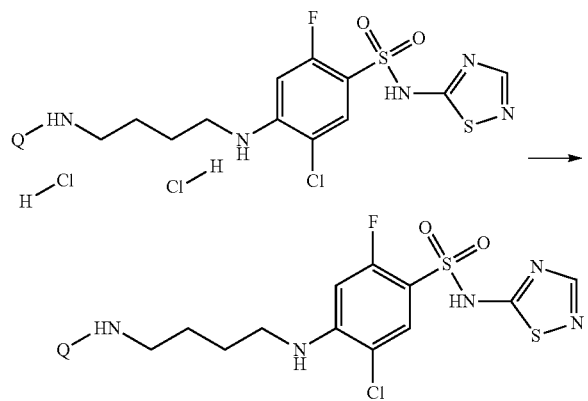

An aliquot of the salt is dissolved in a suitable quantity of a suitable solvent, for example, 500 mg of salt in 10 mL of methanol (MeOH). The solution is loaded onto a suitable substrate, for example, a Discovery DSC-SCX (polymerically bonded benzene sulfonic acid group on silica support) 10 g plug. The loaded plug is eluted with a suitable solvent to wash the plug upon which the compound was absorbed, for example, washed with a suitable quantity of MeOH. After washing the plug is eluted with with a suitable base, for example, 2N $NH_3$ in MeOH and the eluent is collected and concentrated to precipitate a solid material.

Thus obtained, the solid is dissolve in a suitably polar solvent, for example, water/DMSO, and the solution loaded onto a column of suitable polarity, for example, a 275 g C18 column. The loaded column is eluted with 0-100% acetonitrile (AcCN) in water and the fractions containing the desired freebase compound are collected, and the collected fractions containing freebase compound are lyophylize to isolate the solid freebase form of the compound.

Where utilized, Prep HPLC was carried out on a Gilson 281 equipped with a Phenomenexd Synergi C18, 100 mm×21.2 mm×5 micron column. Conditions included a flow rate of 25 mL/min., eluted with a 0-40% acetonitrile/water eluent comprising 0.1% v/v TFA.

LC/MS determinations used either an Agilent YMC J'Sphere H-80 (3×50 mm) 5 m column using mobile phase containing A: 0.1% Trifluoroacetic acid in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer or an Agilent TC-C18 (2.1×50 mm) 5 m column using mobile phase containing A: 0.0375% Trifluoroacetic acid in water and B: 0.01875% Trifluoroacetic acid in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

For some compounds, the identity of the compound was verified by proton NMR and high-resolution MS. Proton NMR was were acquired using a Varian Unity-Inova 400 MHz NMR spectrometer equipped with a either a Varian 400 ATB PFG 5 mm, Nalorac DBG 400-5 or a Nalorac IDG 400-5 probe in accordance with standard analytical techniques, unless specified otherwise, and results of spectral analysis are reported.

High resolving power accurate mass measurements were acquired by use of a Bruker Daltonics 7T Fourier transform ion cyclotron resonance (FTICR) mass spectrometer. Samples were dissolved in acetonitrile:water:acetic acid (50:50:0.1% v/v), and ionized by use of electrospray ionization (ESI) yielding [M+H]+ and/or [M+Na]+. External calibration was accomplished with oligomers of polypropylene glycol (PPG, average molecular weight 1000 Da).

Throughout the Examples section, the following abbreviations are used to indicate various reagents, substituents and solvents: AcCN=acetonitrile; AcOH=acetic acid; Boc=tert-butoxycarbonyl; $Boc_2O$=di-tert-butyl carbonate; Bn=Benzyl; DABCO=1,4-diazabicyclo[2.2.2]octane; DAST=diethylaminosulfur trifluoride; DCE=dichloroethane; DCM=dichloromethane; DEAD=diethylazodicarboxylate; DIPEA=diisopropylamine; DMAP=4-dimethylaminopyridine; DMB (2,4-dimethoxybenzyl-); DMF=dimethylformamide; DMP=Dess-Martin Periodinane; DMS=dimethylsulfide; DMSO=dimethylsulfoxide; DPPA=diphenylphosphoryl azide; dppf=1,1'-bis(diphenylphosphino)ferrocene; EtOAc=ethyl acetate; EtOH=ethanol; Fmoc=fluorenyloxycarbonyl; HATU=1-[Bis (dimethylamino)methylene]-1H-1,2,3-triazolo[4,5-b]pyridinium-3-oxide-hexafluorophosphate; Hex=hexanes; HMPA=hexamethylphosphoramide; HPLC=high-performance liquid chromatography; IPA=isopropyl alcohol; LC/MS=liquid chromatography/mass spectrometry; LDA=lithium diisopropylamide; LG=leaving group; LiHMDS=lithium bis(trimethylsilyl)amide; MeOH=methanol; LRMS=low resolution mass spectrometry; MOM=methoxymethyl; MOMCl=methyl chloromethyl ether; MsCl=methanesulfonyl chloride; NMP=N-methylpyrrolidone; Pd/C=palladium on carbon; $Pd_2(dba)_3$=tris(dibenzylideneacetone)dipalladium(0); PE=petroleum ether; PG=protecting group; PMP=para-methoxybenzyl; PMBCl=para-methoxybenzyl chloride; Prep-TLC=preparative thin layer chromatography; Py=pyridine; Selectfluor=1-(chloromethyl)-4-fluoro-1,4-diazoniabicyclo[2.2.2]octane ditetrafluoroborate; SFC=Supercritical Fluid Chromatography; TBS=tert-butyldimethylsilyl; TBS-Cl=tert-butyldimethylsilyl chloride; THF=Tetrahydrofuran; TFA=trifluoroacetic acid; TFAA=trifluoroacetic acid anhydride; TsOH=para-toluenesulfonic acid; UV=ultraviolet; Xantphos=4,5-Bis(diphenylphosphino)-9,9-dimethylxanthene.

Example 1: 4-[(4-{[2-(benzylamino)ethyl]amino}butyl)amino]-5-chloro-2-fluoro-N-1,3-thiazol-2-ylbenzenesulfonamide (1-3)

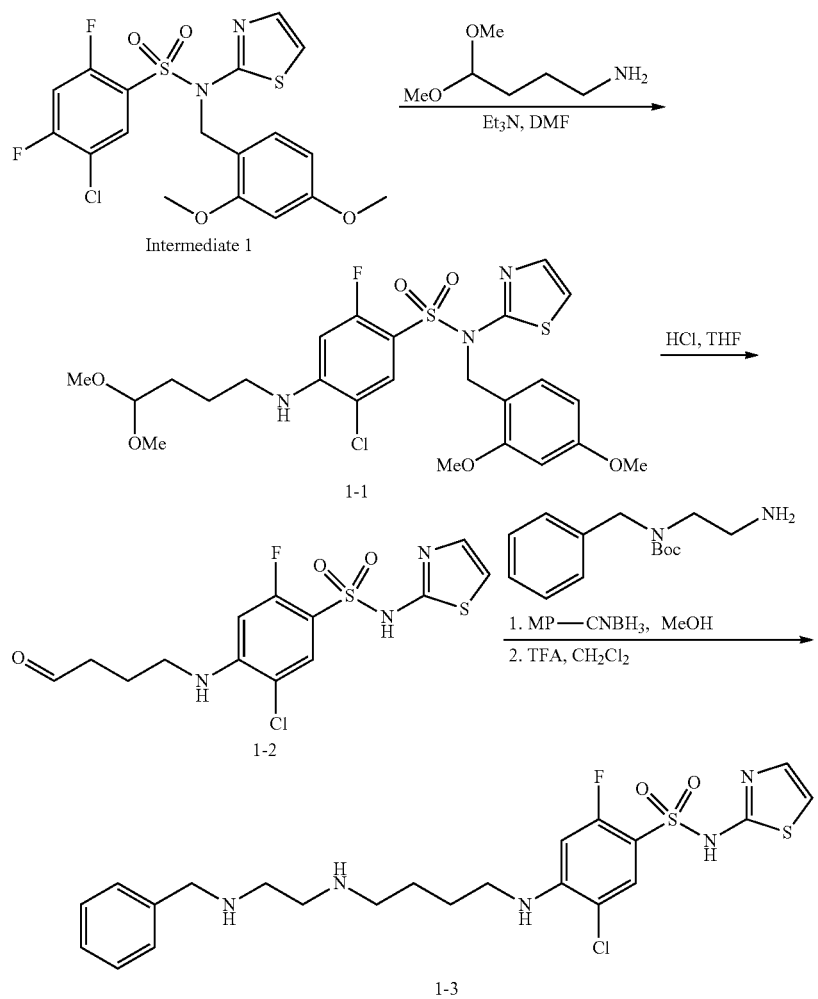

5-chloro-N-(2,4-dimethoxybenzyl)-4-((4,4-dimethoxybutyl)amino)-2-fluoro-N-(thiazol-2-yl)benzenesulfonamide (1-1)

To a solution of Intermediate 1 (5.00 g, 10.8 mmol) in DMF (31 ml) at room temperature was added 4-aminobutyraldehyde dimethyl acetal (1.81 g, 13.6 mmol) and Et$_3$N (4.5 ml, 32 mmol). The mixture was stirred at room temperature 3 h. The resulting mixture was quenched with 10% aq NaCl and extracted with ethyl acetate (2×). The combined extracts were washed with 10% aq NaCl (2×), dried with Na$_2$SO$_4$, filtered and concentrated. The mixture was then purified by isco silica gel chromatography (120 g RediSep Rf silica gel column, 0-50% ethyl acetate/hexanes) to give the desired product. LRMS m/z (M+H) 574.1 found, 574.1 calc'd.

5-chloro-2-fluoro-4-((4-oxobutyl)amino)-N-(thiazol-2-yl)benzenesulfonamide (1-2)

To a solution of 1-1 (5.75 g, 10.0 mmol) in THF (100 ml) at room temperature was added 2 N HCl (50 ml, 100 mmol). The mixture was stirred at room temperature 1 h. The reaction was quenched with water and extracted with DCM. The combined organic extracts were dried over Na$_2$SO$_4$, filtered and concentrated. The mixture was then purified by isco silica gel chromatography (120 g RediSep Rf silica gel column, 0-50% ethyl acetate/hexanes) to give the desired product. LRMS m/z (M+H) 378.0 found, 378.0 calc'd.

4-[(4-{[2-(benzylamino)ethyl]amino}butyl)amino]-5-chloro-2-fluoro-N-1,3-thiazol-2-ylbenzenesulfonamide (1-3)

To a solution of 1-2 (100 mg, 0.265 mmol) in MeOH (2.5 mL) was added tert-butyl (2-aminoethyl)(benzyl)carbamate (330 mg, 1.32 mmol) and MgSO$_4$. The reaction was stirred for 12 h at room temperature, followed by the addition of MP-cyanoborohydride (0.794 mmol). The reaction was stirred for an additional 30 min, filtered, and concentrated. The mixture was then dissolved in a 1:1 solution of DCM:TFA (5 mL), stirred for 30 min, and concentrated. The mixture was then purified by prep-HPLC to give the desired product. $^1$H NMR (499 MHz, DMSO): δ 7.59 (d, J=7.0 Hz, 1H); 7.46-7.48 (m, 6H); 7.28 (d, J=4.7 Hz, 1H); 6.84 (d, J=4.7 Hz, 1H); 6.67 (d, J=12.8 Hz, 1H); 6.46 (s, 1H); 4.20 (s, 2H); 3.23 (s, 2H); 2.98 (s, 2H); 1.58 (s, 4H). LRMS m/z (M+H) 512.3 found, 512.1 calc'd.

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE I

| Example | Structure | IUPAC Name | LC/MS [M + H]+ |
| --- | --- | --- | --- |
| 1-8 | 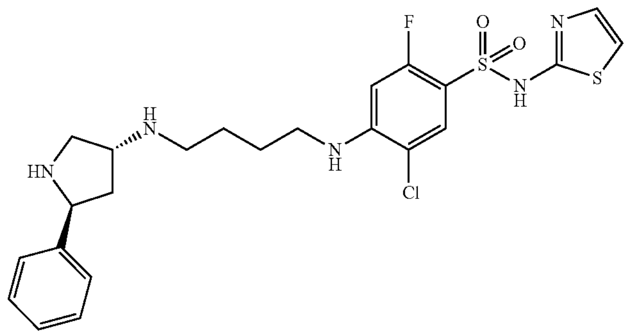 [SMILES: O=S(=O)(Nc1nccs1)c1cc(Cl)c(NCCCCN[C@H]2CN[C@H](c3ccccc3)C2)cc1F] | 5-chloro-2-fluoro-4-[(4-{[(3R,5S)-5-phenylpyrrolidin-3-yl]amino}butyl)amino]-N-1,3-thiazol-2-ylbenzenesulfonamide | Calc'd 524.1, found 524.3 |
| 1-9 | 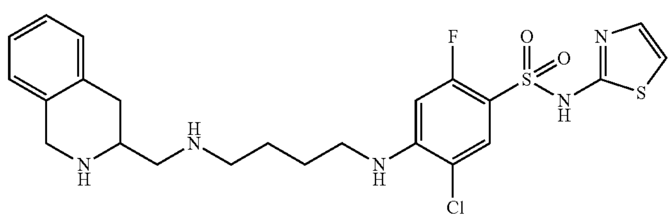 [SMILES: O=S(=O)(Nc1nccs1)c1cc(Cl)c(NCCCCNCC2Cc3ccccc3CN2)cc1F] | 5-chloro-2-fluoro-4-({4-[(1,2,3,4-tetrahydroisoquinolin-3-ylmethyl)amino]butyl}amino)-N-1,3-thiazol-2-ylbenzenesulfonamide | Calc'd 524.1, found 524.3 |
| 1-11 | 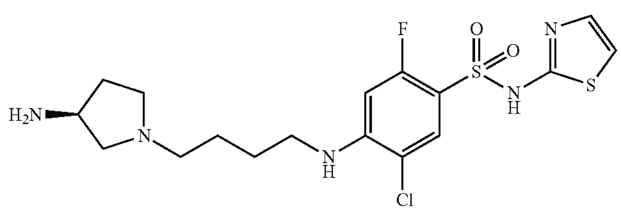 [SMILES: N[C@H]1CCN(CCCCNc2cc(F)c(S(=O)(=O)Nc3nccs3)cc2Cl)C1] | 4-({4-[(3S)-3-aminopyrrolidin-1-yl]butyl}amino)-5-chloro-2-fluoro-N-1,3-thiazol-2-ylbenzenesulfonamide | Calc'd 448.1, found 448.3 |
| 1-12 | 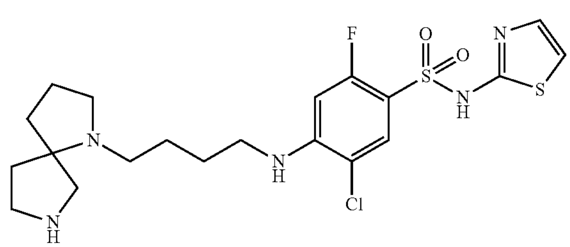 [SMILES: O=S(=O)(Nc1nccs1)c1cc(Cl)c(NCCCCN2CCCC23CCNC3)cc1F] | 5-chloro-4-{[4-(1,7-diazaspiro[4.4]non-1-yl)butyl]amino}-2-fluoro-N-1,3-thiazol-2-ylbenzenesulfonamide | Calc'd 488.1, found 488.3 |
| 1-13 | 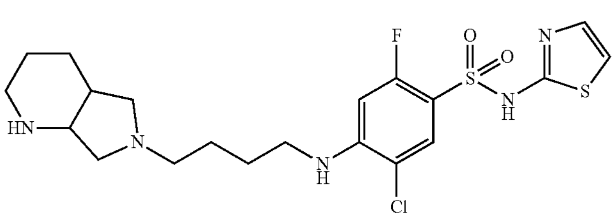 [SMILES: O=S(=O)(Nc1nccs1)c1cc(Cl)c(NCCCCN2CC3CCCNC3C2)cc1F] | 5-chloro-2-fluoro-4-{[4-(octahydro-6H-pyrrolo[3,4-b]pyridin-6-yl)butyl]amino}-N-1,3-thiazol-2-ylbenzenesulfonamide | Calc'd 488.1, found 488.3 |

TABLE I-continued

| Example | Structure | IUPAC Name | LC/MS [M + H]+ |
|---|---|---|---|
| 1-14 | 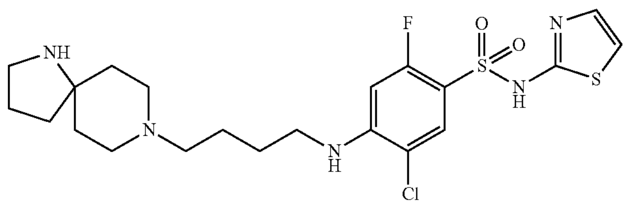 [SMILES: O=S(=O)(Nc1nccs1)c1cc(Cl)c(NCCCCN2CCC3(CCCN3)CC2)cc1F] | 5-chloro-4-{[4-(1,8-diazaspiro[4.5]dec-8-yl)butyl]amino}-2-fluoro-N-1,3-thiazol-2-ylbenzenesulfonamide | Calc'd 502.2, found 502.3 |
| 1-16 A | 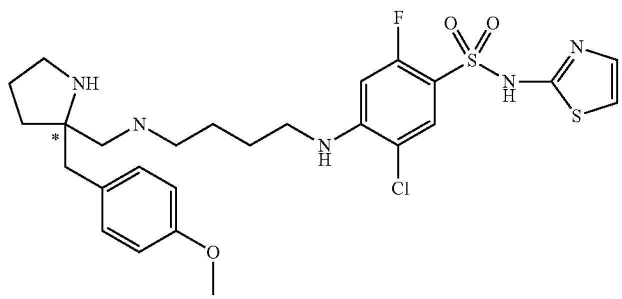 [SMILES: COc1ccc(CC2(CNCCCCNc3cc(F)c(S(=O)(=O)Nc4nccs4)cc3Cl)CCCN2)cc1] | (S or R)-5-chloro-2-fluoro-4-{[4-({[2-(4-methoxybenzyl)pyrrolidin-2-yl]methyl}amino)butyl]amino}-N-1,3-thiazol-2-ylbenzenesulfonamide | Calc'd 582.2, found 582.2 |
| 1-16 B | 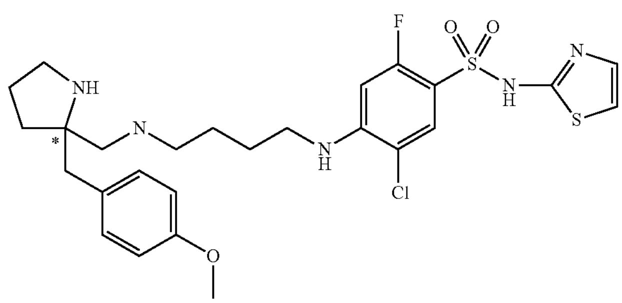 [SMILES: COc1ccc(CC2(CNCCCCNc3cc(F)c(S(=O)(=O)Nc4nccs4)cc3Cl)CCCN2)cc1] | (R or S)-5-chloro-2-fluoro-4-{[4-({[2-(4-methoxybenzyl)pyrrolidin-2-yl]methyl}amino)butyl]amino}-N-1,3-thiazol-2-ylbenzenesulfonamide | Calc'd 582.2, found 582.2 |
| 1-17 | 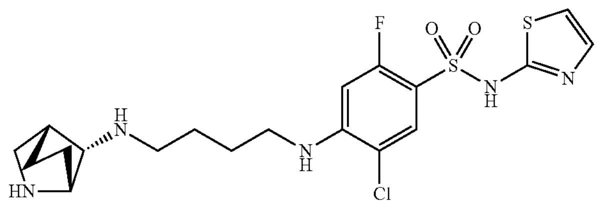 [SMILES: O=S(=O)(Nc1nccs1)c1cc(Cl)c(NCCCCN[C@H]2[C@@H]3CC[C@H]2NC3)cc1F] | 4-({4-[(1R,4R,7S)-2-azabicyclo[2.2.1]hept-7-ylamino]butyl}amino)-5-chloro-2-fluoro-N-1,3-thiazol-2-ylbenzenesulfonamide | Calc'd 474.1, found 474.1 |
| 1-18 | 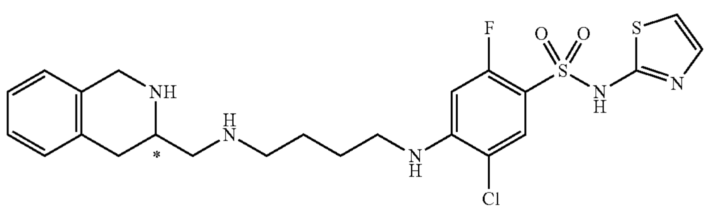 [SMILES: O=S(=O)(Nc1nccs1)c1cc(Cl)c(NCCCCNCC2Cc3ccccc3CN2)cc1F] | (R or S)-5-chloro-2-fluoro-4-({4-[(1,2,3,4-tetrahydroisoquinolin-3-ylmethyl)amino]butyl}amino)-N-1,3-thiazol-2-ylbenzenesulfonamide | Calc'd 524.1, found 524.1 |
| 1-19 | 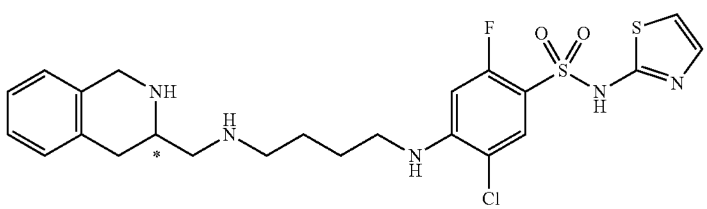 [SMILES: O=S(=O)(Nc1nccs1)c1cc(Cl)c(NCCCCNCC2Cc3ccccc3CN2)cc1F] | (S or R)-5-chloro-2-fluoro-4-({4-[(1,2,3,4-tetrahydroisoquinolin-3-ylmethyl)amino]butyl}amino)-N-1,3-thiazol-2-ylbenzenesulfonamide | Calc'd 524.1, found 524.1 |

TABLE I-continued

| Example | Structure | IUPAC Name | LC/MS [M + H]+ |
|---|---|---|---|
| 1-20 | 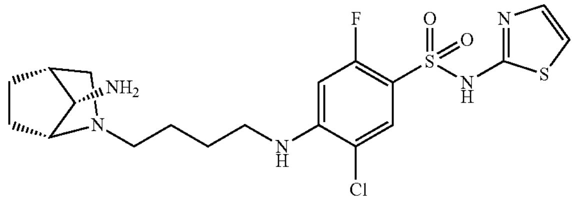 [SMILES: N[C@H]1[C@@H]2CC[C@H]1N(CCCCNc1cc(F)c(S(=O)(=O)Nc3nccs3)cc1Cl)C2] | 4-({4-[(1R,4R,7S)-7-amino-2-azabicyclo[2.2.1]hept-2-yl]butyl}amino)-5-chloro-2-fluoro-N-1,3-thiazol-2-ylbenzenesulfonamide | Calc'd 474.1, found 474.11 |
| 1-21 | 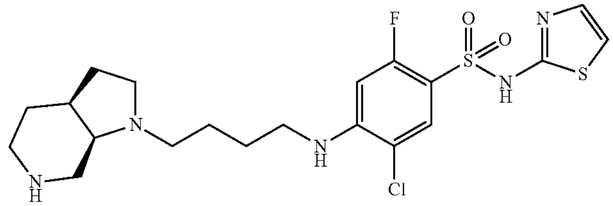 [SMILES: O=S(=O)(Nc1nccs1)c1cc(Cl)c(NCCCCN2CC[C@@H]3CCNC[C@@H]32)cc1F] | 5-chloro-2-fluoro-4-({4-[(3aS,7aR)-octahydro-1H-pyrrolo[2,3-c]pyridin-1-yl]butyl}amino)-N-1,3-thiazol-2-ylbenzenesulfonamide | Cal'd 488.1, found 484.13 |
| 1-22 | 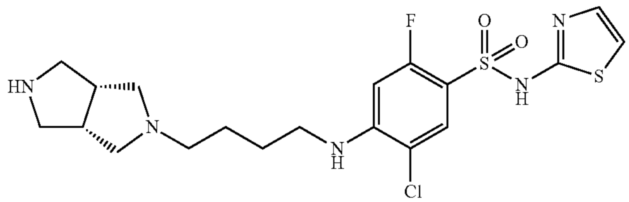 [SMILES: O=S(=O)(Nc1nccs1)c1cc(Cl)c(NCCCCN2C[C@H]3CNC[C@H]3C2)cc1F] | 5-chloro-2-fluoro-4-({4-[(3aR,6aS)-hexahydropyrrolo[3,4-c]pyrrol-2(1H)-yl]butyl}amino)-N-1,3-thiazol-2-ylbenzenesulfonamide | Cal'd 474.1, found 474.11 |
| 1-23 | 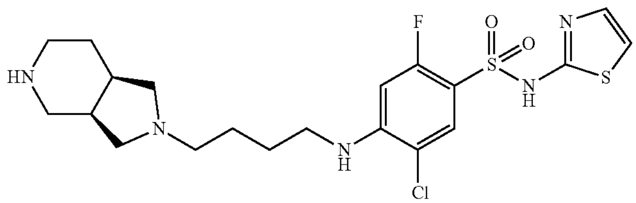 [SMILES: O=S(=O)(Nc1nccs1)c1cc(Cl)c(NCCCCN2C[C@H]3CNCC[C@H]3C2)cc1F] | 5-chloro-2-fluoro-4-({4-[(3aR,7aR)-octahydro-2H-pyrrolo[3,4-c]pyridin-2-yl]butyl}amino)-N-1,3-thiazol-2-ylbenzenesulfonamide | Calc'd 488.1, found 488.13 |
| 1-24 | 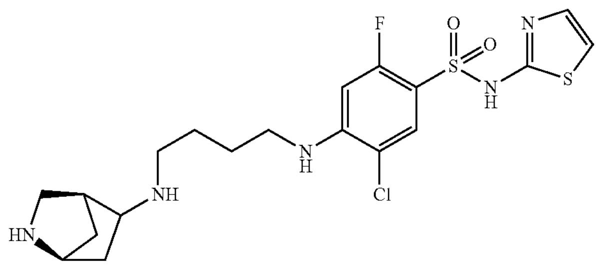 [SMILES: O=S(=O)(Nc1nccs1)c1cc(Cl)c(NCCCCNC2C[C@@H]3C[C@H]2CN3)cc1F] | 4-({4-[(1S,4S)-2-azabicyclo[2.2.1]hept-5-ylamino]butyl}amino)-5-chloro-2-fluoro-N-1,3-thiazol-2-ylbenzenesulfonamide | Calc'd 474.1, found 474.11 |
| 1-25 | 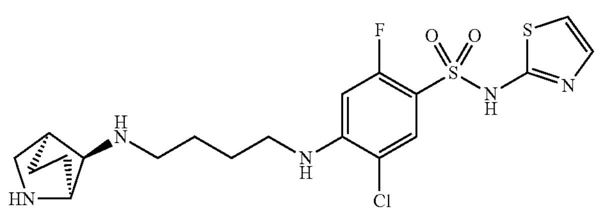 [SMILES: O=S(=O)(Nc1nccs1)c1cc(Cl)c(NCCCCN[C@@H]2[C@H]3CC[C@@H]2NC3)cc1F] | 4-({4-[(1S,4S,7R)-2-azabicyclo[2.2.1]hept-7-ylamino]butyl}amino)-5-chloro-2-fluoro-N-1,3-thiazol-2-ylbenzenesulfonamide | Calc'd 474.1, found 474.1 |
| 1-26 | 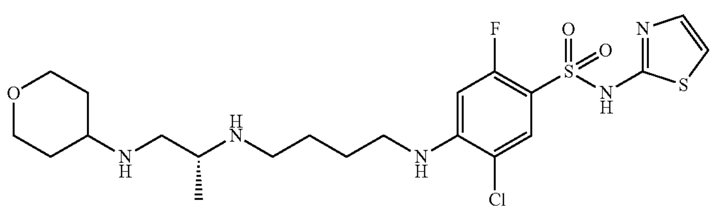 [SMILES: C[C@H](CNC1CCOCC1)NCCCCNc1cc(F)c(S(=O)(=O)Nc2nccs2)cc1Cl] | 5-chloro-2-fluoro-4-[(4-{[(1R)-1-methyl-2-(tetrahydro-2H-pyran-4-ylamino)ethyl]amino}butyl)amino]-N-1,3-thiazol-2-ylbenzenesulfonamide | Calc'd 520.2, found 520.3 |

TABLE I-continued

| Example | Structure | IUPAC Name | LC/MS [M + H]+ |
|---|---|---|---|
| 1-31 | 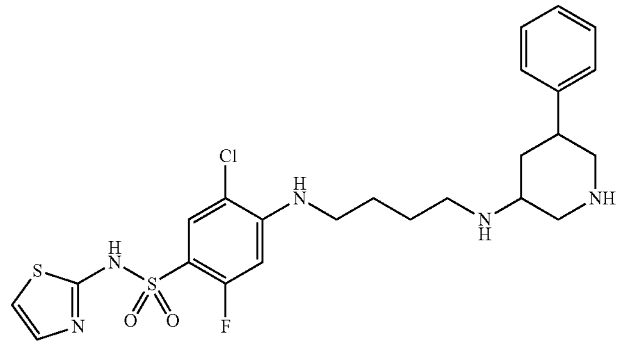 [SMILES: O=S(=O)(Nc1nccs1)c1cc(Cl)c(NCCCCNC2CNCC(c3ccccc3)C2)cc1F] | 5-chloro-2-fluoro-4-({4-[(5-phenylpiperidin-3-yl)amino]butyl}amino)-N-1,3-thiazol-2-ylbenzenesulfonamide | Calc'd 538.2, found 538.3 |
| 1-32 | 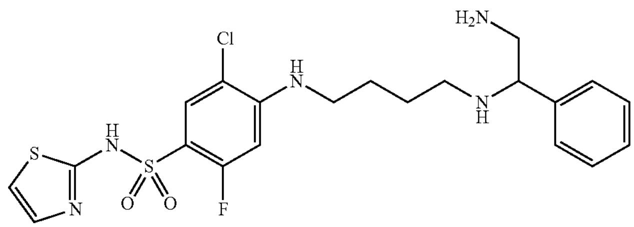 [SMILES: NCC(NCCCCNc1cc(F)c(S(=O)(=O)Nc2nccs2)cc1Cl)c1ccccc1] | 4-({4-[(2-amino-1-phenylethyl)amino]butyl}amino)-5-chloro-2-fluoro-N-1,3-thiazol-2-ylbenzenesulfonamide | Calc'd 498.1, found 498.3 |
| 1-34 | 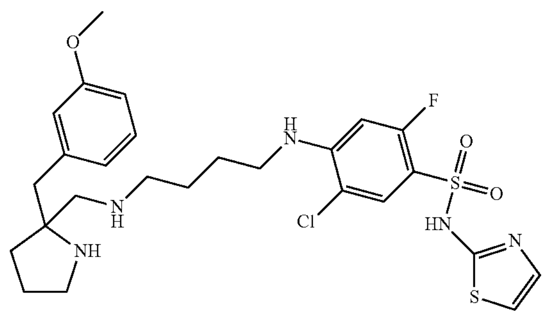 [SMILES: COc1cccc(CC2(CNCCCCNc3cc(F)c(S(=O)(=O)Nc4nccs4)cc3Cl)CCCN2)c1] | 5-chloro-2-fluoro-4-{[4-({[2-(3-methoxy-benzyl)-pyrrolidin-2-yl]methyl}-amino)-butyl]amino}-N-1,3-thiazol-2-yl-benzenesulfonamide | Calc'd 582.2, found 582.2 |
| 1-35 | 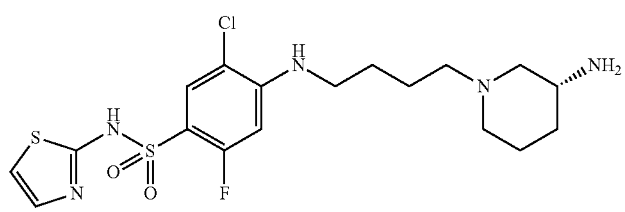 [SMILES: N[C@@H]1CCCN(CCCCNc2cc(F)c(S(=O)(=O)Nc3nccs3)cc2Cl)C1] | 4-({4-[(3R)-3-aminopiperidin-1-yl]butyl}amino)-5-chloro-2-fluoro-N-1,3-thiazol-2-ylbenzenesulfonamide | Calc'd 462.1, found 462.3 |
| 1-36 | 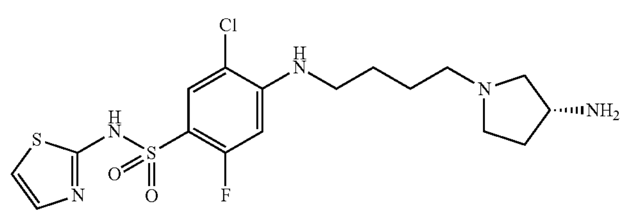 [SMILES: N[C@@H]1CCN(CCCCNc2cc(F)c(S(=O)(=O)Nc3nccs3)cc2Cl)C1] | 4-({4-[(3R)-3-aminopyrrolidin-1-yl]butyl}amino)-5-chloro-2-fluoro-N-1,3-thiazol-2-ylbenzenesulfonamide | Calc'd 448.1, found 448.3 |
| 1-37 | 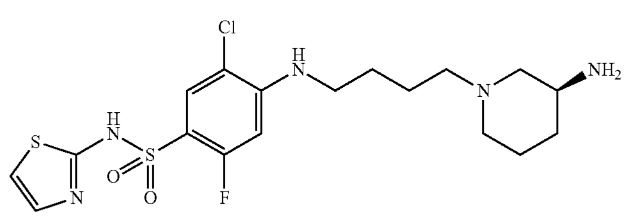 [SMILES: N[C@H]1CCCN(CCCCNc2cc(F)c(S(=O)(=O)Nc3nccs3)cc2Cl)C1] | 4-({4-[(3S)-3-aminopiperidin-1-yl]butyl}amino)-5-chloro-2-fluoro-N-1,3-thiazol-2-ylbenzenesulfonamide | Calc'd 462.1, found 462.3 |

TABLE I-continued

| Example | Structure | IUPAC Name | LC/MS [M + H]+ |
|---|---|---|---|
| 1-38 | 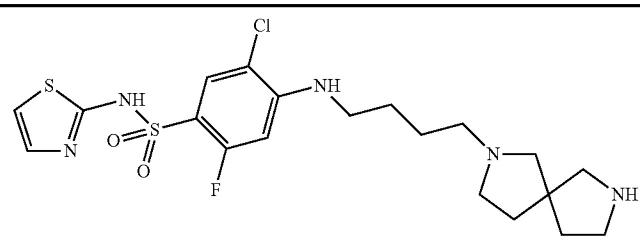 | 5-chloro-4-{[4-(2,7-diazaspiro[4.4]non-2-yl)butyl]amino}-2-fluoro-N-1,3-thiazol-2-ylbenzenesulfonamide | Calc'd 488.1, found 488.3 |
| 1-39 | 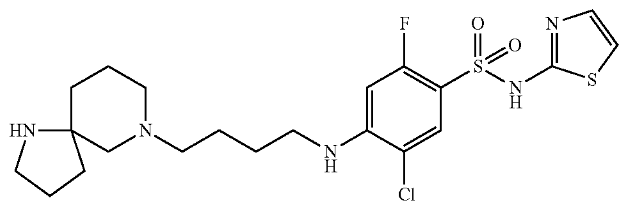 [SMILES: O=S(=O)(Nc1nccs1)c1cc(Cl)c(NCCCCN2CCCC3(CCCN3)C2)cc1F] | 5-chloro-4-{[4-(1,7-diazaspiro[4.5]dec-7-yl)butyl]amino}-2-fluoro-N-1,3-thiazol-2-ylbenzenesulfonamide | Calc'd 502.2, found 502.3 |
| 1-40 | 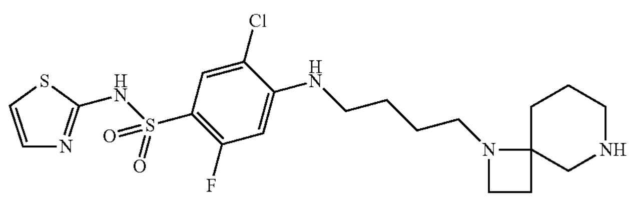 [SMILES: O=S(=O)(Nc1nccs1)c1cc(Cl)c(NCCCCN2CCC23CCCNC3)cc1F] | 5-chloro-4-{[4-(1,6-diazaspiro[3.5]non-1-yl)-butyl]amino}-2-fluoro-N-1,3-thiazol-2-yl-benzenesulfonamide | Calc'd 488.1, found 488.3 |
| 1-41 | 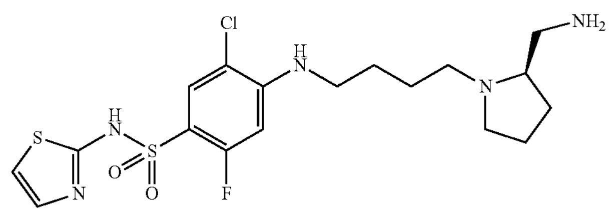 [SMILES: NC[C@H]1CCCN1CCCCNc1cc(F)c(S(=O)(=O)Nc2nccs2)cc1Cl] | 4-({4-[(2R)-2-(aminomethyl)pyrrolidin-1-yl]butyl}amino)-5-chloro-2-fluoro-N-1,3-thiazol-2-ylbenzenesulfonamide | Calc'd 462.1, found 462.3 |
| 1-42 | 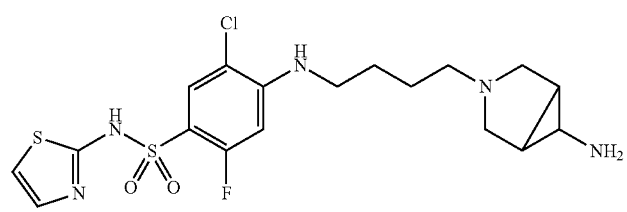 [SMILES: NC1C2CN(CCCCNc3cc(F)c(S(=O)(=O)Nc4nccs4)cc3Cl)CC12] | 4-{[4-(6-amino-3-azabicyclo[3.1.0]hex-3-yl)butyl]amino}-5-chloro-2-fluoro-N-1,3-thiazol-2-ylbenzenesulfonamide | Calc'd 460.1, found 460.3 |
| 1-43 | 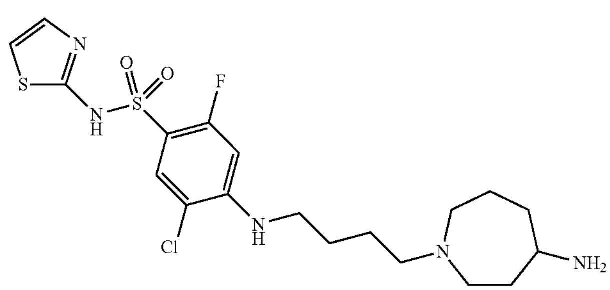 [SMILES: NC1CCCN(CCCCNc2cc(F)c(S(=O)(=O)Nc3nccs3)cc2Cl)CC1] | 4-{[4-(4-aminoazepan-1-yl)butyl]amino}-5-chloro-2-fluoro-N-1,3-thiazol-2-ylbenzenesulfonamide | Calc'd 476.1, found 476.3 |
| 1-44 | 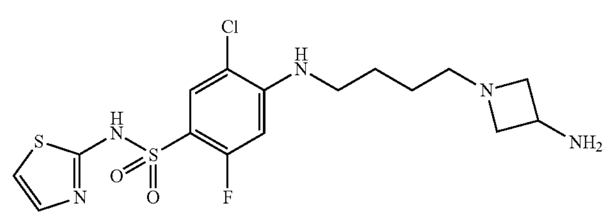 [SMILES: NC1CN(CCCCNc2cc(F)c(S(=O)(=O)Nc3nccs3)cc2Cl)C1] | 4-{[4-(3-aminoazetidin-1-yl)butyl]amino}-5-chloro-2-fluoro-N-1,3-thiazol-2-ylbenzenesulfonamide | Calc'd 434.1, found 434.3 |

TABLE I-continued

| Example | Structure | IUPAC Name | LC/MS [M + H]+ |
|---|---|---|---|
| 1-45 | 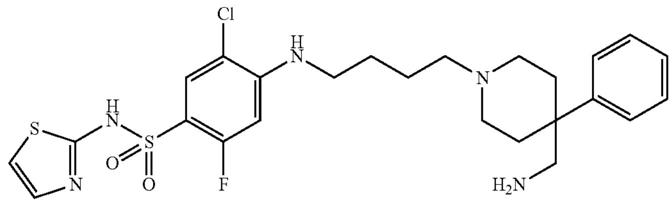 [SMILES: NCC1(c2ccccc2)CCN(CCCCNc2cc(F)c(S(=O)(=O)Nc3nccs3)cc2Cl)CC1] | 4-({4-[4-(aminomethyl)-4-phenylpiperidin-1-yl]butyl}amino)-5-chloro-2-fluoro-N-1,3-thiazol-2-ylbenzenesulfonamide | Calc'd 552.2, found 552.3 |
| 1-46 | 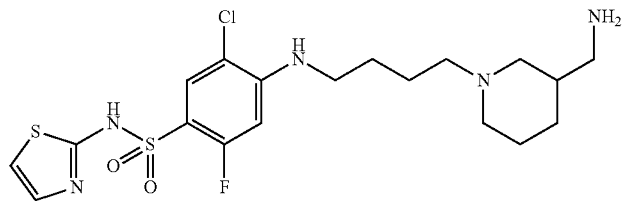 [SMILES: NCC1CCCN(CCCCNc2cc(F)c(S(=O)(=O)Nc3nccs3)cc2Cl)C1] | 4-({4-[3-(aminomethyl)piperidin-1-yl]butyl}amino)-5-chloro-2-fluoro-N-1,3-thiazol-2-ylbenzenesulfonamide | Calc'd 476.1, found 476.3 |
| 1-47 | 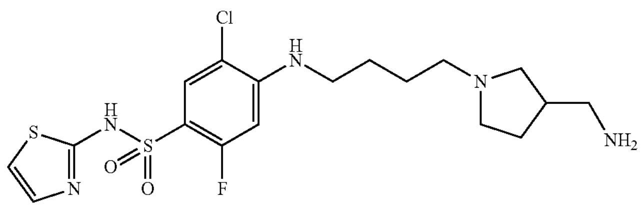 [SMILES: NCC1CCN(CCCCNc2cc(F)c(S(=O)(=O)Nc3nccs3)cc2Cl)C1] | 4-({4-[3-(aminomethyl)pyrrolidin-1-yl]butyl}amino)-5-chloro-2-fluoro-N-1,3-thiazol-2-ylbenzenesulfonamide | Calc'd 462.1, found 462.3 |
| 1-48 | 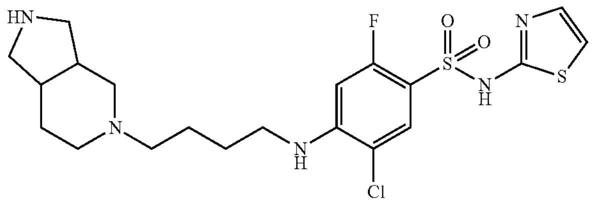 [SMILES: O=S(=O)(Nc1nccs1)c1cc(Cl)c(NCCCCN2CCC3CNCC3C2)cc1F] | 5-chloro-2-fluoro-4-{[4-(octahydro-5H-pyrrolo[3,4-c]pyridin-5-yl)butyl]amino}-N-1,3-thiazol-2-ylbenzenesulfonamide | Calc'd 488.1, found 488.3 |
| 1-49 | 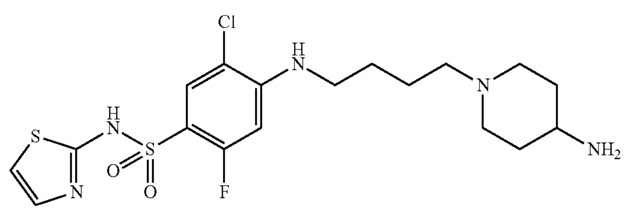 [SMILES: NC1CCN(CCCCNc2cc(F)c(S(=O)(=O)Nc3nccs3)cc2Cl)CC1] | 4-{[4-(4-aminopiperidin-1-yl)butyl]amino}-5-chloro-2-fluoro-N-1,3-thiazol-2-ylbenzenesulfonamide | Calc'd 462.1, found 462.3 |
| 1-50 | 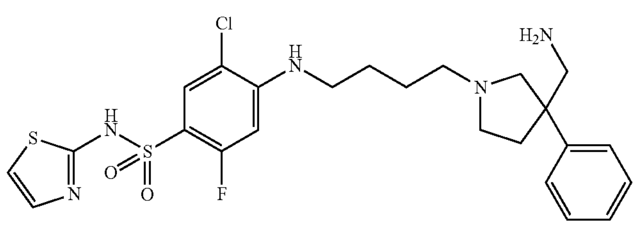 [SMILES: NCC1(c2ccccc2)CCN(CCCCNc2cc(F)c(S(=O)(=O)Nc3nccs3)cc2Cl)C1] | 4-({4-[3-(aminomethyl)-3-phenylpyrrolidin-1-yl]butyl}amino)-5-chloro-2-fluoro-N-1,3-thiazol-2-ylbenzenesulfonamide | Calc'd 538.2, found 538.3 |
| 1-51 | 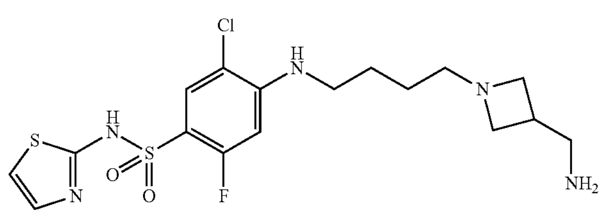 [SMILES: NCC1CN(CCCCNc2cc(F)c(S(=O)(=O)Nc3nccs3)cc2Cl)C1] | 4-({4-[3-(aminomethyl)azetidin-1-yl]butyl}amino)-5-chloro-2-fluoro-N-1,3-thiazol-2-ylbenzenesulfonamide | Calc'd 448.1, found 448.3 |

TABLE I-continued

| Example | Structure | IUPAC Name | LC/MS [M + H]+ |
|---|---|---|---|
| 1-52 | 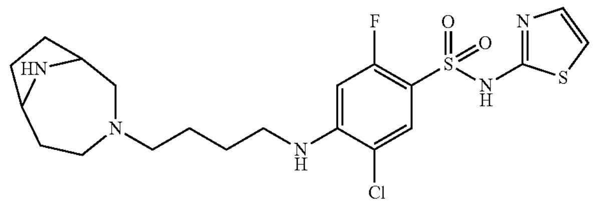 [SMILES: O=S(=O)(Nc1nccs1)c1cc(Cl)c(NCCCCN2CCC3CCC(C2)N3)cc1F] | 5-chloro-4-{[4-(3,9-diazabicyclo[4.2.1]non-3-yl)butyl]amino}-2-fluoro-N-1,3-thiazol-2-ylbenzenesulfonamide | Calc'd 488.1, found 488.3 |
| 1-53 | 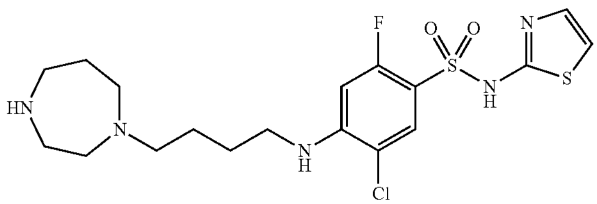 [SMILES: O=S(=O)(Nc1nccs1)c1cc(Cl)c(NCCCCN2CCCNCC2)cc1F] | 5-chloro-4-{[4-(1,4-diazepan-1-yl)butyl]-amino}-2-fluoro-N-1,3-thiazol-2-yl-benzenesulfonamide | Calc'd 462.1, found 462.3 |

Example 2: Preparation of (R or S)-5-chloro-2-fluoro-4-((4-((isoindolin-1-ylmethyl)amino)butyl)amino)-N-(thiazol-2-yl)benzenesulfonamide (2-4 Enantiomer A) and (S or R)-5-chloro-2-fluoro-4-((4-((isoindolin-1-ylmethyl)amino)butyl)amino)-N-(thiazol-2-yl)benzenesulfonamide (2-4 Enantiomer B)

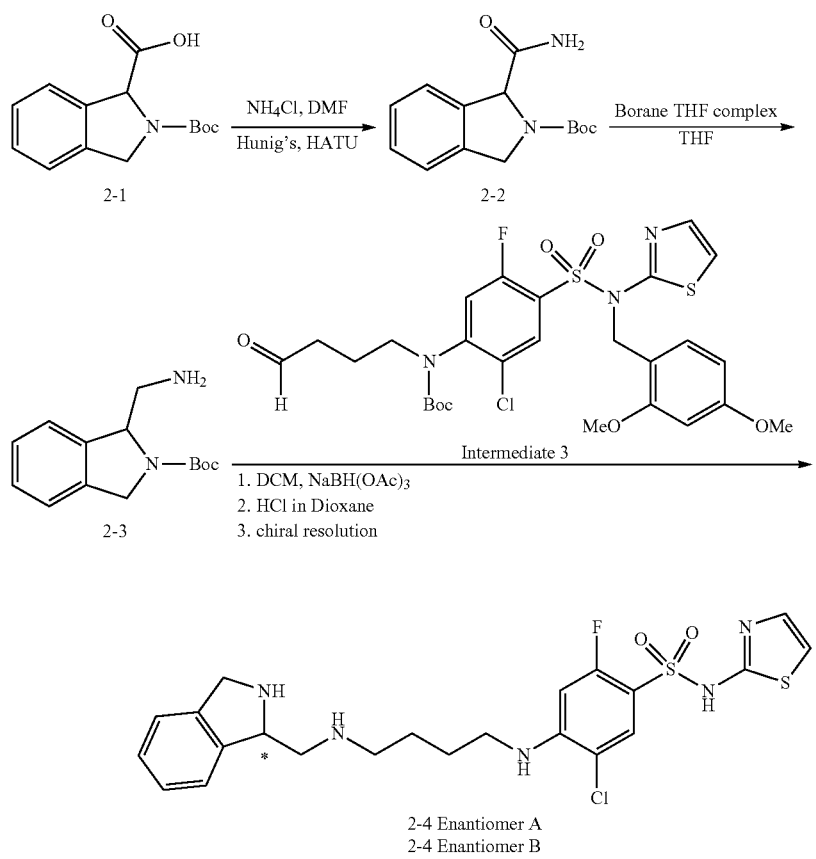

Preparation of tert-butyl 1-carbamoylisoindoline-2-carboxylate (racemic, 2-2)

To a solution of HATU (1.83 g, 4.82 mmol) in DMF (15 mL) was added Hunig's base (2.34 mL, 13.1 mmol). After stirring for 5 min, racemic 2-(tert-butoxycarbonyl)isoindoline-1-carboxylic acid 2-1 (1.15 g, 4.38 mmol) and ammonium chloride (1.41 g, 26.3 mmol) were added to the mixture. The reaction was stirred at room temperature for 18 h. The reaction was partitioned between EtOAc (20 mL) and water (20 mL). The layers were separated and the aqueous layer was extracted with EtOAc (2×20 mL). The combined organic layer was washed with brine, dried over $MgSO_4$, filtered and concentrated. The residue was purified by silica gel chromatography (ISCO 120 g column) eluting with a hexanes/EtOAc gradient (0 to 100% EtOAc) to afford the title compound. LRMS m/z (M+H) 263.2 found, 263.1 required.

Preparation of tert-butyl 1-(aminomethyl)isoindoline-2-carboxylate (racemic, 2-3)

To a solution of racemic 2-2 (0.52 g, 2.0 mmol) in THF (5 mL) at 0° C. was added borane (1.0 M in THF, 9.9 mL, 9.9 mmol). The reaction solution was stirred at room temperature overnight. An additional 5 eq of borane (9.9 mL, 9.9 mmol) was added and the reaction was heated to 50° C. for 4 h. The reaction was then cooled in an ice bath and quenched with MeOH. The reaction mixture was concentrated and to the residue was added in 2 M HCl (5 mL). The solution was stirred for 1 h and then neutralized with 5 N NaOH to pH=10. The solution was then extracted with EtOAc (3×20 mL). The combined EtOAc was dried over $MgSO_4$, filtered and concentrated. The residue was purified by prep-HPLC to give the title compound. LRMS m/z (M+H) 249.0 found, 249.1 required.

Preparation of (2-4 Enantiomer A) and (2-4 Enantiomer B)

To a solution of tert-butyl (2-chloro-4-(N-(2,4-dimethoxybenzyl)-N-(thiazol-2-yl)sulfamoyl)-5-fluorophenyl)(4-oxobutyl)carbamate Intermediate 3 (152 mg, 0.242 mmol) in DCM (ca. 5 mL) was added 2-3 (60 mg, 0.242 mmol). The mixture was stirred for at room temperature for 20 min, then sodium triacetoxyhydroborate (154 mg, 0.725 mmol) was added to the mixture. The reaction was stirred at room temperature for 2 h. The reaction was then partitioned between DCM (15 mL) and saturated aqueous $NaHCO_3$ (15 mL). The aqueous was extracted with DCM (2×15 mL). The organic phases were combined, dried over $Na_2SO_4$ and concentrated in vacuo. The isolated solid was then treated with 4 M HCl in dioxane (3 mL) for 1 h at room temperature. The solution was then concentrated in vacuo and the residue purified by prep-HPLC to give the desired product (racemic). The material was subsequently resolved to single enantiomers using chiral SFC chromatography (AS column, eluting with 50% MeOH with 0.2% $NH_4OH/CO_2$) to give a faster eluting peak (2-Enantiomer A) and a slower eluting peak (2-4 Enantiomer B). $^1$H NMR (500 MHz, $CD_3OD$): δ 7.69 (dd, J=5.0 Hz, 4.5 Hz, 1H); 7.47 (m, 4H); 7.10 (t, 1H); 6.72 (t, 1H); 6.54 (dd, J=5.0 Hz, 4.0 Hz, 1H); 5.28 (m, 1H); 4.65 (m, 2H); 3.71 (m, 1H); 3.57 (m, 1H); 3.17 (m, 2H); 1.84 (m, 2H); 1.73 (m, 2H). LRMS m/z (M+H) 510.0 found, 510.1 required.

Example 3: 4-((4-((2-(aminomethyl)benzyl)amino)butyl)amino)-5-chloro-2-fluoro-N-(thiazol-2-yl)benzenesulfonamide (3-4)

Scheme 3

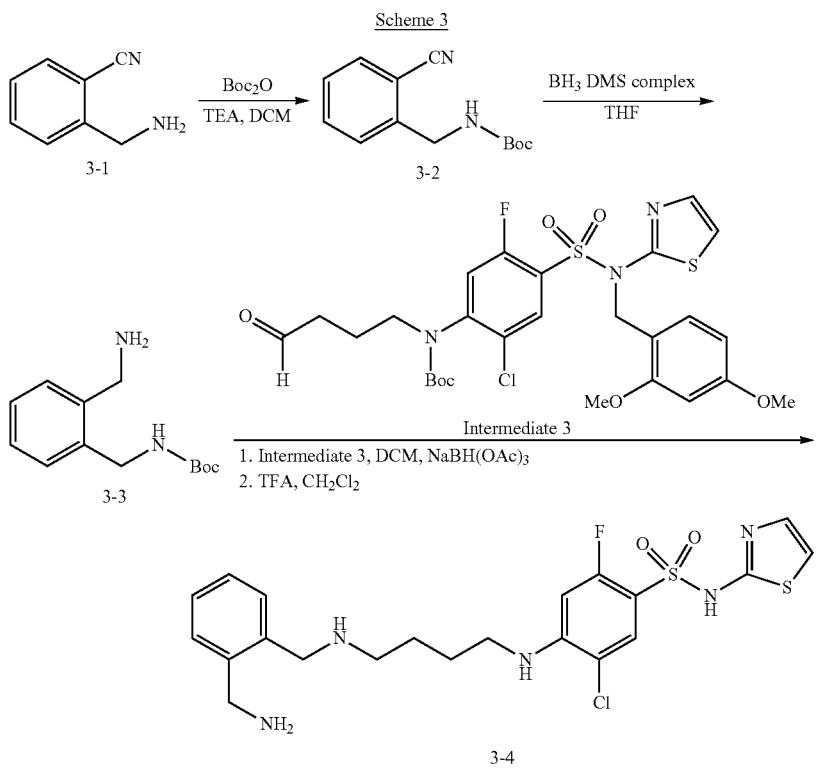

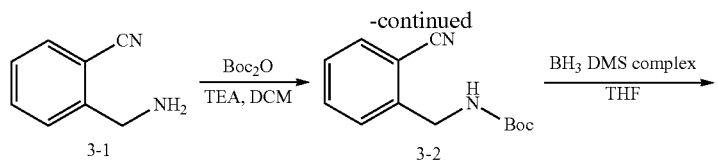

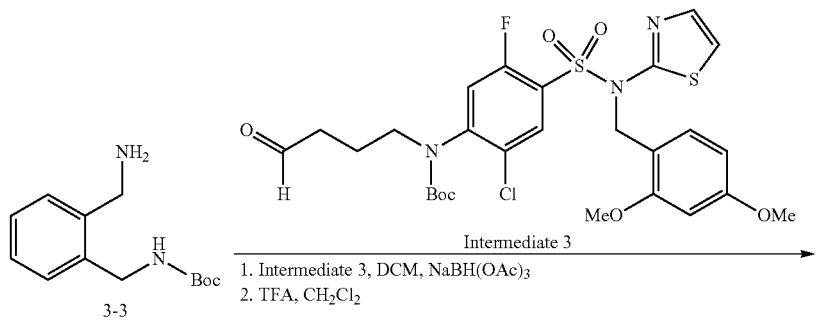

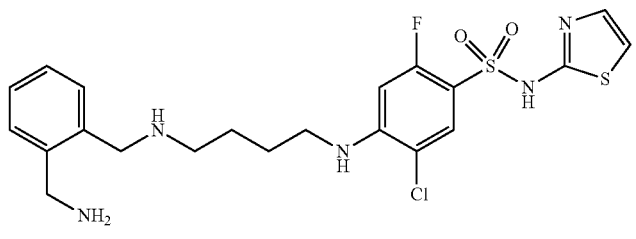

Preparation of tert-butyl 2-cyanobenzylcarbamate (3-2)

To a suspension of 2-(aminomethyl)benzonitrile 3-1 (520 mg, 3.93 mmol) in DCM (10 mL) was added di-tert-butyl dicarbonate (945 mg, 4.33 mmol), and triethylamine (1.21 mL, 8.66 mmol). The reaction mixture was stirred at room temperature for 18 hours. The mixture was then partitioned between DCM (15 mL) and saturated aqueous NaHCO$_3$ (15 mL). The aqueous was extracted with DCM (2×15 mL). The organic phases were combined, dried over Na$_2$SO$_4$ and concentrated in vacuo to give the title compound, which is used in the next step without purification. LRMS m/z (M+H) 233.2 found, 233.1 required.

Preparation of tert-butyl 2-(aminomethyl)benzylcarbamate (3-3)

To a solution of 3-2 (820 mg, 3.53 mmol) in THF (9 mL) at 0° C. was added borane dimethyl sulfide complex (3.35 mL, 35.3 mmol). The reaction mixture was warmed to room temperature and stirred for 2 days. The reaction was cooled in an ice bath and slowly quenched with aqueous 2 N HCl. The reaction mixture was then neutralized with aqueous 1 N NaOH to pH ~10 and extracted with EtOAc (3×30 mL). The combined organics were washed with brine, dried over MgSO$_4$, filtered and concentrated to give the title compound. LRMS m/z (M+H) 237.0 found, 237.1 required.

Preparation of 4-((4-((2-(aminomethyl)benzyl)amino)butyl)amino)-5-chloro-2-fluoro-N-(thiazol-2-yl)benzenesulfonamide (3-4)

To a solution of tert-butyl (2-chloro-4-(N-(2,4-dimethoxybenzyl)-N-(thiazol-2-yl)sulfamoyl)-5-fluorophenyl)(4-oxobutyl)carbamate Intermediate 3 (70 mg, 0.11 mmol) in DCM (2 mL) was added 3-3 (42 mg, 0.18 mmol). The mixture was stirred at room temperature for 10 min. before sodium triacetoxyborohydride (71 mg, 0.33 mmol) was added. The reaction was stirred at room temperature for 18 h. The mixture was then partitioned between DCM (15 mL) and saturated aqueous NaHCO$_3$ (15 mL). The aqueous was extracted with DCM (2×15 mL). The organic phases were combined, dried over Na$_2$SO$_4$ and concentrated in vacuo. The solid was subsequently dissolved in DCM (2 mL) and TFA (0.43 mL, 5.59 mmol). The reaction mixture was stirred at room temperature for 2 h. The solution was concentrated in vacuo and the residue was purified by prep-HPLC to give the title compound as a solid. $^1$H NMR (500 MHz, CD$_3$OD): δ 7.69 (t, 1H); 7.55 (m, 4H); 7.10 (t, 1H); 6.73 (t, 1H); 6.53 (dd, J=6.0 Hz, 5.0 Hz, 1H); 4.34 (d, J=5.5 Hz, 2H); 4.30 (d, J=5.5 Hz, 2H); 3.18 (m, 2H); 1.82 (m, 2H); 1.72 (m, 2H). LRMS m/z (M+H) 498.1 found, 498.1 required.

US 10,968,210 B2
63
Example 6: 5-chloro-2-fluoro-4-((((1R,3S or 1S,3R)-3-(((S)-pyrrolidin-2-ylmethyl)amino)cyclohexyl)methyl)amino)-N-(thiazol-2-yl)benzenesulfonamide (6-7 Enantiomer A) and 5-chloro-2-fluoro-4-((((1S,3R or 1R,3S)-3-(((S)-pyrrolidin-2-ylmethyl)amino)cyclohexyl)methyl)amino)-N-(thiazol-2-yl)benzenesulfonamide (6-7 Enantiomer B)
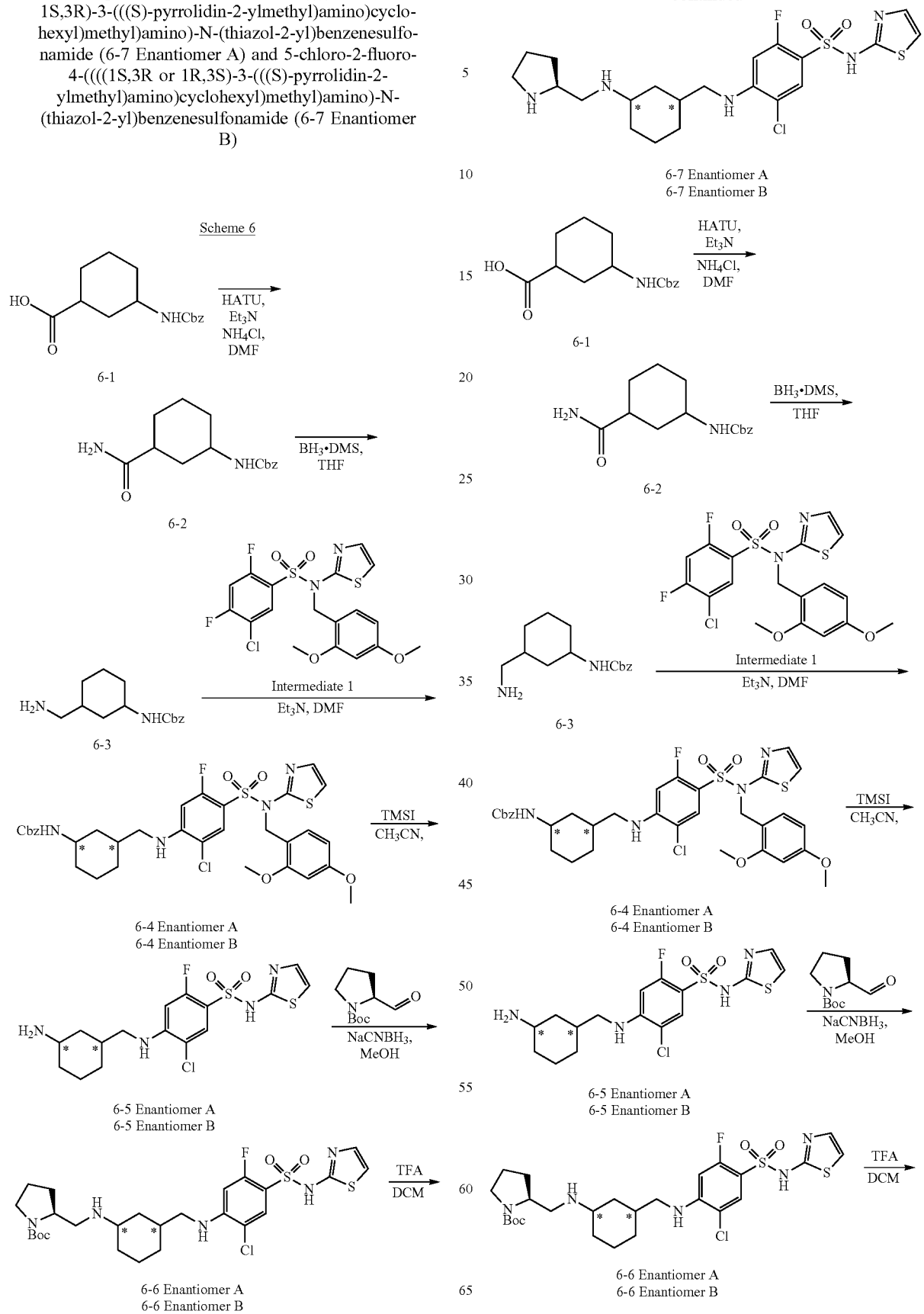

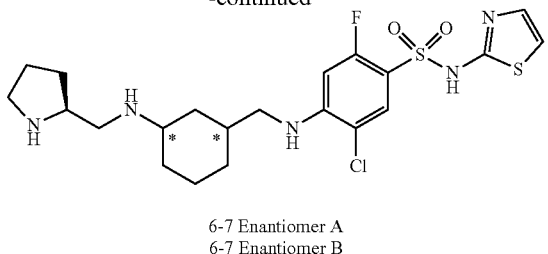

6-7 Enantiomer A
6-7 Enantiomer B

Preparation of benzyl ((1S,3R and 1R,3S)-3-carbamoylcyclohexyl)carbamate (racemic, 6-2)

A racemic mixture of (1S,3R and 1R,3S)-3-(((benzyloxy)carbonyl)amino)cyclohexane-carboxylic acid 6-1 (2.80 g, 10.10 mmol), NH$_4$Cl (1.62 g, 30.3 mmol), Et$_3$N (5.63 ml, 40.4 mmol) and HATU (7.68 g, 20.2 mmol) in DMF (50 mL) was stirred at 15° C. for 16 h. The reaction was detected by TLC. After the reaction completed, the solid was filtered and the mixture was concentrated in vacuo to give the crude product which was purified by column chromatography (PE:EA=1:1) to give the title compound. $^1$H NMR (CD$_3$OD, 400 MHz) δ 7.35 (d, J 3.6 Hz, 5H), 5.07 (s, 2H), 3.45 (dd, J=3.6, 11.6 Hz, 1H), 2.39-2.28 (m, 1H), 2.07-1.99 (m, 2H), 1.94-1.77 (m, 3H), 1.45-1.37 (m, 2H), 1.23-1.15 (m, 1H). LRMS m/z (M+H) 277.2 found, 277.3 calc'd.

Benzyl ((1S,3R and 1R,3S)-3-(aminomethyl)cyclohexyl)carbamate (racemic, 6-3)

To a solution of racemic benzyl ((1S,3R and 1R,3S)-3-carbamoylcyclohexyl)carbamate 6-2 (1.0 g, 3.6 mmol) in THF (20 mL) was added BH$_3$.DMS (2.0 ml, 21 mmol) at 0° C. under N$_2$. Then the mixture was stirred at 40° C. for 16 h. After the reaction completed, MeOH (10 mL) was added to the mixture which was stirred for 10 min. The mixture was concentrated in vacuum to give a residue. The residue was dissolved in MeOH, stirred at 15° C. for 2 h and concentrated in vacuo to give the crude product 6-3 which was used in the next step directly. $^1$H NMR (CD$_3$OD, 400 MHz) δ 7.35-7.23 (m, 5H), 5.04 (br. s., 2H), 3.62-3.51 (m, 1H), 2.81-2.68 (m, 2H), 1.98 (d, J=10.4 Hz, 1H), 1.89-1.68 (m, 5H), 1.42-1.31 (m, 2H), 1.16-1.07 (m, 1H). LRMS m/z (M+H) 263.2 found, 263.3 calc'd.

Step 3: Benzyl ((1S,3R or 1R,3S)-3-(((2-chloro-4-(N-(2,4-dimethoxybenzyl)-N-(thiazol-2-yl)sulfamoyl)-5-fluorophenyl)amino)methyl)cyclohexyl)carbamate (6-4 Enantiomer A) and benzyl ((1R,3S or 1S,3R)-3-(((2-chloro-4-(N-(2,4-dimethoxybenzyl)-N-(thiazol-2-yl)sulfamoyl)-5-fluorophenyl)amino)methyl)cyclohexyl)carbamate (6-4 Enantiomer B)

A mixture of racemic 6-3 (900 mg, 3.43 mmol), Intermediate 1 (1.74 g, 3.77 mmol) and Et$_3$N (1.74 mg, 17.2 mmol) in DMF (25 mL) was stirred for 15 h at 50° C. under N$_2$. After completion of the reaction, the mixture was concentrated by vacuum to give a residue, which was purified by column chromatography (PE:EA=1:1) to give racemic 6-4. The product was resolved by SFC (Column: Chiralpak AD-3 150×4.6 mm I.D., 3 um Mobile phase: 40% of methanol (0.05% DEA) in CO$_2$, Flow rate: 2.5 mL/min, Wavelength: 220 nm, t1=8.47, t2=1 1.89) to give a faster eluting peak 1 (6-4 Enantiomer A) and a slower eluting peak (6-4 Enantiomer B). $^1$H NMR (CD$_3$OD, 400 MHz) δ 7.49 (d, J=7.2 Hz, 1H), 7.37 (d, J=3.6 Hz, 1H), 7.32-7.27 (m, 5H), 7.18 (d, J=3.6 Hz, 1H), 7.07-7.05 (m, 1H), 6.48 (d, J=12.8 Hz, 1H), 6.37-6.32 (m, 2H), 5.47 (s, 2H), 5.07 (s, 2H), 3.70 (d, J=3.6 Hz, 6H), 3.38 (br. s., 1H), 3.10 (d, J=6.0 Hz, 2H), 1.99 (br. s., 1H), 1.89 (d, J=11.2 Hz, 1H), 1.77 (br. s., 2H), 1.40-1.30 (m, 2H), 1.14 (d, J=12.4 Hz, 1H), 0.88 (d, J 11.6 Hz, 2H). LRMS m/z (M+H) 703.1 found, 703.2 calc'd.

Step 4: 4-((((1S,3R or 1R,3S)-3-aminocyclohexyl)methyl)amino)-5-chloro-2-fluoro-N-(thiazol-2-yl)benzenesulfonamide (6-5 Enantiomer A) and 4-((((1R,3S or 1S,3R)-3-aminocyclohexyl)methylamino)-5-chloro-2-fluoro-N-(thiazol-2-yl)benzenesulfonamide (6-5 Enantiomer B)

To the solution of 6-4 Enantiomer A (320 mg, 0.498 mmol) in CH$_3$CN (8 mL) was added TMSI (1.00 ml, 0.498 mmol) at 0° C. dropwise. The mixture was stirred at 0° C. for 1 h. Reaction progress was monitored by LCMS and TLC. After completion of the reaction, the mixture was quenched by MeOH, and concentrated by vacuum to give a residue, which was purified by prep-TLC (DCM:MeOH=10:1). The solid was purified by prep-HPLC to give 6-5 (Enantiomer A). $^1$H NMR (CD$_3$OD, 400 MHz) 7.69 (d, J 7.2 Hz, 1H), 7.11 (d, J 4.4 Hz, 1H), 6.73 (d, J 4.4 Hz, 1H), 6.54 (d, J 12.4 Hz, 1H), 3.26-3.21 (m, 1H), 3.16-3.06 (m, 2H), 2.10 (d, J 11.2 Hz, 1H), 2.01 (d, J 11.6 Hz, 1H), 1.91 (d, J 13.2 Hz, 1H), 1.82 (d, J 10.4 Hz, 2H), 1.41-1.26 (m, 2H), 1.07-0.92 (m, 2H). LRMS m/z (M+H) 419.1 found, 419.0 calc'd.

6-5 (Enantiomer B) was prepared from 6-4 Enantiomer B using a similar procedure to that of 6-5 (enantiomer A) reported above. $^1$H NMR (CD$_3$OD, 400 MHz) 7.67 (d, J 7.2 Hz, 1H), 7.09 (d, J 4.8 Hz, 1H), 6.71 (d, J 4.8 Hz, 1H), 6.53 (d, J 12.8 Hz, 1H), 3.24-3.17 (m, 1H), 3.15-3.00 (m, 2H), 2.08 (d, J 11.6 Hz, 1H), 1.99 (d, J 11.2 Hz, 1H), 1.89 (d, J 13.2 Hz, 1H), 1.80 (d, J 11.2 Hz, 2H), 1.39 (d, J 13.2 Hz, 1H), 1.32-1.27 (m, 1H), 1.09-0.92 (m, 2H). LRMS m/z (M+H) 419.1 found, 419.0 calc'd.

(S)-tert-butyl 2-(((((1S,3R or 1R,3S)-3-(((2-chloro-5-fluoro-4-(N-(thiazol-2-yl)sulfamoyl)phenyl)amino)methyl)cyclohexyl)amino)methyl)pyrrolidine-1-carboxylate (6-6 Enantiomer A) and (S)-tert-butyl 2-(((((1R,3S or 1S,3R)-3-(((2-chloro-5-fluoro-4-(N-(thiazol-2-yl)sulfamoyl)phenyl)amino)methyl)cyclohexyl)amino)methyl)pyrrolidine-1-carboxylate (6-6 Enantiomer B)

A mixture of 6-5 Enantiomer A (120 mg, 0.310 mmol) and (S)-tert-butyl 2-formylpyrrolidine-1-carboxylate (61.8 mg, 0.310 mmol) in MeOH (8 mL) was stirred at 40° C. for 12 h. NaCNBH$_3$ (39 mg, 0.62 mmol) was added in several portions to the stirred mixture. The reaction was stirred at 40° C. for 1 h. The reaction was concentrated by vacuum to give a residue, which was purified by prep-TLC (DCM:MeOH=10:1) to give 6-6 Enantiomer A. $^1$H NMR (CD$_3$OD, 400 MHz) δ 7.67 (d, J 7.2 Hz, 1H), 7.12 (d, J 4.8 Hz, 1H), 6.73 (d, J 4.4 Hz, 1H), 6.55 (d, J 12.8 Hz, 1H), 4.04 (br. s., 1H), 3.44-3.39 (m, 1H), 3.24-3.09 (m, 6H), 2.21-2.09 (m, 3H), 1.91-1.78 (m, 6H), 1.44 (s, 9H), 1.37-1.26 (m, 2H), 1.15-1.07 (m, 1H), 1.03-0.92 (m, 1H). LRMS m/z (M+H) 602.3 found, 602.1 calc'd.

6-6 (Enantiomer B) was prepared from 6-5 Enantiomer B using a similar procedure to that of 6-6 Enantiomer A reported above. $^1$H NMR (CD$_3$OD, 400 MHz) δ 7.67 (d, J 7.2 Hz, 1H), 7.02 (d, J 11.2 Hz, 1H), 6.64 (br. s., 1H), 6.49 (d, J 11.2 Hz, 1H), 4.03 (br. s., 1H), 3.42 (d, J=6.8 Hz, 1H), 3.34 (br. s., 1H), 3.25-3.06 (m, 5H), 2.23 (d, J=10.0 Hz, 1H), 2.11 (d, J=4.8 Hz, 2H), 1.95-1.72 (m, 6H), 1.46 (s, 9H), 1.39-1.26 (m, 2H), 1.19-1.09 (m, 1H), 0.98 (d, J=10.6 Hz, 1H). LRMS m/z (M+H) 602.3 found, 602.1 calc'd.

5-chloro-2-fluoro-4-((((1R,3S or 1S,3R)-3-(((S)-pyrrolidin-2-ylmethyl)amino)cyclohexyl)methyl)amino)-N-(thiazol-2-yl)benzenesulfonamide (6-7 Enantiomer A) and 5-chloro-2-fluoro-4-((((1S,3R or 1R,3S)-3-(((S)-pyrrolidin-2-ylmethyl)amino)cyclohexyl)methyl)amino)-N-(thiazol-2-yl)benzenesulfonamide (6-7 Enantiomer B)

A mixture of 6-6 Enantiomer A (80 mg, 0.13 mmol) and TFA (2.0 ml, 26 mmol) in CH$_2$Cl$_2$ (4 mL) was stirred at 15° C. for 1 h. The reaction was detected by LCMS. After the reaction completed, the mixture was concentrated in vacuum to give the crude product which was purified by prep-HPLC to give 6-7 Enantiomer A. $^1$H NMR (CD$_3$OD, 400 MHz) 7.68 (d, J=7.2 Hz, 1H), 7.11 (d, J=4.8 Hz, 1H), 6.73 (d, J=4.8 Hz, 1H), 6.54 (d, J=12.8 Hz, 1H), 3.91-3.81 (m, 1H), 3.45 (d, J=6.4 Hz, 2H), 3.39 (t, J=7.2 Hz, 2H), 3.18 (dd, J=6.8, 12.4 Hz, 3H), 2.33 (dd, J=4.4, 12.4 Hz, 1H), 2.23 (d, J=11.2 Hz, 1H), 2.14 (d, J=6.4 Hz, 2H), 2.08-2.00 (m, 1H), 1.94 (br. s., 1H), 1.86-1.77 (m, 3H), 1.42-1.34 (m, 2H), 1.19-1.10 (m, 1H), 0.99 (d, J=11.7 Hz, 1H). LRMS m/z (M+H) 502.0 found, 502.1 calc'd.

6-7 Enantiomer B was prepared from 6-6 Enantiomer B using a similar procedure to that of 6-7 Enantiomer A reported above. $^1$H NMR (CD$_3$OD, 400 MHz) 7.68 (d, J=7.2 Hz, 1H), 7.11 (d, J=4.8 Hz, 1H), 6.73 (d, J=4.8 Hz, 1H), 6.53 (d, J=12.4 Hz, 1H), 3.95-3.84 (m, 1H), 3.53-3.47 (m, 1H), 3.44 (d, J=5.2 Hz, 1H), 3.39 (t, J=7.2 Hz, 2H), 3.18 (dd, J 6.8, 11.6 Hz, 3H), 2.37-2.28 (m, 1H), 2.23 (d, J=11.2 Hz, 1H), 2.14 (d, J=6.0 Hz, 2H), 2.07-1.99 (m, 1H), 1.93 (br. s., 1H), 1.85-1.74 (m, 3H), 1.41-1.32 (m, 2H), 1.16 (d, J=12.2 Hz, 1H), 1.03-0.93 (m, 1H). LRMS m/z (M+H) 502.0 found, 502.1 calc'd.

The following compounds were prepared using the methodology herein, but substituting the appropriately substituted reagent, as described in the Reaction Schemes, Intermediates and Examples. The requisite starting materials were commercially available, described in the literature or readily synthesized by one skilled in the art of organic synthesis without undue experimentation.

TABLE 4

| Example | Structure | IUPAC Name | LC/MS [M + H]+ |
|---|---|---|---|
| 6-8 | 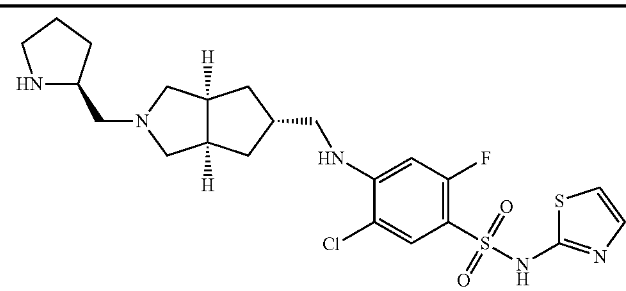 | 5-chloro-2-fluoro-4-[({(3aR,5R,6aS)-2-[(2S)-pyrrolidin-2-ylmethyl]octahydrocyclopenta[c]pyrrol-5-yl}methyl)amino]-N-1,3-thiazol-2-ylbenzenesulfonamide | Calc'd 514.2, found 514.0 |
| 6-9 | 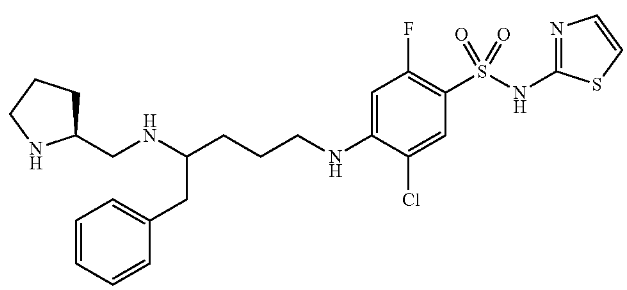 [SMILES: O=S(=O)(Nc1nccs1)c1cc(Cl)c(NCCCC(Cc2ccccc2)NC[C@@H]2CCCN2)cc1F] | 5-chloro-2-fluoro-4-[(5-phenyl-4-{[(2S)-pyrrolidin-2-ylmethyl]amino}pentyl)amino]-N-1,3-thiazol-2-ylbenzenesulfonamide | Calc'd 552.2, found 552.2 |

Example 7: 4-[(4-{[(2S)-pyrrolidin-2-ylmethyl]amino}butyl)amino]-N-1,3-thiazol-2-yl-3-(trifluoromethyl)benzenesulfonamide (Ex 7-14)

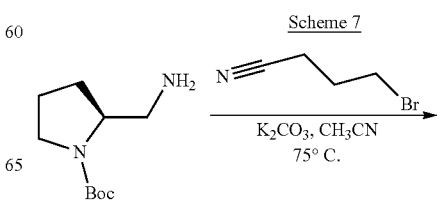

Scheme 7

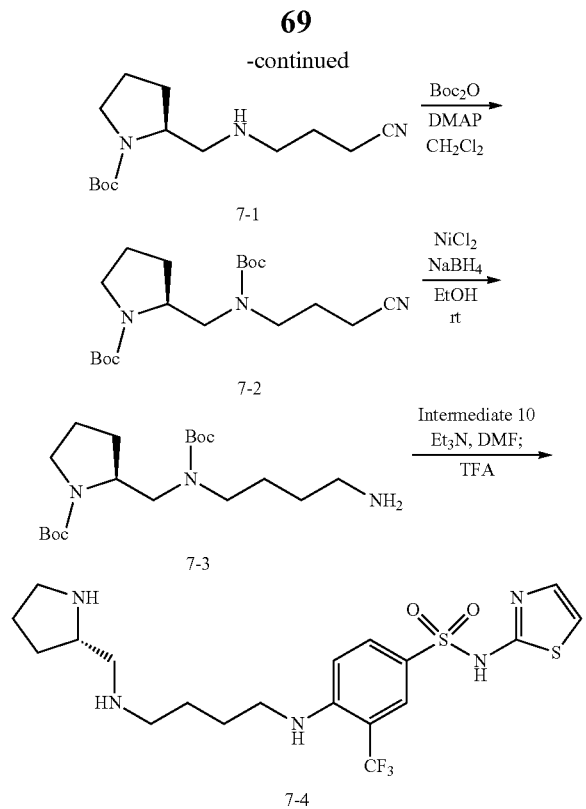

(S)-tert-butyl 2-(((tert-butoxycarbonyl)(3-cyanopropyl)amino)methyl)pyrrolidine-1-carboxylate (7-2)

To a solution of 7-1 (2.67 g, 9.99 mmol) in CH$_2$Cl$_2$ (50 ml) at room temperature was added Boc$_2$O (2.73 g, 12.5 mmol) and DMAP (1.83 g, 15.0 mmol). The mixture was stirred at room temperature for 2 h. The solution was quenched with water and extracted with CH$_2$Cl$_2$. The combined organic extracts were dried (Na$_2$SO$_4$), filtered and concentrated. Purification by isco silica gel chromatography (0-25% ethyl acetate/hexanes) on a 80 g RediSep Rf silica gel column afforded the title compound as a solid. LRMS m/z (M+H) 368.3 found, 368.3 calc'd.

(S)-tert-butyl 2-(((4-aminobutyl)(tert-butoxycarbonyl)amino)methyl)pyrrolidine-1-carboxylate (7-3)

To a solution of 7-2 (1.70 g, 27.2 mmol) in EtOH (23 ml) at room temperature was added NiCl$_2$ (0.60 g, 4.63 mmol) and NaBH$_4$ (0.53 g, 13.9 mmol). The mixture was stirred at room temperature 2 h. The mixture was filtered through celite, washed with ethanol and concentrated. Purification by 25 g SCX column with methanol flush (50 mL), followed by 2 M NH$_3$ in MeOH (100 mL) flush afforded the title compound after concentration as a clear gum. LRMS m/z (M+H) 372.4 found, 372.3 calc'd.

(S)-4-((4-((pyrrolidin-2-ylmethyl)amino)butyl)amino)-N-(thiazol-2-yl)-3-(trifluoromethyl)benzenesulfonamide (7-14)

To a solution of Intermediate 10 (45 mg, 0.094 mmol) and triethylamine (0.053 ml, 0.38 mmol) in NMP (1 ml) at room temperature was added 7-3 (35 mg, 0.094 mmol). The mixture was stirred at 60° C. 16 h. The resulting mixture was concentrated to dryness and then diluted with CH$_2$Cl$_2$ (1 mL) and TFA (0.5 mL). The solution was stirred at room temperature 30 min and then concentrated and purified by prep-HPLC to give the title compound as a clear gum. $^1$H NMR (500 MHz, d$^6$-DMSO) δ 7.76 (d, J=9.1 Hz, 1H); 7.75 (s, 1H); 7.25 (d, J=4.6 Hz, 1H); 6.94 (d, J=9.1 Hz, 1H); 6.82 (d, J=4.6 Hz, 1H); 6.30 (s, 1H); 3.73 (m, 1H); 3.23-3.28 (m, 3H); 2.89-3.05 (m, 3H); 2.12 (m, 1H); 1.94 (m, 1H); 1.88 (m, 1H); 1.50-1.74 (m, 7H); LRMS m/z (M+H) 478.3 found, 478.2 calc'd.

(S)-tert-butyl 2-((3-cyanopropyl)aminomethyl)pyrrolidine-1-carboxylate (7-1)

To a solution of (S)-tert-butyl 2-(aminomethyl)pyrrolidine-1-carboxylate (2.00 g, 9.99 mmol) in acetonitrile (50.0 ml) at room temperature was added 4-bromobutyronitrile (1.49 g, 9.99 mmol) and K$_2$CO$_3$ (2.90 g, 21.0 mmol). The mixture was heated to 75° C. for 24 h. The mixture was then cooled to room temperature and quenched with water and extracted with CH$_2$Cl$_2$. The combined organic extracts were dried (Na$_2$SO$_4$), filtered and concentrated to afford crude 7-1 which was used without further purification. LRMS m/z (M+H) 268.0 found, 268.2 calc'd.

TABLE 5

| Example | Structure | IUPAC Name | LC/MS [M + H]+ |
|---|---|---|---|
| 7-7 | 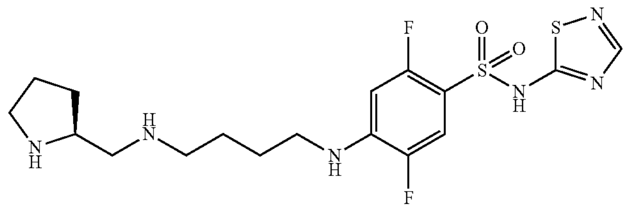 [SMILES: O=S(=O)(Nc1ncns1)c1cc(F)c(NCCCCNC[C@@H]2CCCN2)cc1F] | 2,5-difluoro-4-[(4-{[(2S)-pyrrolidin-2-ylmethyl]amino}butyl)amino]-N-1,2,4-thiadiazol-5-ylbenzenesulfonamide | Calc'd 447.1, found 447.3 |
| 7-12 | 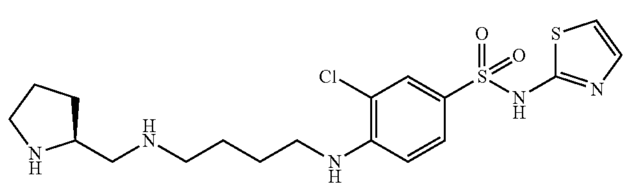 [SMILES: O=S(=O)(Nc1nccs1)c1ccc(NCCCCNC[C@@H]2CCCN2)c(Cl)c1] | 3-chloro-4-[(4-{[(2S)-pyrrolidin-2-ylmethyl]amino}butyl)amino]-N-1,3-thiazol-2-ylbenzenesulfonamide | Calc'd 444.1, found 444.3 |

TABLE 5-continued

| Example | Structure | IUPAC Name | LC/MS [M + H]+ |
|---|---|---|---|
| 7-13 | 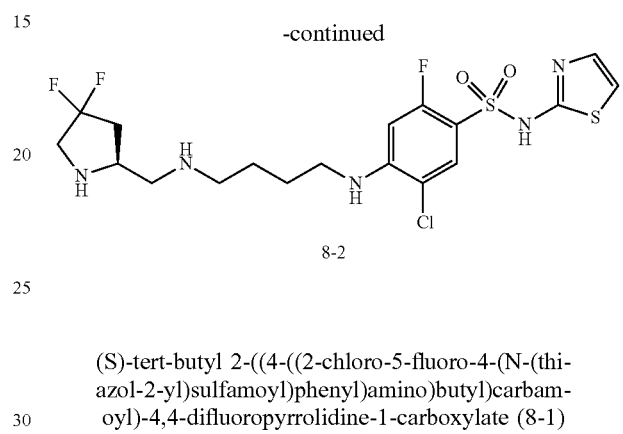 | 3-chloro-N-(5-fluoro-1,3-thiazol-2-yl)-4-[(4-{[(2S)-pyrrolidin-2-ylmethyl]amino}butyl)amino]benzenesulfonamide | Calc'd 462.1, found 462.3 |

Example 8: (S)-5-chloro-4-((4-(((4,4-difluoropyrrolidin-2-yl)methyl)amino)butyl)amino)-2-fluoro-N-(thiazol-2-yl)benzenesulfonamide (8-2)

Scheme 8

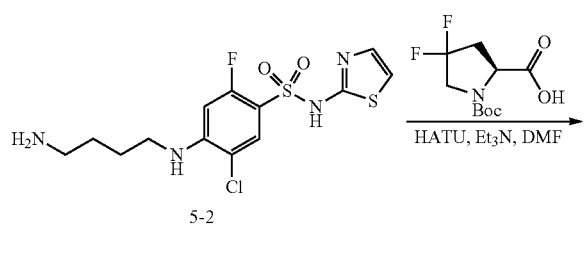

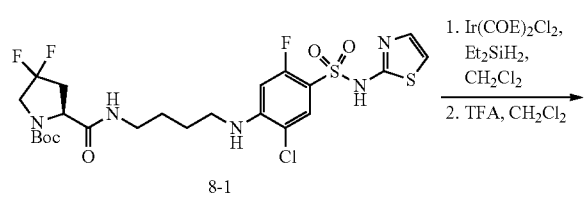

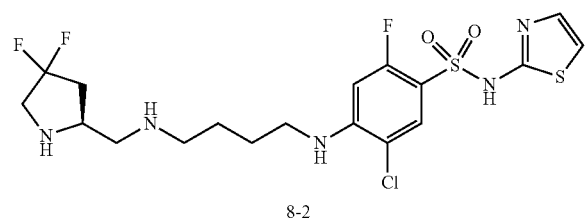

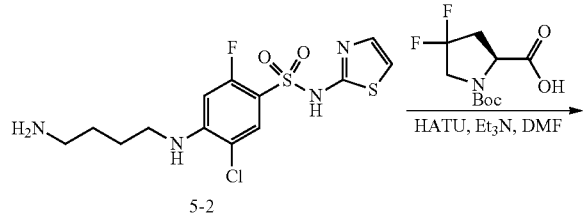

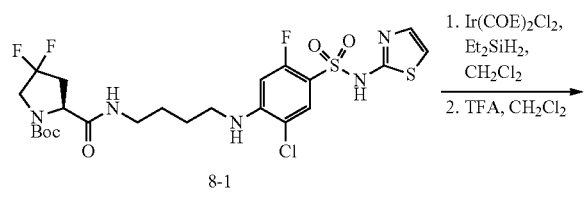

(S)-tert-butyl 2-((4-((2-chloro-5-fluoro-4-(N-(thiazol-2-yl)sulfamoyl)phenyl)amino)butyl)carbamoyl)-4,4-difluoropyrrolidine-1-carboxylate (8-1)

To a solution of 5-2 (300 mg, 0.792 mmol), (S)-1-(tert-butoxycarbonyl)-4,4-difluoropyrrolidine-2-carboxylic acid (199 mg, 0.792 mmol), and Et$_3$N (330 ul, 2.38 mmol) in DMF (3 mL) was added HATU (300 mg, 0.792 mmol). The reaction was stirred at room temperature for 1 h, and purified by prep-HPLC to give the desired product. LRMS m/z (M+H) 612.3 found, 612.1 calc'd.

(S)-5-chloro-4-((4-(((4,4-difluoropyrrolidin-2-yl)methyl)amino)buty)amino)-2-fluoro-N-(thiazol-2-yl)benzenesulfonamide (8-2)

Chlorobis(cyclooctene)iridium(I) dimer (6.73 mg, 7.52 µmol) was added to a microwave vial containing diethylsilane (779 µl, 6.01 mmol) at room temperature. The mixture was stirred for 5 min, upon which time a solution of 8-1 (230 mg, 0.376 mmol) in DCM (375 uL) was added. The vial was sealed and heated to 80° C. for 2 h. The reaction was concentrated and then taken up in a 1:1 DCM:TFA (2 mL) solution and stirred for an additional 30 min at room temperature. The reaction was then concentrated and purified by prep-HPLC to give the desired product. $^1$H NMR (500 MHz, DMSO): δ 7.58 (d, J=7.2 Hz, 1H); 7.27 (d, J=4.6 Hz, 1H); 6.83 (d, J=4.6 Hz, 1H); 6.68 (d, J=7.2 Hz, 1H); 4.15 (s, 1H); 3.24 (s, 2H); 2.99 (s, 2H); 2.54 (s, 1H); 1.60-1.68 (m, 4H). LRMS m/z (M+H) 498.3 found, 498.1 calc'd.

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE 6

| Example | Structure | IUPAC Name | LC/MS [M + H]+ |
|---|---|---|---|
| 8-3 | 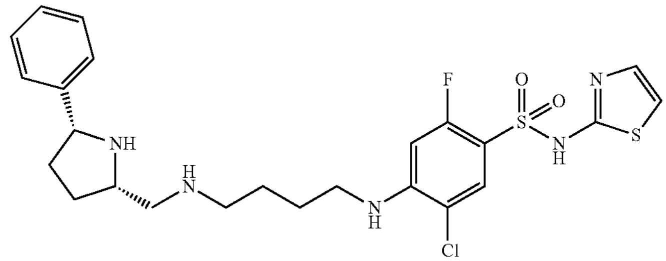 [SMILES: O=S(=O)(Nc1nccs1)c1cc(Cl)c(NCCCCNC[C@@H]2CC[C@H](c3ccccc3)N2)cc1F] | 5-chloro-2-fluoro-4-{[4-({[(2S,5R)-5-phenylpyrrolidin-2-yl]methyl}-amino)butyl]-amino}-N-1,3-thiazol-2-yl-benzenesulfonamide | Calc'd 538.2, found 538.3 |
| 8-4 | 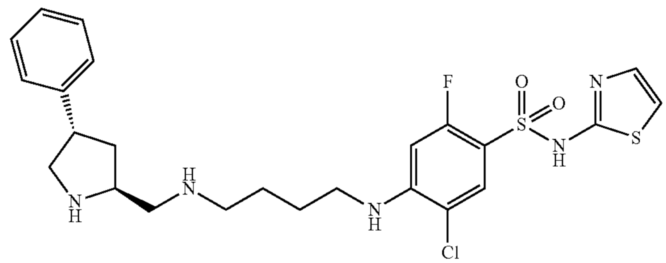 [SMILES: O=S(=O)(Nc1nccs1)c1cc(Cl)c(NCCCCNC[C@@H]2C[C@@H](c3ccccc3)CN2)cc1F] | 5-chloro-2-fluoro-4-{[4-({[(2S,4S)-4-phenyl-pyrrolidin-2-yl]methyl}-amino)butyl]amino}-N-1,3-thiazol-2-yl-benzenesulfonamide | Calc'd 538.2, found 538.3 |
| 8-5 | 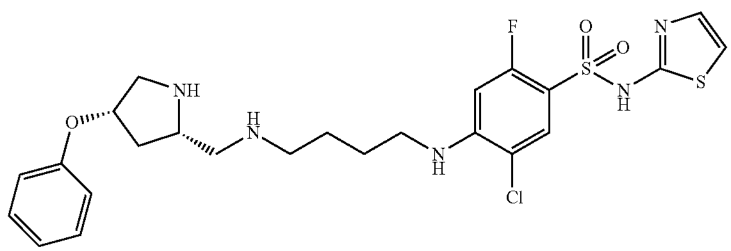 [SMILES: O=S(=O)(Nc1nccs1)c1cc(Cl)c(NCCCCNC[C@@H]2C[C@H](Oc3ccccc3)CN2)cc1F] | 5-chloro-2-fluoro-4-{[4-({[(2S,4S)-4-phenoxypyrrolidin-2-yl]methyl}amino)butyl]-amino}-N-1,3-thiazol-2-yl-benzenesulfonamide | Calc'd 554.1, found 554.3 |
| 8-6 | 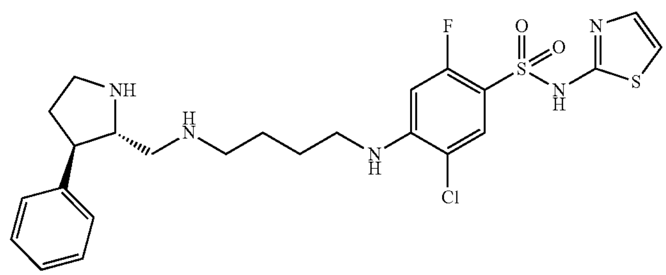 [SMILES: O=S(=O)(Nc1nccs1)c1cc(Cl)c(NCCCCNC[C@H]2NCC[C@@H]2c2ccccc2)cc1F] | 5-chloro-2-fluoro-4-{[4-({[(2S,3R)-3-phenylpyrrolidin-2-yl]-methyl}amino)butyl]amino}-N-1,3-thiazol-2-ylbenzenesulfonamide | Calc'd 538.2, found 538.3 |
| 8-7 | 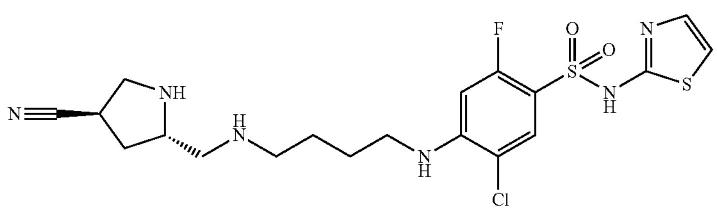 [SMILES: N#C[C@H]1CN[C@H](CNCCCCNc2cc(F)c(S(=O)(=O)Nc3nccs3)cc2Cl)C1] | 5-chloro-4-{[4-({[(2S,4R)-4-cyanopyrrolidin-2-yl]-methyl}amino)butyl]amino}-2-fluoro-N-1,3-thiazol-2-ylbenzenesulfonamide | Calc'd 487.1, found 487.3 |
| 8-11 | 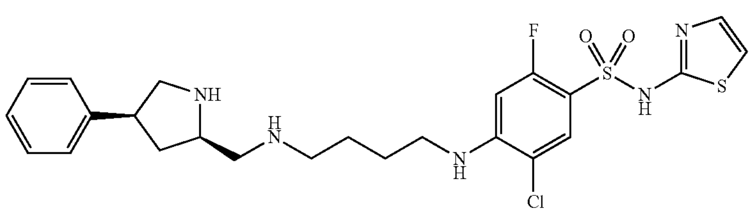 [SMILES: O=S(=O)(Nc1nccs1)c1cc(Cl)c(NCCCCNC[C@H]2C[C@@H](c3ccccc3)CN2)cc1F] | 5-chloro-2-fluoro-4-{[4-({[(2R,4S)-4-phenylpyrrolidin-2-yl]-methyl}amino)butyl]amino}-N-1,3-thiazol-2-yl-benzenesulfonamide | Calc'd 538.2, found 538.3 |

TABLE 6-continued

| Example | Structure | IUPAC Name | LC/MS [M + H]+ |
|---|---|---|---|
| 8-13 | 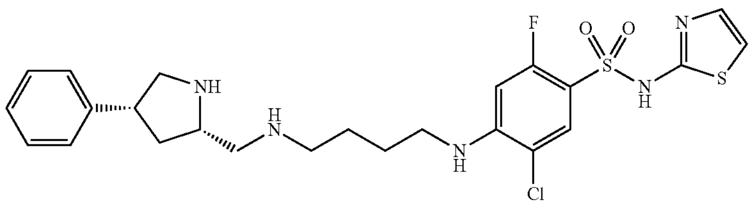 [SMILES: O=S(=O)(Nc1nccs1)c1cc(Cl)c(NCCCCNC[C@@H]2C[C@H](c3ccccc3)CN2)cc1F] | 5-chloro-2-fluoro-4-{[4-({[(2S,4R)-4-phenylpyrrolidin-2-yl]-methyl}amino)-butyl]amino}-N-1,3-thiazol-2-yl-benzenesulfonamide | Calc'd 538.2, found 538.3 |
| 8-14 | 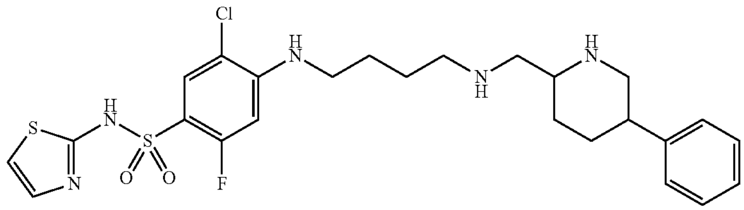 [SMILES: O=S(=O)(Nc1nccs1)c1cc(Cl)c(NCCCCNCC2CCC(c3ccccc3)CN2)cc1F] | 5-chloro-2-fluoro-4-[(4-{[(5-phenyl-piperidin-2-yl)-methyl]amino}butyl)amino]-N-1,3-thiazol-2-yl-benzenesulfonamide | Calc'd 552.2, found 552.3 |
| 8-15 | 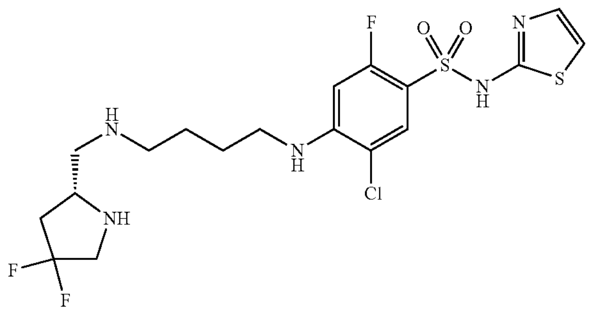 [SMILES: O=S(=O)(Nc1nccs1)c1cc(Cl)c(NCCCCNC[C@H]2CC(F)(F)CN2)cc1F] | 5-chloro-4-{[4-({[(2R)-4,4-difluoropyrrolidin-2-yl]-methyl}amino)butyl]amino}-2-fluoro-N-1,3-thiazol-2-yl-benzenesulfonamide | Calc'd 498.1, found 498.3 |
| 8-16 | 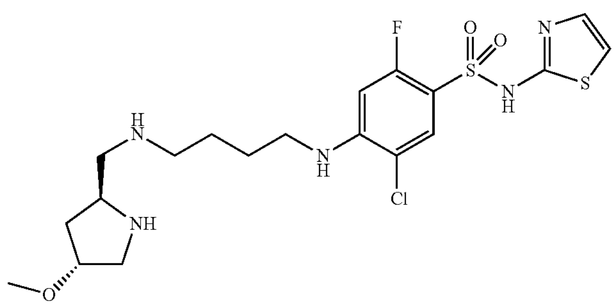 [SMILES: CO[C@H]1CN[C@H](CNCCCCNc2cc(F)c(S(=O)(=O)Nc3nccs3)cc2Cl)C1] | 5-chloro-2-fluoro-4-{[4-({[(2S,4R)-4-methoxypyrrolidin-2-yl-methyl}amino)butyl]amino}-N-1,3-thiazol-2-yl-benzenesulfonamide | Calc'd 492.1, found 492.3 |

Example 9: (S)-5-chloro-2-fluoro-N-(6-fluoropyridin-2-yl)-4-((5-((pyrrolidin-2-ylmethyl)amino)pentyl)amino)benzenesulfonamide (9-2)

Scheme 9

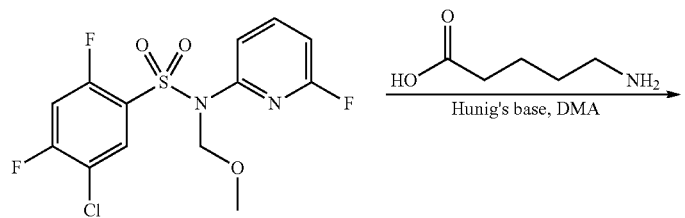

Intermediate 2

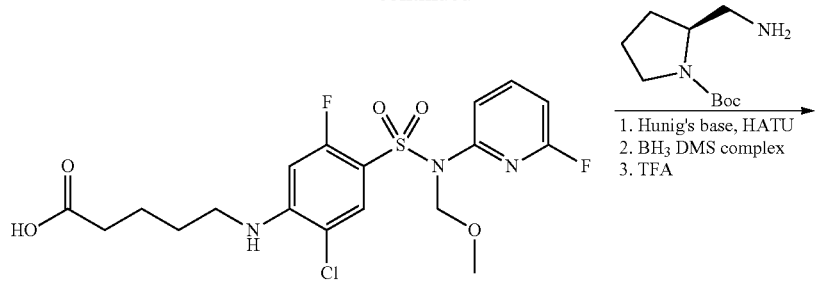

5-((2-chloro-5-fluoro-4-(N-(6-fluoropyridin-2-yl)-N-(methoxymethyl)sulfamoyl)-phenyl)amino)pentanoic acid (9-1)

Into a DMA (10 mL) solution of Intermediate 2 (1.25 g, 3.41 mmol) and Hunig's Base (2.4 mL, 13.74 mmol) was added 5-aminopentanoic acid (0.45 g, 3.84 mmol). The mixture was stirred under a nitrogen balloon at 60° C. overnight. The solution was cooled to room temperature to afford the crude title compound, which was used without further purification. LRMS m/z (M-OCH$_3$) 432.0 found, 432.1 required.

(S)-5-chloro-2-fluoro-N-(6-fluoropyridin-2-yl)-4-((5-((pyrrolidin-2-ylmethyl)amino)pentyl)amino) benzenesulfonamide (9-2)

To the DMA solution from 9-1 (1 mL, ca. 0.27 mmol) was added (S)-tert-butyl 2-(aminomethyl)pyrrolidine-1-carboxylate (67.6 mg, 0.338 mmol) and HATU (144 mg, 0.378 mmol). The solution was stirred overnight and then partitioned between EtOAc and 1 N HCl aq. The organic phase was washed with 1N HCl, brine and dried over MgSO$_4$. The solution was then filtered and concentrated. To the crude material was added THF (1.4 mL) and borane dimethyl sulfide complex (0.21 mL, 2.16 mmol). The reaction solution was then stirred under a nitrogen balloon overnight. Excess MeOH was added (dropwise) and the solution was then heated at 55° C. for ca. 4 hours. The solution was concentrated and treated with DCM/TFA (1:1) for 1 hour at room temperature. The solution was concentrated and the residue purified by prep-HPLC to give the title compound. $^1$H NMR (500 MHz, CD$_3$OD): δ 7.74 (d; J=7.3 Hz; 1H); 7.52 (q; J=8.3 Hz; 1H); 6.76 (dd; J=8.0; 2.2 Hz; 1H); 6.39 (d; J=12.8 Hz; 1H); 6.30 (dd; J=7.9; 2.4 Hz; 1H); 3.61-3.67 (m; 1H); 3.10-3.21 (m; 4H); 2.87-2.91 (m; 2H); 2.61-2.81 (m; 2H); 2.07-2.16 (m; 1H); 1.93-2.03 (m; 2H); 1.49-1.64 (m; 4H); 1.35-1.41 (m; 3H). LRMS m/z (M+H) 488.2 found, 488.2 required.

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE 7

| Example | Structure | Name | LC/MS [M + H]+ |
| --- | --- | --- | --- |
| 9-3 | 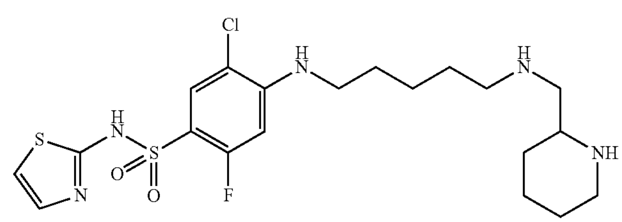 [SMILES: O=S(=O)(Nc1nccs1)c1cc(Cl)c(NCCCCCNCC2CCCCN2)cc1F] | 5-chloro-2-fluoro-4-({5-[(piperidin-2-ylmethyl)-amino]pentyl}amino)-N-1,3-thiazol-2-yl-benzenesulfonamide | Calc'd 490.2, found 490.1 |

TABLE 7-continued

| Example | Structure | Name | LC/MS [M + H]+ |
|---|---|---|---|
| 9-4 | 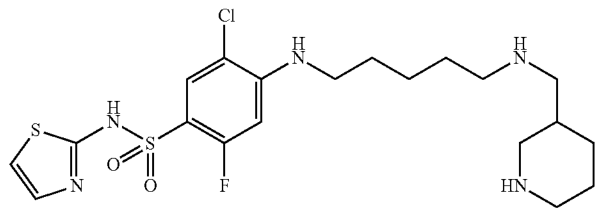 [SMILES: O=S(=O)(Nc1nccs1)c1cc(Cl)c(NCCCCCNCC2CCCNC2)cc1F] | 5-chloro-2-fluoro-4-({5-[(piperidin-3-ylmethyl)-amino]-pentyl}amino)-N-1,3-thiazol-2-yl-benzenesulfonamide | Calc 'd 490.2, found 490.14 |
| 9-5 | 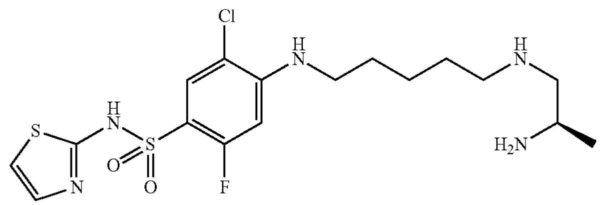 [SMILES: C[C@@H](N)CNCCCCCNc1cc(F)c(S(=O)(=O)Nc2nccs2)cc1Cl] | 4-[(5-{[(2R)-2-aminopropyl]-amino}penty)amino]-5-chloro-2-fluoro-N-1,3-thiazol-2-yl-benzenesulfonamide | Calc'd 450.1, found 450.11 |
| 9-6 | 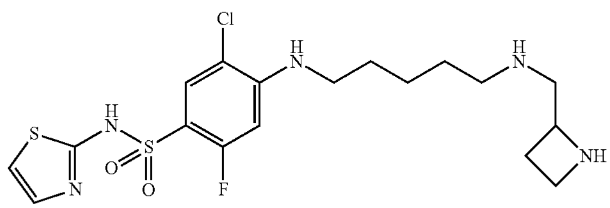 [SMILES: O=S(=O)(Nc1nccs1)c1cc(Cl)c(NCCCCCNCC2CCN2)cc1F] | 4-({5-[(azetidin-2-ylmethyl)amino]-pentyl}amino)-5-chloro-2-fluoro-N-1,3-thiazol-2-yl-benzenesulfonamide | Calc'd 462.1, found 462.11 |

Example 10: 5-chloro-2-fluoro-4-((2-phenyl-4-(((S)-pyrrolidin-2-ylmethyl)amino)butyl)amino)-N-(thiazol-2-yl)benzenesulfonamide (10-3)

Scheme 10

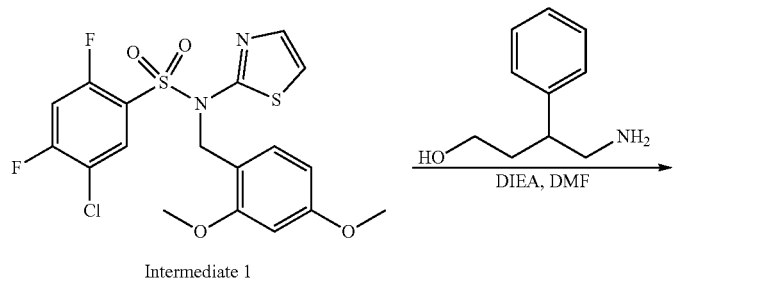

Intermediate 1

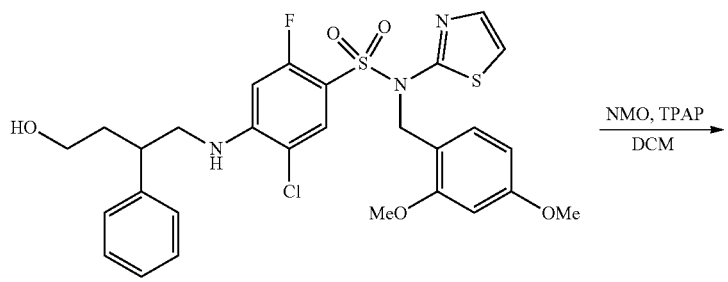

10-1

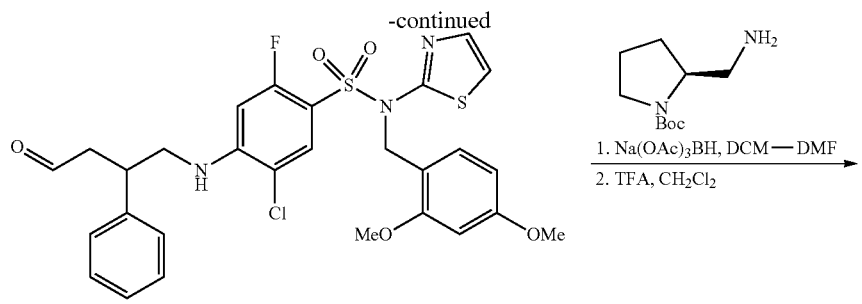

10-2

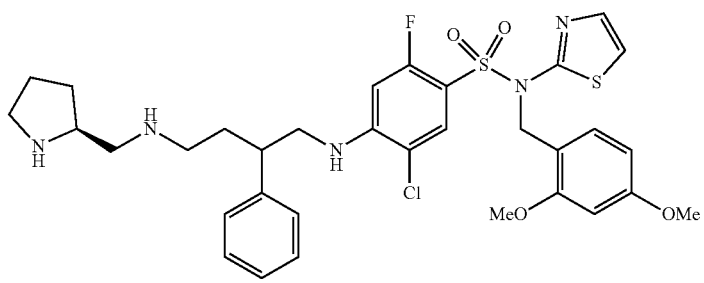

10-3

5-chloro-N-(2,4-dimethoxybenzyl)-2-fluoro-4-((4-hydroxy-2-phenylbutyl)amino)-N-(thiazol-2-yl)benzenesulfonamide (10-1)

To the stirred solution of 5-chloro-N-(2,4-dimethoxybenzyl)-2,4-difluoro-N-(thiazol-2-yl)benzenesulfonamide (Intermediate 1, 1.00 g, 2.17 mmol) and 4-amino-3-phenylbutan-1-ol (358 mg, 2.17 mmol) in DMF (5 ml) was added DIEA (0.568 ml, 3.25 mmol). The mixture was stirred at 50° C. overnight, then cooled to room temperature, concentrated and purified by chromatography (Isco CombiFlash, 120 g RediSep silica gel gold column, and 0-100% EtOAc in hexane as eluent) to give the desired product. LCMS m/z (M+H) calc'd: 606.12; found: 606.17.

5-chloro-N-(2,4-dimethoxybenzyl)-2-fluoro-4-((4-oxo-2-phenylbutyl)amino)-N-(thiazol-2-yl)benzenesulfonamide (10-2)

To the stirred solution of 5-chloro-N-(2,4-dimethoxybenzyl)-2-fluoro-4-((4-hydroxy-2-phenylbutyl)amino)-N-(thiazol-2-yl)benzenesulfonamide (10-1, 100 mg, 0.165 mmol) in DCM (1.65 ml) was added NMO (23 mg, 0.20 mmol), molecular sieve (4 Å, 100 mg) and then TPAP (5.8 mg, 0.016 mmol). The mixture was stirred at room temperature for 2 h, filtered and purified by chromatography (Isco CombiFlash, 40 g RediSep silica gel gold column, and 0-100% EtOAc in hexane as eluent to give the desired product (10-2). LCMS m/z (M+H) calc'd: 604.11; found: 604.74.

5-chloro-2-fluoro-4-((2-phenyl-4-(((S)-pyrrolidin-2-ylmethyl)amino)butyl)amino)-N-(thiazol-2-yl)benzenesulfonamide (10-3)

To the stirred suspension of 5-chloro-N-(2,4-dimethoxybenzyl)-2-fluoro-4-((4-oxo-2-phenylbutyl)amino)-N-(thiazol-2-yl)benzenesulfonamide (35 mg, 0.058 mmol) and (S)-tert-butyl 2-(aminomethyl)pyrrolidine-1-carboxylate (13 mg, 0.064 mmol) in DMF (0.5 ml) were added DIEA (10 μl, 0.058 mmol) and sodium triacetoxyborohydride (37 mg, 0.17 mmol). The mixture was stirred at room temperature for 2 h, then was added TFA (1 ml). The mixture was stirred at room temperature for additional 2 h, concentrated, and purified by Mass Directed Reverse HPLC (30×250 mm, Waters Sunfire C18 column, 5 t particle size, linear gradient (8% ACN/H2O to 29% ACN/H2O buffering with 0.1% TFA)). The product was collected after evaporation of the solvent. LCMS m/z (M+H) calc'd: 538.14; found: 538.10. $^1$H NMR (500 MHz, CD$_3$OD): δ 7.65 (dd, J=7.0 Hz, J=11.5 Hz, 1H); 7.37-7.24 (m, 5H); 7.11 (dd, J=5.0 Hz, J=11.5 Hz, 1H); 6.73 (dd, J=5.0 Hz, J=11.5 Hz, 1H); 6.50 (t, J=11.5 Hz, 1H); 3.81 (s, br, 1H); 3.60-3.50 (m, 1H); 3.45-3.40 (m, 1H); 3.38-3.28 (m, 4H); 3.03 (s, br, 2H); 2.80 (s, br, 1H); 2.30-1.95 (m, 4H); 1.75 (m, 1H); 1.39-1.35 (m, 1H).

Example 11: 5-chloro-4-[(2,2-difluoro-4-{[(2S)-pyrrolidin-2-ylmethyl]amino}butyl)amino]-2-fluoro-N-1,3-thiazol-2-ylbenzenesulfonamide (11-11) and 5-chloro-4-[(2,2-difluoro-4-{[(2R)-pyrrolidin-2-ylmethyl]amino}butyl)amino]-2-fluoro-N-1,3-thiazol-2-ylbenzenesulfonamide (11-12)
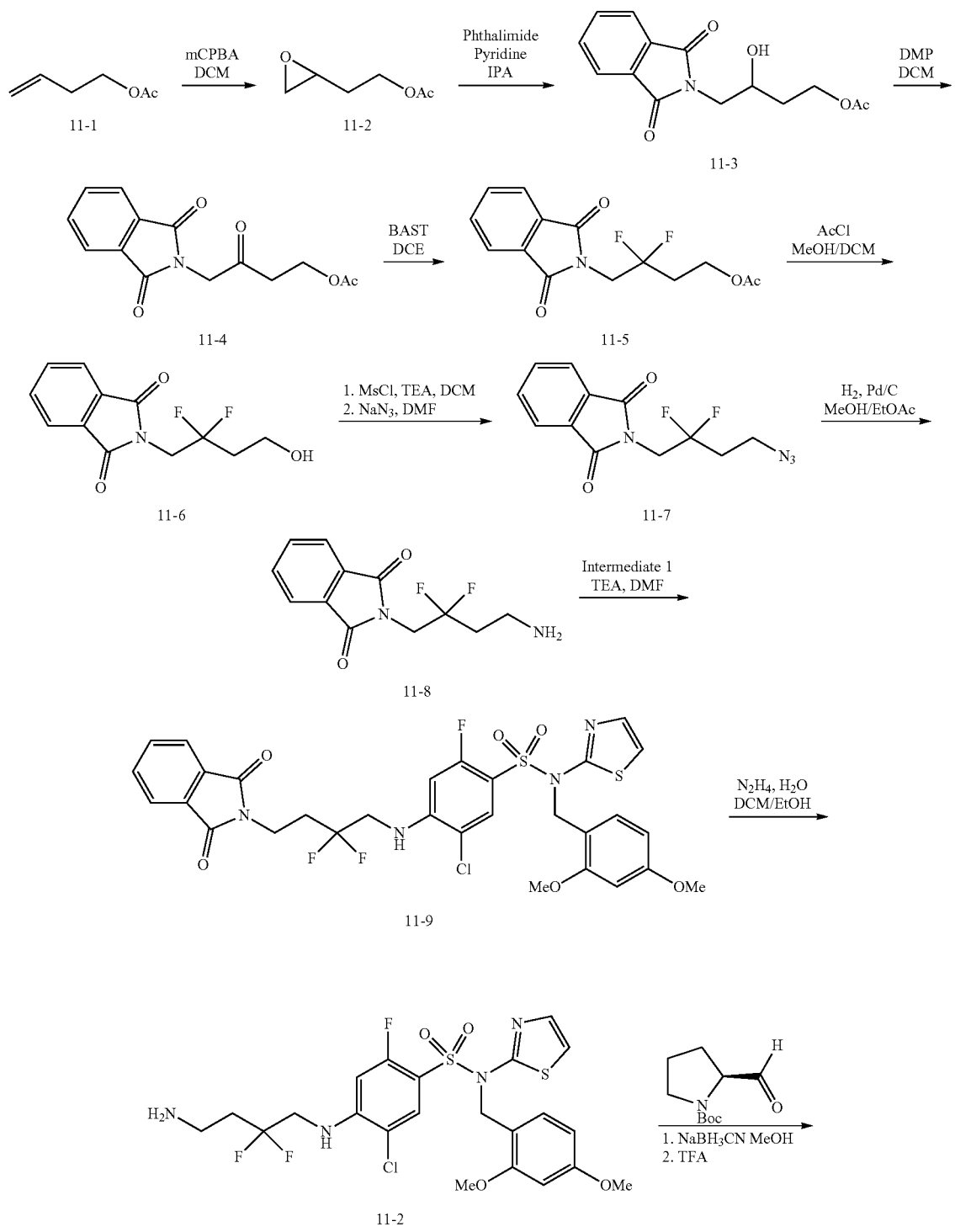

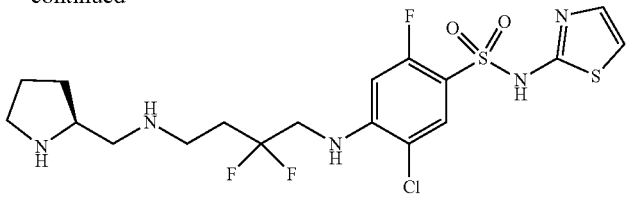

11-11

2-(oxiran-2-yl)ethyl acetate (11-2)

To a solution of but-3-en-1-yl acetate 11-1 (61 g, 534 mmol) in DCM (700 ml) was added m-CPBA (184 g, 1070 mmol) in several portions at 0° C. The reaction was then stirred at 15° C. for 5 hours. The reaction mixture was then filtered through celite and the solvent was washed with sat. $Na_2CO_3$, dried over $Na_2SO_4$, filtered and the solvent was concentrated to dryness. The residue was purified by column chromatography on silica gel (PE: EA=50: 1-10:1) to give the title compound as an oil. $^1H$ NMR ($CDCl_3$, 400 MHz) δ 4.21 (t, J 6.4 Hz, 2H), 3.01-3.00 (m, 1H), 2.78 (t, J 4.4 Hz, 1H), 2.51-2.50 (m, 1H), 2.06 (s, 3H), 1.91-1.89 (m, 1H), 1.82-1.80 (m, 1H).

4-(1,3-dioxoisoindolin-2-yl)-3-hydroxybutyl acetate (11-3)

To a solution of 2-(oxiran-2-yl)ethyl acetate 11-2 (32 g, 246 mmol) in iPrOH (150 ml) was added isoindoline-1,3-dione (54.3 g, 369 mmol), followed by pyridine (3.98 ml, 49.2 mmol). The mixture was then heated to 80° C. and stirred for 8 hours. The mixture was concentrated in vacuo and the residue was dissolved in EtOAc (600 mL), washed with 15% NaOH (50 mL*2), 1H HCl (50 mL*3), water (50 mL), brine (50 mL), dried over $Na_2SO_4$, filtered and concentrated in vacuo to give the title compound. $^1H$ NMR ($CDCl_3$, 400 MHz) δ 7.88 (dd, J 5.2, 3.2 Hz, 2H), 7.75 (dd, J 5.2, 3.2 Hz, 2H), 4.35-4.33 (m, 1H), 4.24-4.21 (m, 1H), 4.03-4.02 (m, 1H), 3.83-3.81 (m, 2H), 2.77 (t, J 5.2 Hz, 1H), 2.07 (s, 3H), 1.91-1.89 (m, 1H), 1.78-1.75 (m, 1H).

4-(1,3-dioxoisoindolin-2-yl)-3-oxobutyl acetate (11-4)

To a solution of 4-(1,3-dioxoisoindolin-2-yl)-3-hydroxybutyl acetate 11-3 (11.0 g, 39.7 mmol) in DCM (150 ml) at 0° C. was added DMP (25.2 g, 59.5 mmol). The mixture was allowed to warm to 15° C. for 3 h. The reaction progress was followed by TLC. The reaction mixture was filtered and the filtrate was washed with sat. $Na_2SO_3$ (50 mL*2), concentrated under reduced pressure. The residue was purified by column chromatography on silica gel (PE:EA=3:1 to 1:2) to give the title compound as a solid. $^1H$ NMR ($CDCl_3$, 400 MHz) δ 7.86 (dd, J=5.2, 3.2 Hz, 2H), 7.73 (dd, J=5.2, 3.2 Hz, 2H), 4.51 (s, 2H), 4.36 (t, J=6.4 Hz, 2H), 2.86 (t, J=6.4 Hz, 2H), 2.05 (s, 3H).

4-(1,3-dioxoisoindolin-2-yl)-3,3-difluorobutyl acetate (11-5)

To a mixture of 4-(1,3-dioxoisoindolin-2-yl)-3-oxobutyl acetate 11-4 (10.0 g, 36.3 mmol) in DCE (150 mL) was added BAST (56.3 g, 254 mmol) at 0° C. The mixture was stirred at 15° C. under $N_2$ for 16 h, then at 50° C. for 4 h. The reaction progress was followed by TLC. The mixture was cooled to 0° C., quenched by addition of sat. $NaHCO_3$ (100 mL) slowly. The mixture was extracted with DCM (100 mL*3). The combined organic phases were dried with $Na_2SO_4$, filtered and the filtrate was concentrated. The residue was purified by column chromatography on silica gel (PE:EA=4:1 to 1:1) to give the title compound. $^1H$ NMR ($CDCl_3$, 400 MHz) δ 7.91 (dd, J=5.2, 3.2 Hz, 2H), 7.78 (dd, J=5.2, 3.2 Hz, 2H), 4.41 (t, J=6.8 Hz, 2H), 4.17 (t, J=13.6 Hz, 2H), 2.41-2.33 (m, 2H), 2.14 (s, 3H).

2-(2,2-difluoro-4-hydroxybutyl)isoindoline-1,3-dione (11-6)

To a solution of 4-(1,3-dioxoisoindolin-2-yl)-3,3-difluorobutyl acetate 11-5 (6.0 g, 20 mmol) in MeOH/DCM (80 mL/16 mL) was added AcCl (0.72 ml, 10 mmol), and the mixture was stirred at 15° C. for 12 h. The reaction was monitored by TLC. The reaction was quenched by addition of sat. $NaHCO_3$ (20 mL) and then extracted with DCM (30 mL*3). The combined organic layers were dried with $Na_2SO_4$, filtered and concentrated to give the title compound. $^1H$ NMR ($CDCl_3$, 400 MHz) δ 7.90 (dd, J=5.2, 3.2 Hz, 2H), 7.77 (dd, J=5.2, 3.2 Hz, 2H), 4.19 (t, J=14.0 Hz, 2H), 3.95 (t, J=6.0 Hz, 2H), 2.28-2.18 (m, 2H).

2-(4-azido-2,2-difluorobutyl)isoindoline-1,3-dione (11-7)

To a solution of 2-(2,2-difluoro-4-hydroxybutyl)isoindoline-1,3-dione 11-6 (450 mg, 1.76 mmol) in $CH_2Cl_2$ (10 ml) at 0° C. was added $Et_3N$ (0.737 ml, 5.29 mmol), followed by MsCl (0.206 ml, 2.64 mmol). The mixture was stirred for 1 h at this temperature and then quenched by addition of water (10 mL). The mixture was extracted with DCM (10 mL*3) and the combined organic layers were dried with $Na_2SO_4$, filtered and concentrated to give crude 4-(1,3-dioxoisoindolin-2-yl)-3,3-difluorobutyl methanesulfonate, which was used directly in the next step without further purification. LRMS m/z (M+Na) 356.0 found, 356.1 calc'd. A mixture of 4-(1,3-dioxoisoindolin-2-yl)-3,3-difluorobutyl methanesulfonate (580 mg, 1.740 mmol) and $NaN_3$ (566 mg, 8.70 mmol) in DMF (10 ml) was stirred at 80° C. for 6 h under $N_2$. EtOAc (40 mL) then was added to the reaction mixture and the mixture was filtered. The filtrate was washed with water (5 mL*2), brine (4 mL), dried with $Na_2SO_4$, filtered and concentrated. The crude product was purified by column chromatography on silica gel (PE:EA=5:1) to give the title compound. $^1H$ NMR ($CDCl_3$, 400 MHz) δ 7.92 (dd, J 5.2, 3.2 Hz, 2H), 7.79 (dd, J 5.2, 3.2 Hz, 2H), 4.12 (t, J 13.6 Hz, 2H), 3.59 (t, J 7.2 Hz, 2H), 2.25-2.20 (m, 2H).

2-(4-amino-2,2-difluorobutyl)isoindoline-1,3-dione (11-8)

A mixture of 2-(4-azido-2,2-difluorobutyl)isoindoline-1,3-dione 11-7 (410 mg, 1.46 mmol) and 10% Pd—C (31.1 mg, 0.293 mmol) in MeOH/EtOAc (10 mL/2 mL) was stirred under H$_2$ for 3 h at 15° C. The mixture was filtered and the filtrate was concentrated to give the title compound, which was used directly in the next step without further purification. $^1$H NMR (CDCl$_3$, 400 MHz) δ 7.86 (dd, J 5.2, 3.2 Hz, 2H), 7.73 (dd, J 5.2, 3.2 Hz, 2H), 3.94 (t, J 7.6 Hz, 2H), 3.02 (t, J 14.4 Hz, 2H), 2.37-2.27 (m, 2H).

5-chloro-N-(2,4-dimethoxybenzyl)-4-((4-(1,3-di-oxoisoindolin-2-yl)-2,2-difluorobutyl)amino)-2-fluoro-N-(thiazol-2-yl)benzenesulfonamide (11-9)

A mixture of 2-(4-amino-2,2-difluorobutyl)isoindoline-1,3-dione 11-8 (370 mg, 1.45 mmol), 5-chloro-N-(2,4-dimethoxybenzyl)-2,4-difluoro-N-(thiazol-2-yl)benzenesulfonamide Intermediate 1 (738 mg, 1.60 mmol) and Et$_3$N (1.01 ml, 7.28 mmol) in 5 mL of DMF was stirred at 40° C. for 12 h. The reaction progress was followed by LCMS and TLC. The mixture was poured into water (15 mL), extracted with EtOAc (10 mL*3). The combined organic layers were dried over Na$_2$SO$_4$, filtered and concentrated. The residue was purified by column chromatography on silica gel (PE:EA=3:1 to 1:1) to give a mixture of 5-chloro-N-(2,4-dimethoxybenzyl)-4-((4-(1,3-dioxoisoindolin-2-yl)-3,3-difluorobutyl)amino)-2-fluoro-N-(thiazol-2-yl)benzenesulfonamide and 5-chloro-N-(2,4-dimethoxybenzyl)-4-((4-(1,3-dioxoisoindolin-2-yl)-2,2-difluorobutyl)amino)-2-fluoro-N-(thiazol-2-yl)benzenesulfonamide 11-9. LRMS m/z (M+H) 695.1 found, 695.1 calc'd.

4-((4-amino-2,2-difluorobutyl)amino)-5-chloro-N-(2,4-dimethoxybenzyl)-2-fluoro-N-(thiazol-2-yl)benzenesulfonamide (11-10)

To a mixture of 5-chloro-N-(2,4-dimethoxybenzyl)-4-((4-(1,3-dioxoisoindolin-2-yl)-3,3-difluorobutyl)amino)-2-fluoro-N-(thiazol-2-yl)benzenesulfonamide and 5-chloro-N-(2,4-dimethoxybenzyl)-4-((4-(1,3-dioxoisoindolin-2-yl)-2,2-difluorobutyl)amino)-2-fluoro-N-(thiazol-2-yl)benzenesulfonamide 11-9 (400 mg, 0.575 mmol) in EtOH (6 ml) and CH$_2$Cl$_2$ (2 ml) was added hydrazine (0.085 ml, 2.3 mmol), and the mixture was stirred at 40° C. for 8 h. The reaction was followed by LCMS. The mixture was cooled and filtered. The filtrate was concentrated to give a mixture of 4-((4-amino-3,3-difluorobutyl)amino)-5-chloro-N-(2,4-dimethoxybenzyl)-2-fluoro-N-(thiazol-2-yl)benzenesulfonamide and 4-((4-amino-2,2-difluorobutyl)amino)-5-chloro-N-(2,4-dimethoxybenzyl)-2-fluoro-N-(thiazol-2-yl)benzenesulfonamide 11-10, which was directly used in the next step without further purification. LRMS m/z (M+H) 565.2 found, 565.1 calc'd.

(S)-5-chloro-4-((2,2-difluoro-4-((pyrrolidin-2-ylmethyl)amino)butyl)amino)-2-fluoro-N-(thiazol-2-yl)benzenesulfonamide (11-11)

To a mixture of 4-((4-amino-3,3-difluorobutyl)amino)-5-chloro-N-(2,4-dimethoxybenzyl)-2-fluoro-N-(thiazol-2-yl)benzenesulfonamide and 4-((4-amino-2,2-difluorobutyl)amino)-5-chloro-N-(2,4-dimethoxybenzyl)-2-fluoro-N-(thiazol-2-yl)benzenesulfonamide 11-10 (70 mg, 0.12 mmol) in MeOH (1 ml) were added (S)-tert-butyl 2-form-ylpyrrolidine-1-carboxylate (25 mg, 0.12 mmol) and NaCNBH$_3$ (23 mg, 0.37 mmol). The mixture was stirred at 20° C. for 30 h. The reaction progress was followed by LCMS and TLC. The reaction mixture was concentrated, and the residue was purified by prep-TLC (DCM:MeOH=10:1) to give (S)-tert-butyl 2-(((4-((2-chloro-4-(N-(2,4-dimethoxybenzyl)-N-(thiazol-2-yl)sulfamoyl)-5-fluorophenyl)amino)-3,3-difluorobutyl)amino)methyl)pyrrolidine-1-carboxylate. $^1$H NMR (CDCl$_3$, 400 MHz) δ 7.73 (d, J 6.8 Hz, 1H), 7.40 (d, J 3.6 Hz, 1H), 7.20 (d, J 8.0 Hz, 1H), 6.98 (d, J 3.2 Hz, 1H), 6.50 (d, J 12.0 Hz, 1H), 6.38-6.36 (m, 2H), 5.19 (s, 2H), 4.01 (brs, 1H), 3.76-3.70 (m, 8H), 3.49-3.44 (m, 1H), 3.34-3.31 (m, 1H), 3.08-3.05 (m, 3H), 2.89-2.85 (m, 1H), 2.38-2.16 (m, 3H), 1.88-1.83 (m, 2H), 1.68-1.63 (m, 1H), 1.46 (s, 9H). LRMS m/z (M+H) 748.2 found, 748.2 calc'd.

A mixture of give (S)-tert-butyl 2-(((4-((2-chloro-4-(N-(2,4-dimethoxybenzyl)-N-(thiazol-2-yl)sulfamoyl)-5-fluorophenyl)amino)-3,3-difluorobutyl)amino)methyl)pyrrolidine-1-carboxylate (30 mg, 0.040 mmol) in DCM/TFA (2 mL/0.5 mL) was stirred at 15° C. for 1 h. The reaction progress was followed by LCMS. The mixture was concentrated and the residue was purified by prep-HPLC (TFA) to give the title compound. $^1$H NMR (CD$_3$OD, 400 MHz) δ 7.73 (d, J 6.8 Hz, 1H), 7.12 (d, J 4.8 Hz, 1H), 6.78-6.74 (m, 2H), 3.89-3.76 (m, 3H), 3.43-3.38 (m, 6H), 2.48-2.26 (m, 3H), 2.13-2.06 (m, 2H), 1.83-1.78 (m, 1H). LRMS m/z (M+H) 498.1 found, 498.1 calc'd.

11-12

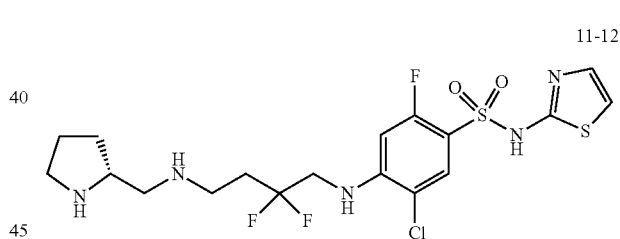

(R)-5-chloro-4-((2,2-difluoro-4-((pyrrolidin-2-ylmethyl)amino)butyl)amino)-2-fluoro-N-(thiazol-2-yl)benzenesulfonamide (11-12)

(R)-5-chloro-4-((2,2-difluoro-4-((pyrrolidin-2-ylmethyl)amino)butyl)amino)-2-fluoro-N-(thiazol-2-yl)benzenesulfonamide (11-12) was prepared from (R)-tert-butyl 2-formylpyrrolidine-1-carboxylate and 11-10 using a similar procedure to that of 11-16 reported above. $^1$H NMR (CD$_3$OD, 400 MHz) δ 7.73 (d, J 6.8 Hz, 1H), 7.12 (d, J 4.8 Hz, 1H), 6.78-6.74 (m, 2H), 3.89-3.76 (m, 3H), 3.43-3.38 (m, 6H), 2.48-2.26 (m, 3H), 2.13-2.06 (m, 2H), 1.83-1.78 (m, 1H). LRMS m/z (M+H) 498.1 found, 498.1 calc'd.

The compounds of Table 8 were prepared using the chemistry and intermediates described herein:

TABLE 8

| Exp No. | Structure | Name | LC/MS [M + H]+ |
|---|---|---|---|
| 16-02 | 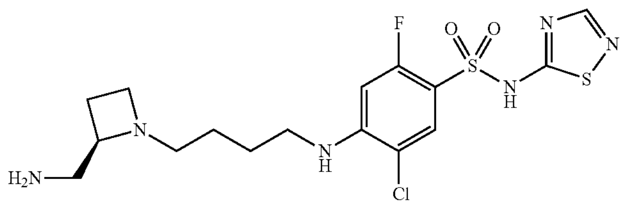 [SMILES: NC[C@H]1CCN1CCCCNc1cc(F)c(S(=O)(=O)Nc2ncns2)cc1Cl] | 4-({4-[(2R)-2-(aminomethyl)-azetidin-1-yl]butyl}amino)-5-chloro-2-fluoro-N-1,2,4-thiadiazol-5-yl-benzene-sulfonamide | Calc.449.1 Obs. 449.2 |
| 16-03 | 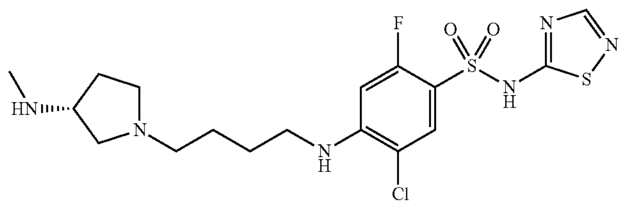 [SMILES: CN[C@@H]1CCN(CCCCNc2cc(F)c(S(=O)(=O)Nc3ncns3)cc2Cl)C1] | 5-chloro-2-fluoro-4-({4-[(3R)-3-(methylamino)pyrrolidin-1-yl]-butyl}-amino)-N-1,2,4-thiadiazol-5-ylbenzene-sulfonamide | Calc. 463.1 Obs. 462.9 |
| 16-07 | 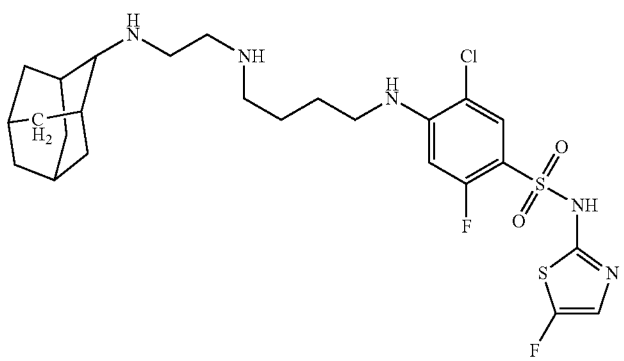 [SMILES: O=S(=O)(Nc1ncc(F)s1)c1cc(Cl)c(NCCCCNCCNC2C3CC4CC(C3)CC2C4)cc1F] | 5-chloro-2-fluoro-N-(5-fluoro-1,3-thiazol-2-yl)-4-[(4-{[2-(tricyclo[3.3.1.1~3,7~]dec-2-yl-amino)-ethyl]amino}butyl)-amino]-benzene-sulfonamide | Calc.574.1 Obs.574.1 |
| 16-10 | 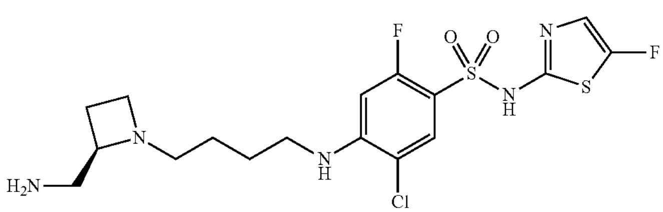 [SMILES: NC[C@H]1CCN1CCCCNc1cc(F)c(S(=O)(=O)Nc2ncc(F)s2)cc1Cl] | 4-({4-[(2R)-2-(aminomethyl)azetidin-1-yl]-butyl}amino)-5-chloro-2-fluoro-N-(5-fluoro-1,3-thiazol-2-yl)-benzene-sulfonamide | Calc.466.1 Obs. 466.2 |
| 16-11 | 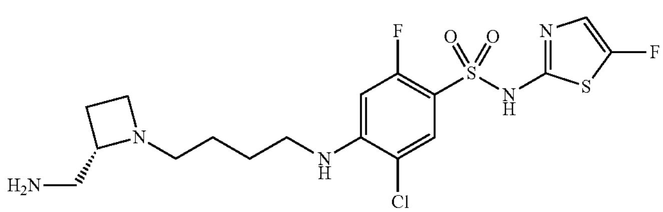 [SMILES: NC[C@@H]1CCN1CCCCNc1cc(F)c(S(=O)(=O)Nc2ncc(F)s2)cc1Cl] | 4-({4-[(2S)-2-(aminomethyl)azetidin-1-yl]-butyl}amino)-5-chloro-2-fluoro-N-(5-fluoro-1,3-thiazol-2-yl)-benzene-sulfonamide | Calc.466.1 Obs. 466.2 |
| 16-23 | 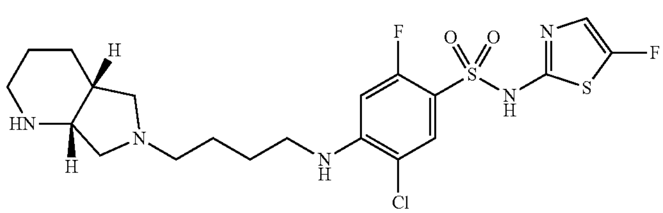 [SMILES: O=S(=O)(Nc1ncc(F)s1)c1cc(Cl)c(NCCCCN2C[C@H]3CCCN[C@H]3C2)cc1F] | 5-chloro-2-fluoro-N-(5-fluoro-1,3-thiazol-2-yl)-4-({4-[(4aR,7aR)-octahydro-6H-pyrrolo[3,4-b]pyridin-6-yl]butyl}amino)benzene-sulfonamide | Calc'd 506.1 found 506.0 |

TABLE 8-continued

| Exp No. | Structure | Name | LC/MS [M + H]+ |
|---|---|---|---|
| 16-31 | 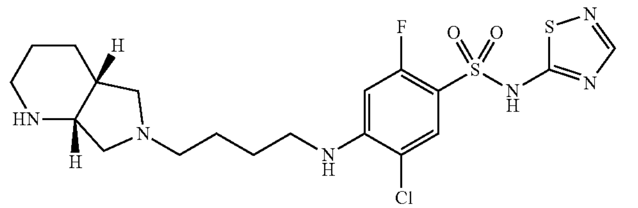 [SMILES: O=S(=O)(Nc1ncns1)c1cc(Cl)c(NCCCCN2C[C@H]3CCCN[C@H]3C2)cc1F] | 5-chloro-2-fluoro-4-({4-[(4aR,7aR)-octahydro-6H-pyrrolo[3,4-b]pyridin-6-yl]-butyl}amino)-N-1,2,4-thiadiazol-5-ylbenzene-sulfonamide | Calc'd 489.1 found 488.9 |
| 16-37 | 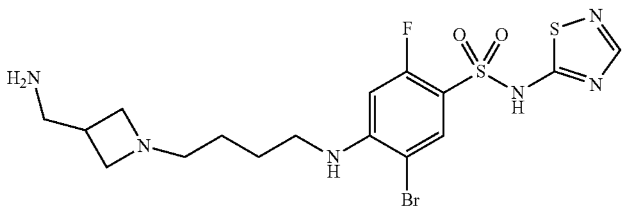 [SMILES: NCC1CN(CCCCNc2cc(F)c(S(=O)(=O)Nc3ncns3)cc2Br)C1] | 4-((4-(3-(aminomethyl)azetidin-1-yl)butyl)amino)-5-bromo-2-fluoro-N-(1,2,4-thiadiazol-5-yl)benzenesulfonamide | Calc'd 493.0 found 493.0 |
| 16-38 | 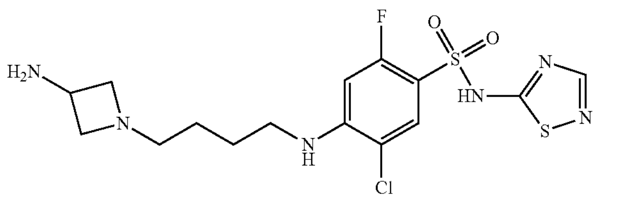 [SMILES: NC1CN(CCCCNc2cc(F)c(S(=O)(=O)Nc3ncns3)cc2Cl)C1] | 4-{[4-(3-aminoazetidin-1-yl)-butyl]amino}-5-chloro-2-fluoro-N-1,2,4-thiadiazol-5-yl-benzenesulfonamide | Calc'd 435.1 found 435.1 |
| 16-39 | 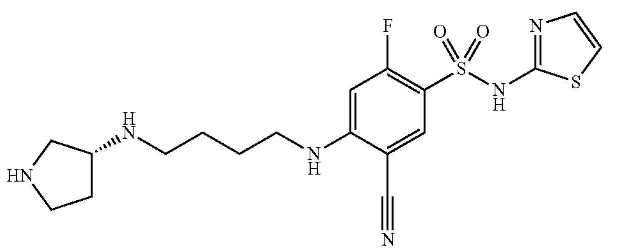 [SMILES: N#Cc1cc(S(=O)(=O)Nc2nccs2)c(F)cc1NCCCCN[C@@H]1CCNC1] | 5-cyano-2-fluoro-4-({4-[(3R)-pyrrolidin-3-ylamino]-butyl}amino)-N-1,3-thiazol-2-yl-benzenesulfonamide | Calc'd 439.1 found 439.1 |
| 16-40 | 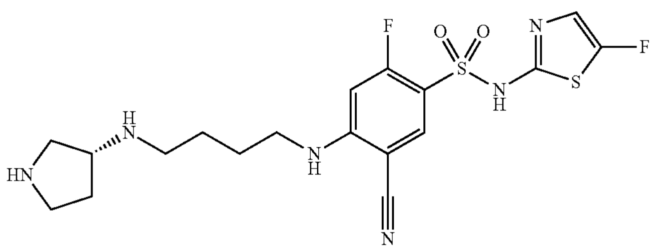 [SMILES: N#Cc1cc(S(=O)(=O)Nc2ncc(F)s2)c(F)cc1NCCCCN[C@@H]1CCNC1] | 5-cyano-2-fluoro-N-(5-fluoro-1,3-thiazol-2-yl)-4-({4-[(3R)-pyrrolidin-3-yl-amino]butyl}amino)benzene-sulfonamide | Calc'd 457.1 found 457.0 |
| 16-42 | 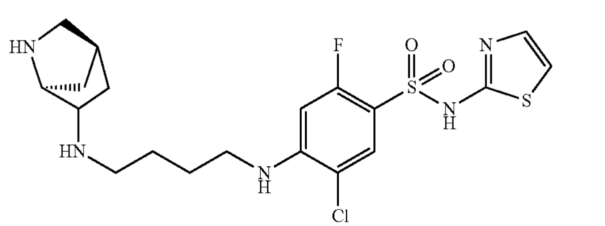 [SMILES: O=S(=O)(Nc1nccs1)c1cc(Cl)c(NCCCCNC2C[C@@H]3CN[C@H]2C3)cc1F] | 4-({4-[(1S,4R)-2-azabicyclo[2.2.1]hept-6-yl-amino]butyl}amino)-5-chloro-2-fluoro-N-1,3-thiazol-2-ylbenzene-sulfonamide | Calc'd 474.1 found 474.2 |
| 16-43 | 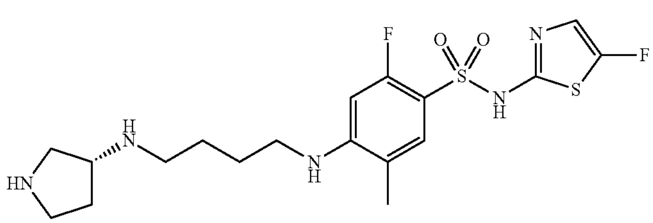 [SMILES: Cc1cc(S(=O)(=O)Nc2ncc(F)s2)c(F)cc1NCCCCN[C@@H]1CCNC1] | 2-fluoro-N-(5-fluoro-1,3-thiazol-2-yl)-5-methyl-4-({4-[(3R)-pyrrolidin-3-ylamino]-butyl}amino)benzene-sulfonamide | Calc'd 446.1 found 446.1 |

TABLE 8-continued

| Exp No. | Structure | Name | LC/MS [M + H]+ |
|---|---|---|---|
| 16-44 | 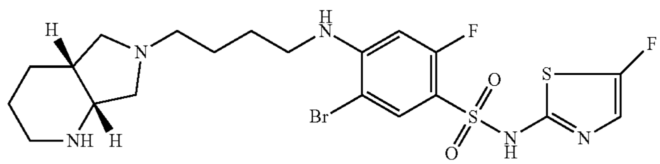 [SMILES: O=S(=O)(Nc1ncc(F)s1)c1cc(Br)c(NCCCCN2C[C@H]3CCCN[C@H]3C2)cc1F] | 5-bromo-2-fluoro-N-(5-fluoro-1,3-thiazol-2-yl)-4-({4-[(4aR,7aR)-octahydro-6H-pyrrolo[3,4-b]pyridin-6-yl]butyl}amino)benzene-sulfonamide | Calc'd 550.0, 552.0, found 550.0, 552.0 |
| 16-45 | 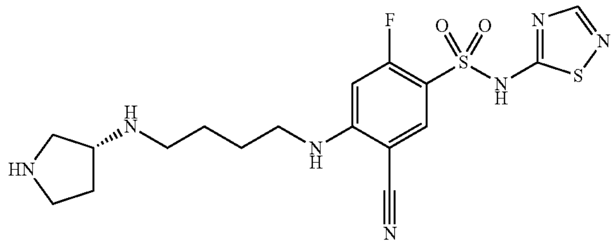 [SMILES: N#Cc1cc(S(=O)(=O)Nc2ncns2)c(F)cc1NCCCCN[C@@H]1CCNC1] | 5-cyano-2-fluoro-4-({4-[(3R)-pyrrolidin-3-yl-amino]butyl}amino)-N-1,2,4-thiadiazol-5-ylbenzene-sulfonamide | Calc'd 440.1 found 440.1 |
| 16-46 | 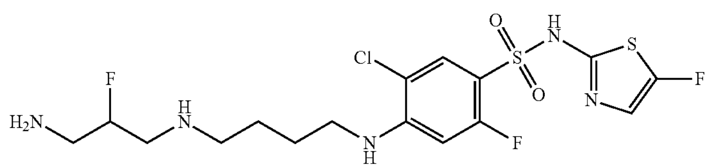 [SMILES: NCC(F)CNCCCCNc1cc(F)c(S(=O)(=O)Nc2ncc(F)s2)cc1Cl] | 4-({4-[(3-amino-2-fluoro-propyl)amino]butyl}amino)-5-chloro-2-fluoro-N-(5-fluoro-1,3-thiazol-2-yl)-benzenesulfonamide | Calc'd 472.1 found 472.1 |
| 16-47 | 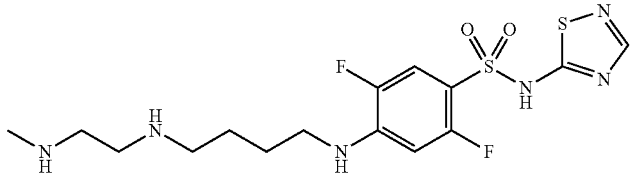 [SMILES: CNCCNCCCCNc1cc(F)c(S(=O)(=O)Nc2ncns2)cc1F] | 2,5-difluoro-4-[(4-{[2-(methylamino)ethyl]amino}-butyl)amino]-N-1,2,4-thiadiazol-5-ylbenzene-sulfonamide | Calc'd 421.1 found 421.2 |
| 16-51 | 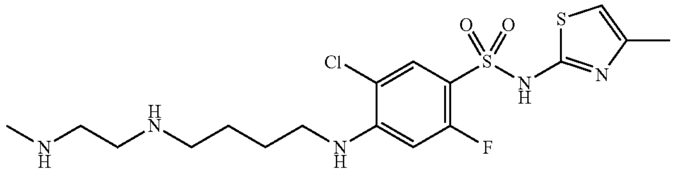 | 5-chloro-2-fluoro-4-[(4-{[2-(methylamino)ethyl]amino}-butyl)amino]-N-(4-methyl-1,3-thiazol-2-yl)benzene-sulfonamide | Calc'd 450.1 found 450.2 |
| 16-52 | 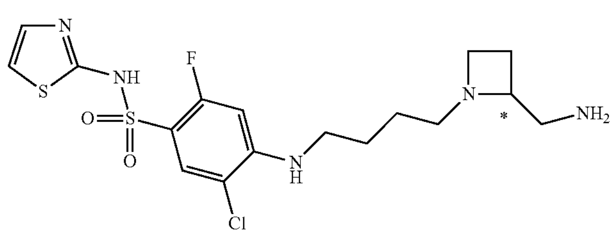 [SMILES: NCC1CCN1CCCCNc1cc(F)c(S(=O)(=O)Nc2nccs2)cc1Cl] | (R or S)-4-({4-[2-(aminomethyl)-azetidin-1-yl]butyl}amino)-5-chloro-2-fluoro-N-1,3-thiazol-2-ylbenzene-sulfonamide | Calc'd 448.1 found 448.3 |
| 16-53 | 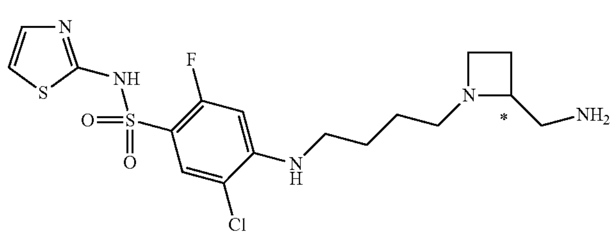 [SMILES: NCC1CCN1CCCCNc1cc(F)c(S(=O)(=O)Nc2nccs2)cc1Cl] | (S or R)-4-({4-[2-(aminomethyl)-azetidin-1-yl]butyl}amino)-5-chloro-2-fluoro-N-1,3-thiazol-2-ylbenzene-sulfonamide | Calc'd 448.1 found 448.2 |

TABLE 8-continued

| Exp No. | Structure | Name | LC/MS [M + H]+ |
|---|---|---|---|
| 16-54 | 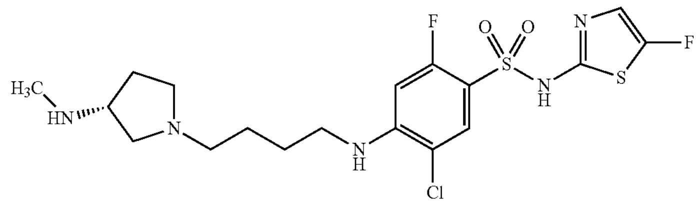 [SMILES: CN[C@@H]1CCN(CCCCNc2cc(F)c(S(=O)(=O)Nc3ncc(F)s3)cc2Cl)C1] | 5-chloro-2-fluoro-N-(5-fluoro-1,3-thiazol-2-yl)-4-({4-[(3R)-3-(methylamino)-pyrrolidin-1-yl]butyl}-amino)-benzenesulfonamide | Calc'd 480.1 found 479.9 |

Synthesis of Intermediates Useful in Preparing Compounds of the Invention

Intermediate 1: 5-chloro-N-(2,4-dimethoxybenzyl)-2,4-difluoro-N-(thiazol-2-yl)benzene sulfonamide

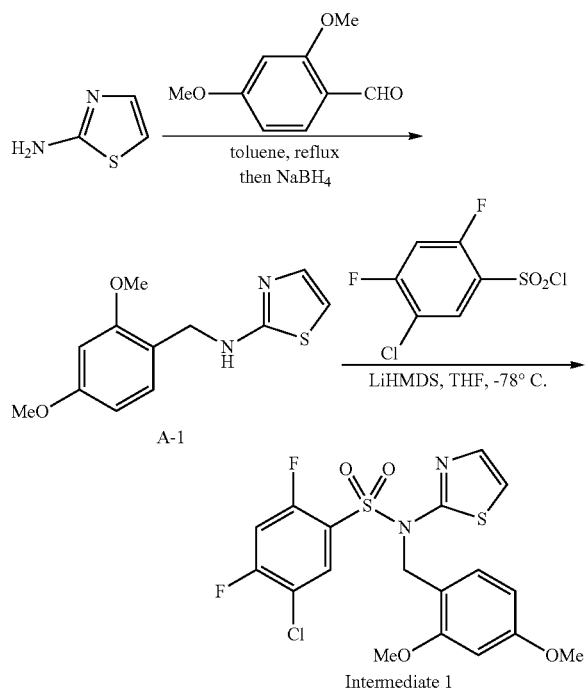

Step 1: Preparation of N-(2,4-dimethoxybenzyl)thiazol-2-amine (A-1)

A mixture of thiazol-2-amine (100 g, 1 mol) and 2,4-dimethoxybenzaldehyde (151 g, 0.91 mol) in 2 L of toluene was refluxed for 8 h with Dean-Stark apparatus to remove water. The mixture was cooled and the solvent was evaporated in vacuo. To the residue was added 3 L of MeOH and the resulting mixture was cooled to 0° C. NaBH$_4$ (151 g, 4 mol) was added carefully in portions. The mixture was then warmed to room temperature and stirred for 4 h. The mixture was quenched with water, then MeOH was evaporated in vacuo. The water layer was extracted with EtOAc and the combined organic layers were dried over Na$_2$SO$_4$, filtered and concentrated. The residue was purified by column chromatography on silica gel (PE:EtOAc=5:1 to 2:1) to give the title compound. $^1$H NMR (400 MHz, CD$_3$OD) δ 7.16 (d, J=8.4 Hz, 1H), 6.97 (d, J=4.0 Hz, 1H), 6.50-6.52 (m, 2H), 6.44 (dd, J=8.0, 2.0 Hz, 1H), 4.35 (s, 2H), 3.81 (s, 3H), 3.76 (s, 3H).

Step 2: Preparation of 5-chloro-N-(2,4-dimethoxybenzyl)-2,4-difluoro-N-(thiazol-2-yl)benzene sulfonamide (Intermediate 1)

Under an atmosphere of nitrogen, N-(2,4-dimethoxybenzyl)thiazol-2-amine A-1 (5 g, 20 mmol) was dissolved in THF (100 mL) and cooled to –78° C. LiHMDS (24 mL, 24 mmol) was added dropwise keeping the temperature below –60° C. After 30 minutes, the cooling bath was removed and the reaction was warmed to room temperature for a further 30 minutes then cooled back to –78° C. A solution of 5-chloro-2,4-difluorobenzene-1-sulfonyl chloride (5.54 g, 22.4 mmol) in THF (10 mL) was added dropwise keeping the temperature below –60° C. and the reaction mixture was warmed to room temperature. Saturated aqueous ammonium chloride solution (50 mL) was added followed by water to dissolve the solid which had precipitated out. The aqueous layer was extracted with ethyl acetate (50 mL) and the organic extracts was dried over Na$_2$SO$_4$, filtered and concentrated. The residue was purified by column chromatography on silica gel (PE:EtOAc=10:1) to give the title compound. $^1$H NMR (400 MHz, CDCl$_3$) δ 7.88-7.92 (m, 1H), 7.40 (d, J=4.0, 1H), 7.16-7.18 (m, 1H), 6.96-7.01 (m, 2H), 6.32-6.36 (m, 2H), 5.16 (s, 2H), 3.74 (s, 3H), 3.71 (s, 3H). MS m/z (M+H): 461.0

Intermediate 2: 5-chloro-2,4-difluoro-N-(6-fluoropyridin-2-yl)-N-(methoxymethyl)benzene sulfonamide (Intermediate 2)

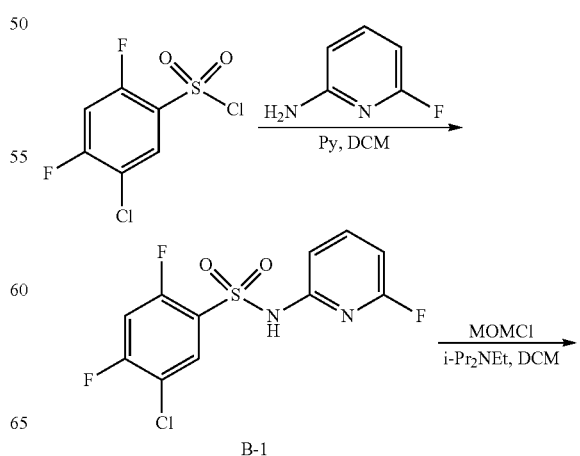

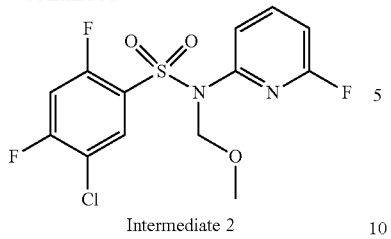

Intermediate 2

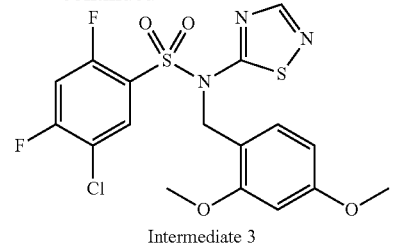

Intermediate 3

Step 1: Preparation of 5-chloro-2,4-difluoro-N-(6-fluoropyridin-2-yl)benzenesulfonamide A mixture of 5-chloro-2,4-difluorobenzene-1-sulfonyl chloride (1.3 g, 5.26 mmol), 6-fluoropyridin-2-amine (589 mg, 5.26 mmol), pyridine (2.1 g, 26.3 mmol) and DCM (20 mL) was stirred at room temperature under nitrogen overnight. $H_2O$ (20 mL) was added into the mixture which was extracted with DCM. The combined organic layers were washed with brine, dried over $Na_2SO_4$, filtered and the filtrate was concentrated. The residue was purified by column chromatography on silica gel (PE:EtOAc=5:1) to give the title compound. $^1H$ NMR (400 MHz $CD_3OD$) δ 8.16 (t, J=7.6 Hz, 1H), 7.75 (dd, J=16.0, 8.0 Hz, 1H), 7.34 (t, J=9.6 Hz, 1H), 6.89 (dd, J=8.0, 1.2 Hz, 1H), 6.60 (dd, J=8.0, 2.0 Hz, 1H).

Step 2: Preparation of 5-chloro-2,4-difluoro-N-(6-fluoropyridin-2-yl)-N-(methoxymethyl)benzenesulfonamide (Intermediate 2)

To a mixture of 5-chloro-2,4-difluoro-N-(6-fluoropyridin-2-yl)benzenesulfonamide B-1 (1 g, 3.01 mmol) in DCM (20 mL) was added DIEA (1.16 g, 9.03 mmol) and MOMCl (602 mg, 7.4 mmol). The mixture was stirred at room temperature under nitrogen for 4 h. The mixture was poured into water and extracted with DCM. The combined organic layers were washed with brine, dried over $Na_2SO_4$, filtered and the filtrate was concentrated. The residue was purified by column chromatography on silica gel (PE:EtOAc=5:1) to give the title compound. $^1H$ NMR (400 MHz $CD_3OD$) δ 8.06 (t, J=7.6 Hz, 1H), 7.91 (dd, J=16.0, 8.0 Hz, 1H), 7.35-7.41 (m, 2H), 6.85 (dd, J=8.4, 2.8 Hz, 1H), 5.35 (s, 2H), 3.42 (s, 3H). MS m/z (M+H): 367

Intermediate 3: 5-chloro-N-(2,4-dimethoxybenzyl)-2,4-difluoro-N-(1,2,4-thiadiazol-5-yl)benzenesulfonamide

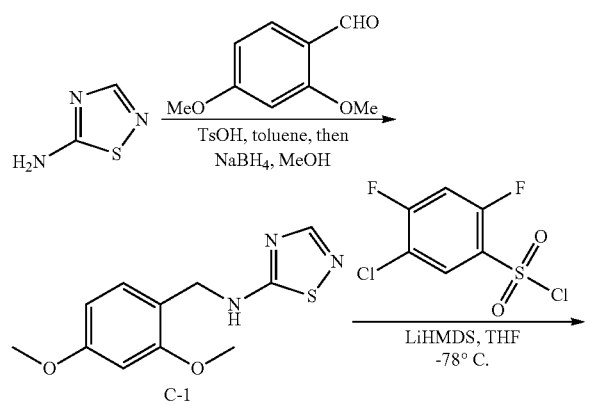

Step 1: Preparation of N-(2,4-dimethoxybenzyl)-1,2,4-thiadiazol-5-amine (C-1)

Into a 20000-mL 4-necked round-bottom flask purged and maintained with an inert atmosphere of nitrogen was placed 1,2,4-thiadiazol-5-amine (300 g, 2.97 mol), 2,4-dimethoxybenzaldehyde (472 g, 2.84 mol, 1.05 equiv), p-TsOH (4.1 g, 23.81 mmol, 0.01 equiv), toluene (9 L). The resulting solution was heated to reflux overnight with a water-separator. The reaction mixture was cooled to room temperature and concentrated under vacuum. The residue was washed with methanol. The resulting yellow solid was used crude in the next reaction. Into a 10-L 4-necked round-bottom flask purged and maintained with an inert atmosphere of nitrogen was placed a solution of the crude solid (550 g, 2.21 mol) in THF (5.5 L). This was followed by the addition of $NaBH_4$ (83 g, 2.25 mol) in several batches at 0° C. The resulting solution was stirred for 3 h at room temperature, then extracted with 3×1 L of ethyl acetate. The organic layers were combined, washed with 1×1000 mL of brine, dried over anhydrous magnesium sulfate and concentrated under vacuum. The residue was applied onto a silica gel column and eluted with dichloromethane/methanol (100:1) to give the title compound.

Step 2: Preparation of 5-chloro-N-(2,4-dimethoxybenzyl)-2,4-difluoro-N-(1,2,4-thiadiazol-5-yl)benzenesulfonamide (Intermediate 3)

To a mixture of C-1 (1.0 g, 4.0 mmol) in THF (20 mL) was added LiHMDS (5 mL, 5 mmol, 1M) at −78° C. under $N_2$. The mixture was warmed to room temperature and stirred for 1 h before cooled to −78° C. Then a solution of 5-chloro-2,4-difluorobenzene-1-sulfonyl chloride (1.2 g, 4.8 mmol) in THF (4 mL) was added dropwise. The mixture was stirred at room temperature for additional 1 h, then quenched with saturated $NH_4Cl$. The mixture was extracted with EtOAc and the combined organic phases were dried with $Na_2SO_4$, filtered and concentrated. The residue was purified by column chromatography on silica gel (PE:EtOAc=6:1) to afford the title compound. $^1H$ NMR (400 MHz, $CDCl_3$) δ 8.22 (s, 1H), 7.73 (t, J=7.6 Hz, 1H), 7.19 (d, J=8.4 Hz, 1H), 6.87 (t, J=8.4 Hz, 1H), 6.35 (dd, J=2.4, 6.0 Hz, 1H), 6.15 (d, J=2.0 Hz, 1H), 5.36 (s, 2H), 3.74 (s, 3H), 3.66 (s, 3H). MS m/z (M+H): 462.0.

The following cores were made by analogy to Intermediate 1, Intermediate 2 and Intermediate 3 using commercially available sulfonyl chlorides and heterocyclic amines or sulfonyl chlorides and amines in the published literature:

Intermediate 4: N-(2,4-dimethoxybenzyl)-2,4,5-trifluoro-N-(1,2,4-thiadiazol-5-yl)benzenesulfonamide

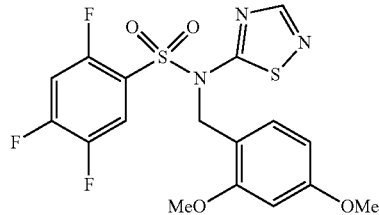

Intermediate 4

$^1$H NMR (300 MHz, d$_6$-DMSO) δ 8.47 (1H, s), 7.90-7.80 (2H, m), 7.10-7.08 (1H, d), 6.46-6.41 (1H, d), 6.35-6.34 (1H, d), 5.24 (2H, d), 3.75-3.17 (6H, d).

Intermediate 5: 5-chloro-N-(5-chlorothiazol-2-yl)-N-(2,4-dimethoxybenzyl)-2,4-difluoro benzenesulfonamide

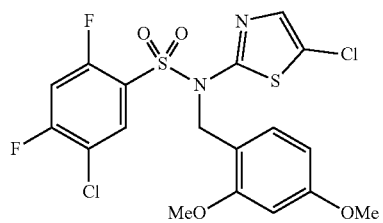

Intermediate 5

$^1$H NMR (400 MHz, CDCl$_3$) δ 7.88 (t, J=7.2 Hz, 1H), 7.24 (s, 1H), 7.18 (d, J=8.0 Hz, 1H), 7.00 (t, J=8.8 Hz, 1H), 6.37 (dd, J=8.4, 2.4 Hz, 1H), 6.32 (d, J=2.4 Hz, 1H), 5.12 (s, 2H), 3.77 (s, 3H), 3.73 (s, 3H). MS m/z (M+H): 495.

Intermediate 6: 5-chloro-N-(2,4-dimethoxybenzyl)-2,4-difluoro-N-(5-fluorothiazol-2-yl)benzenesulfonamide

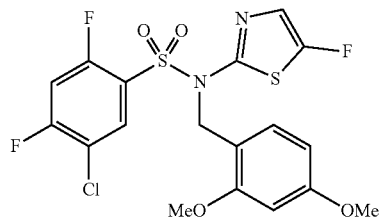

Intermediate 6

$^1$H NMR (400 MHz, CDCl$_3$) δ 7.87 (t, J=7.6 Hz, 1H), 7.16 (d, J=8.4 Hz, 1H), 7.01-7.06 (m, 2H), 6.38 (dd, J=8.4, 2.4 Hz, 1H), 6.33 (d, J=2.4 Hz, 1H), 5.04 (s, 2H), 3.77 (s, 3H), 3.72 (s, 3H). MS m/z (M+H): 479.

Intermediate 7: 3-chloro-N-(2,4-dimethoxybenzyl)-4-fluoro-N-(thiazol-2-yl)benzenesulfonamide

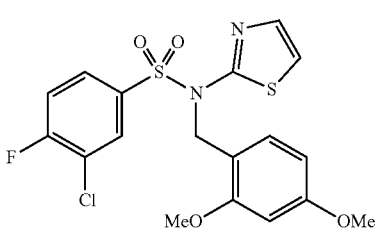

Intermediate 7

$^1$H NMR (400 MHz, CDCl$_3$) δ 7.74 (dd, J=6.8, 2.4 Hz, 1H), 7.62-7.66 (m, 1H), 7.35 (d, J=3.6 Hz, 1H), 7.12 (t, J=8.8 Hz, 1H), 7.05 (d, J=8.8 Hz, 1H), 6.97 (d, J=3.6 Hz, 1H), 6.26-6.28 (m, 2H), 4.96 (s, 2H), 3.67 (s, 3H), 3.60 (s, 3H). MS m/z (M+H): 443.

Intermediate 8: 3-chloro-N-(2,4-dimethoxybenzyl)-4-fluoro-N-(5-fluorothiazol-2-yl)benzenesulfonamide

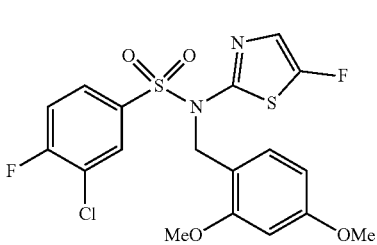

Intermediate 8

$^1$H NMR (400 MHz, CDCl$_3$) δ 7.84 (dd, J=6.8, 2.0 Hz, 1H), 7.71-7.07 (m, 1H), 7.23 (d, J=8.8 Hz, 1H), 7.12 (d, J=8.0 Hz, 1H), 7.03 (d, J=2.8 Hz, 1H), 6.39-6.36 (m, 2H), 4.89 (s, 2H), 3.78 (s, 3H), 3.70 (s, 3H). MS m/z (M+H): 461.

Intermediate 9: 5-bromo-N-(2,4-dimethoxybenzyl)-2,4-difluoro-N-(thiazol-2-yl)benzenesulfonamide

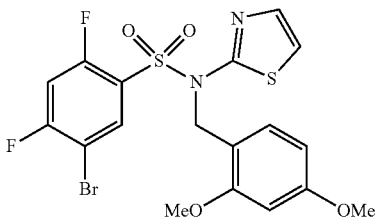

Intermediate 9

$^1$H NMR (400 MHz, CD$_3$OD) δ 8.06 (t, J=7.2 Hz, 1H), 7.43 (d, J=3.2 Hz, 1H), 7.20 (d, J=8.4 Hz, 1H), 7.03 (d, J=3.2 Hz, 1H), 6.97 (t, J=8.8 Hz, 1H), 6.38-6.34 (m, 2H), 5.18 (s, 2H), 3.77 (s, 3H), 3.73 (s, 3H). MS m/z (M+H): 505, 507.

Intermediate 10: N-(2,4-dimethoxybenzyl)-4-fluoro-N-(thiazol-2-yl)-3-(trifluoromethyl)benzenesulfonamide

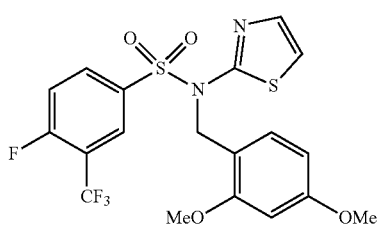

Intermediate 10

$^1$H NMR (CDCl$_3$, 400 MHz) δ 8.05-8.03 (m, 2H), 7.47 (d, J=3.6 Hz, 1H), 7.29-7.27 (m, 1H), 7.13-7.09 (m, 2H), 6.36-6.33 (m, 2H), 5.04 (s, 2H), 3.77 (s, 3H), 3.67 (s, 3H). MS m/z (M+H): 477.

IonWorks® Experimental Procedure

Compounds were tested on human Na$_v$ 1.7 and Na$_v$ 1.5 channels stably expressed in HEK 293 cells. Sodium current measurements on IonWorks Quattro: An automated patch-clamp assay on the IonWorks Quattro platform (Molecular Devices) was used to measure state-dependent inhibition of human Na$_v$ 1.7 and Na$_v$ 1.5 channels. Cells were sealed on a planar substrate using the Population Patch Plate (PPC) technology. Electrical access was obtained using both nystatin and amphotericin. A double-pulse protocol was used for the determination of IC$_{50}$ values for inactivated state block. Na$_v$ 1.7 and Na$_v$ 1.5 expressing cells were voltage clamped at −100 mV and −110 mV, respectively. A depolarizing prepulse to −10 mV (Na$_v$ 1.7) or −30 mV (Na$_v$ 1.5) for 1000 ms followed by a 10 ms repolarization to ~100 mV (Nav1.7) or −110 mV (Na$_v$ 1.5) was given to generate fractional channel inactivation of ~50%, followed by a 10 ms test pulse to −10 mV (Na$_v$ 1.7) or −30 mV (Na$_v$ 1.5) to measure peak current in control conditions and after compound addition. The following recording solutions were used (mM). External: 150 NaCl, 2 CaCl$_2$, 5 KCl, 1 Mg Cl$_2$, 10 HEPES, 12 Dextrose; internal: 120 CsF, 30 CsCl, 10 EGTA, 5 HEPES, 5 NaF, 2 MgCl$_2$.

For all electrophysiology experiments, offline analysis was used to determine percent inhibition as a function of drug concentration. IC$_{50}$ values were determined by fitting to the Hill equation.

The various compounds in Examples 1 through 4 and Tables 1 through 3 exemplified above were assayed for activity and selectivity using the foregoing IonWorks® technique. The results are reported in the following paragraph in a format expressing the identification of the compound with reference Example and compound (e.g. Ex 1-9 is Example 1, compound 9) followed by the observed potency in nM and the ratio of Na$_v$1.7 potency: Na$_v$1.5 potency as described here. Thus, Ex1-9: 1.7=65/ratio=641 identifies compound Example 1, compound 9 as having 65 nM potency for the Nav 1.7 sodium ion channel (as measured by IonWorks®) and a ratio of 641 Na$_v$ 1.7: Na$_v$ 1.5 potency, determined by IonWorks® measurement. The following results are reported:

IonWorks® Data

Ex 1-3: 1.7=7/ratio>4700; Ex 1-8: 1.7=11/ratio>3000; Ex 1-9: 1.7=13/ratio>2540; Ex 1-11: 1.7=19/ratio>1740; Ex 1-12: 1.7=66/ratio>500; Ex 1-13: 1.7=16/ratio>2060; Ex 1-14: 1.7=38/ratio>870; Ex 1-16 Enantiomer A: 1.7=240/ratio=50; Ex 1-16 Enantiomer B: 1.7=130/ratio=185; Ex 1-17: 1.7=60/ratio>550; Ex 1-18: 1.7=7.9/ratio>4177; Ex 1-19: 1.7=10/ratio>3300; Ex 1-20: 1.7=56/ratio>590; Ex 1-21: 1.7=21/ratio>1570; Ex 1-22: 1.7=26/ratio>1270; Ex 1-23: 1.7=43/ratio>770; Ex 1-24: 1.7=17/ratio>1940. Ex 1-25: 1.7=21/ratio>1590; Ex 1-26: 1.7=30/ratio>1100; Ex 1-31: 1.7=37/ratio>890; Ex 1-32: 1.7=16/ratio>2060; Ex 1-34: 1.7=64/ratio>510; Ex 1-35: 1.7=190/ratio>170; Ex 1-36: 1.7=18/ratio>1830; Ex 1-37: 1.7=97/ratio>340; Ex 1-38: 1.7=44/ratio>750; Ex 1-39: 1.7=130/ratio>250; Ex 1-40: 1.7=110/ratio>300; Ex 1-41: 1.7=48/ratio>690; Ex 1-42: 1.7=80/ratio>410; Ex 1-43: 1.7=31/ratio>1060; Ex 1-44: 1.7=29/ratio>1140; Ex 1-45: 1.7=110/ratio>300; Ex 1-46: 1.7=30/ratio>1100; Ex 1-47: 1.7=22/ratio>1500; Ex 1-48: 1.7=23/ratio>1434; Ex 1-49: 1.7=33/ratio>1000; Ex 1-50: 1.7=46/ratio>717; Ex 1-51: 1.7=15/ratio>2200; Ex 1-52: 1.7=96/ratio>343; Ex 1-53: 1.7=79/ratio>418; Ex 2-4 Enantiomer A: 1.7=29/ratio>1140; Ex 2-4 Enantiomer B: 1.7=21/ratio>1570; Ex 3-4: 1.7=21/ratio>1570; Ex 6-7 Enantiomer B: 1.7=35/ratio>940; Ex 6-8: 1.7=39/ratio>850; Ex 6-9: 1.7=17/ratio=1530; Ex 7-04: 1.7=41/ratio>800; Ex 7-7: 1.7=80/ratio>410; Ex 7-12: 1.7=27/ratio>1200; Ex 7-13: 1.7=16/ratio>2060; Ex 8-2: 1.7=59/ratio=460; Ex 8-3: 1.7=13/ratio>2540; Ex 8-4: 1.7=32/ratio>1030; Ex 8-5: 1.7=40/ratio=425; Ex 8-6: 1.7=21/ratio>1570; Ex 8-7: 1.7=87/ratio>380; Ex 8-11: 1.7=14/ratio>2360; Ex 8-13: 1.7=16/ratio>2060; Ex 8-14: 1.7=14/ratio=2290; Ex 8-15: 1.7=66/ratio>500; Ex 8-16: 1.7=63/ratio>520; Ex 9-2: 1.7=29/ratio>1140; Ex 9-03: 1.7=19/ratio>1740; Ex 9-04: 1.7=25/ratio>1320; Ex 9-05: 1.7=79/ratio>420; Ex 9-06: 1.7=200/ratio>160; Ex 10-3: 1.7=78/ratio>423; Ex 11-11: 1.7=49/ratio>673; Ex 11-12: 1.7=49/ratio>673; Ex 16-02: 1.7=20/ratio>1650; Ex 16-03: 1.7=14/ratio 1930; Ex 16-07: 1.7=1.9/ratio>17400; Ex 16-10: 1.7=19/ratio>1740; Ex 16-11: 1.7=15/ratio>1530; Ex 16-23: 1.7=14/ratio>2357; Ex 16-31: 1.7=12/ratio>2750; Ex 16-37: 1.7=10/ratio>3300; Ex 16-38: 1.7=30/ratio>1100; Ex 16-39: 1.7=36/ratio>917; Ex 16-40: 1.7=29/ratio>1140; Ex 16-42: 1.7=44/ratio>750; Ex 16-43: 1.7=11/ratio>3000; Ex 16-44: 1.7=12/ratio>2750; Ex 16-45: 1.7=16/ratio>2060; Ex 16-46: 1.7=34/ratio>970; Ex 16-47: 1.7=74/ratio>460; Ex 16-51: 1.7=35/ratio>943; Ex 16-52: 1.7=31/ratio>1060; Ex 16-53: 1.7=42/ratio>786; Ex 16-54: 1.7=13/ratio>2540.

What is claimed is:

1. A compound of Formula A$^1$, or a pharmaceutically acceptable salt thereof:

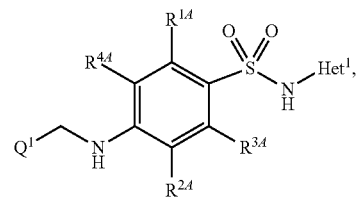

Formula A$^1$ wherein:
Het¹ is a five or six member heteroaryl moiety comprising up to 5 carbon atoms and one or more heteroatoms selected from N and S, which is optionally substituted on any ring carbon thereof by a halogen or methyl, which methyl may optionally be fluorine substituted, but is not selected to be a moiety of the following formula:

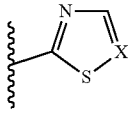

wherein X is —N= or —C(R$^{18A}$)=, wherein R$^{18A}$ is H, —Cl or —F;
R$^{1A}$ to R$^{4A}$ are independently —F, —Cl, —Br, —CN, —H, or a linear, branched or cyclic alkyl of up to 4 carbon atoms which may optionally be substituted on any carbon thereof with one or more fluorine, with the proviso that at least one of R$^{1A}$ to R$^{4A}$ is not —H and at least two of R$^{1A}$ to R$^{4A}$ are selected to be —H;
Q¹ is
(a) a moiety of the formula A¹-NH—X¹—, wherein:
  X¹ is:
    (i) alkyl of three or four carbon atoms which is optionally substituted on one or more carbon atoms thereof with halogen, benzyl, aryl, or a linear or branched alkyl of up to 4 carbon atoms; or
    (ii) a moiety of the formula:

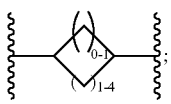

and
A¹ is:
  (i) R$^{1b}$—CHR$^{2b}$—, wherein
    R$^{2b}$ is: (ai)-aryl; (aii) —CH$_3$; (aiii) —H; or (aiv) halogen; and
    R$^{1b}$ is:
      (ai) a moiety of the formula:

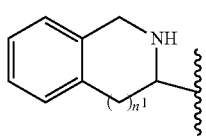

wherein n¹ is 0 or 1;
      (aii) a moiety of the formula:
R$^{3b}$NH—CH$_2$—(CHR$^{4b}$)$_{0-3}$—,
  wherein:
    (ai) R$^{3b}$ is —H; linear or branched alkyl of up to 4 carbon, or a moiety of the formula:

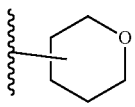

wherein the moiety is bonded via a carbon beta or gamma to the oxygen; and
    (aii) R$^{4b}$ is —H or —F;
  (aiii) a moiety of the formula:

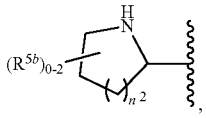

wherein:
  n² is 1 or 2; and
  R$^{5b}$ is up to two optional substituents bonded to one or more available ring carbon atoms which are independently for each occurrence: —F; —O-aryl; aryl; —CN; —O—CH$_3$; or

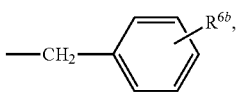

wherein R$^{6b}$ is an optional substituent bonded to an available ring carbon atom which, if present, is halogen or —O—CH$_3$; or
  (aiv) aryl, which is substituted on one ring carbon atom thereof with —CH$_2$NH$_2$;
(ii) a moiety of the formula:

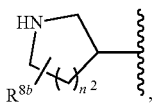

wherein R$^{8b}$ is —H or aryl;
(iii) a moiety of the formula: or

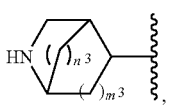

wherein n³ is 1 or 2 and m³ is 0 or 1;
(iv) adamantyl bonded to the nitrogen via any available carbon atom;
(b) a moiety of the formula:

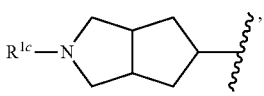

wherein R$^{1c}$ is a moiety of the formula:

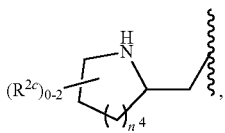

wherein:
n⁴ is 1 or 2; and
R²ᶜ is up to two optional substituents which are independently for each occurrence: —F; —O-aryl; aryl; —CN; —O—CH₃; or

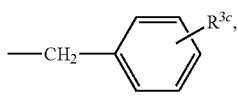

wherein R³ᶜ is an optional substituent bonded to an available ring carbon atom which, if present, is —O—CH₃; or
(c) a moiety of the formula A²-X²—, wherein:
X² is a linear or branched alkyl of three or four carbon atoms; and
A² is:
(i) a moiety of the formula:

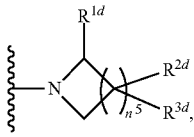

wherein:
n⁵=1-4;
R¹ᵈ is —H or —CH₂NH₂; and
R²ᵈ and R³ᵈ are selected as follows:
if R¹ᵈ is selected to be —CH₂—NH₂, then for all occurrences, R²ᵈ and R³ᵈ are —H; or if R¹ᵈ is —H, then at least one of R²ᵈ or R³ᵈ is: (ai) —CH₂—NH₂; (aii) —NH—CH₃; or (aiii) —NH₂, and the others of R²ᵈ and R³ᵈ are independently for each occurrence: (ai)—H; (ii) linear-, branched, or cyclic alkyl of up to 6 carbon atoms; or (aiii) aryl;
(ii) a moiety of the formula:

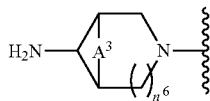

wherein:
n⁶ is 0 or 1;
if n⁶=0, then A³ is —(CH₂)₂—;
if n⁶=1, then A³ is a bond between the two ring carbon atoms;
(iii) a moiety of the formula:

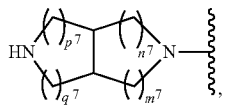

wherein:
p=1-3;
q⁷ and m⁷ are independently=0 or 1;
n⁷=1 or 2;

(iv) a moiety of the formula:

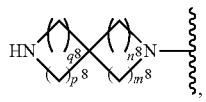

wherein:
m⁸ and q⁸ are independently 1, 2 or 3;
n⁸ and p⁸ are independently 0 or 1; and
m+n≤4; or
(v) a moiety of the formula:

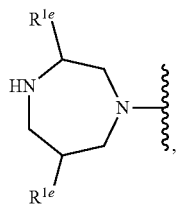

Wherein: (i) both R¹ᵉ are —H; or (ii) both R¹ᵉ taken together form a bridge of the formula —(CH₂)₁₋₃.
2. A compound according to claim 1 of the structure of Formula A², or a pharmaceutically acceptable salt thereof:

Formula A²

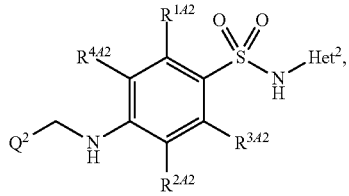

wherein:
Het² is a five or six member heteroaryl moiety comprising up to five carbon atoms and one or more heteroatoms selected from N and S, which is optionally substituted on any ring carbon thereof by a halogen or methyl, which methyl may optionally be fluorine substituted;
R¹ᴬ² to R⁴ᴬ² are independently —F, —Cl, —Br, —CN, —H, or a linear, branched or cyclic alkyl of up to 4 carbon atoms which may optionally be substituted on any carbon thereof with one or more fluorine, with the provisos that: (i) at least one of R¹ᴬ² to R⁴ᴬ² is not —H; (ii) at least two of R¹ᴬ to R⁴ᴬ are selected to be —H; and (iii) if R¹ᴬ² is selected to be —F, R²ᴬ² is not selected to be —F, —Cl or —Br;
Q₂ is
(a) a moiety of the formula A¹ᵇ-NH—X¹ᵇ—, wherein:
X¹ᵇ is:
(i) alkyl of three or four carbon atoms which is optionally substituted on one or more carbon atoms thereof with halogen, benzyl, aryl, or linear or branched alkyl of up to 4 carbon atoms; or
(ii) a moiety of the formula:

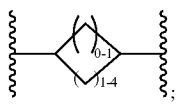

and

A$^{1b}$ is:
(i) R$^{1b}$—CHR$^{2b}$—, wherein
  R$^{2b}$ is: (ai) -aryl; (aii) —CH$_3$; (aiii) —H; or (aiv) halogen; and
  R$^{1b}$ is:
    (ai) a moiety of the formula:

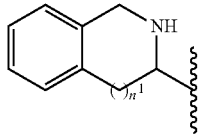

wherein n$^1$ is 0 or 1;
(aii) a moiety of the formula:
R$^{3b}$NH—CH$_2$—(CHR$^{4b}$)$_{0-3}$—,
wherein:
  (ai) R$^{3b}$ is —H; linear or branched alkyl of up to 4 carbon atoms, or a moiety of the formula:

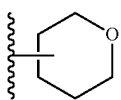

wherein the moiety is bonded via a carbon beta or gamma to the oxygen; and
  (aii) R$^{4b}$ is —H or —F;
(aiii) a moiety of the formula:

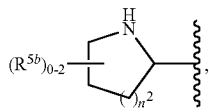

wherein:
  n$^2$ is 1 or 2; and
  R$^{5b}$ is up to two optional substituents bonded to one or more available ring carbon atoms which are independently for each occurrence: —F; —O-aryl; aryl; —CN; —O—CH$_3$; or

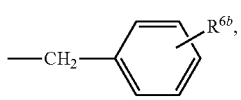

wherein R$^{6b}$ is an optional substituent bonded to an available ring carbon atom which, if present, is halogen or —O—CH$_3$; or
(aiv) aryl, which is substituted on one ring carbon atom thereof with —CH$_2$NH$_2$;
(ii) a moiety of the formula:

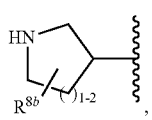

wherein R$^{8b}$ is —H or aryl;
(iii) a moiety of the formula: or

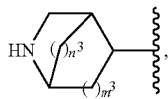

wherein n$^3$ is 1 or 2 and m$^3$ is 0 or 1; or
(iv) adamantyl bonded to the nitrogen via any available carbon atom;
(b) a moiety of the formula:

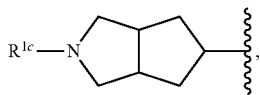

wherein R$^{1c}$ is a moiety of the formula:

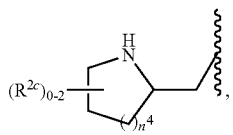

wherein:
  n$^4$ is 1 or 2; and
  R$^{2c}$ is up to two optional substituents which are independently for each occurrence: —F; —O-aryl; aryl; —CN; —O—CH$_3$; or

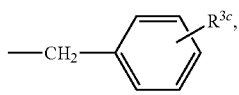

wherein R$^{3c}$ is an optional substituent bonded to an available ring carbon atom which, if present, is —O—CH$_3$; or
(c) a moiety of the formula A$^2$-X$^2$—, wherein:
X$^2$ is a linear or branched alkyl of three or four carbon atoms; and
A$^2$ is:
(i) a moiety of the formula:

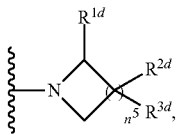

wherein:
  n=1-4;
  R$^{1d}$ is —H or —CH$_2$NH$_2$; and
  R$^{2d}$ and R$^{3d}$ are selected as follows:
    if R$^{1d}$ is selected to be —CH$_2$—NH$_2$, then for all occurrences, R$^{2d}$ and R$^{3d}$ are —H; or if R$^{1d}$ is —H, then at least one of R$^{2d}$ or R$^{3d}$ is: (ai) —CH$_2$—NH$_2$; (aii) —NH—CH$_3$; or (aiii) —NH$_2$, and the others of R$^{2d}$ and R$^{3d}$ are independently for each occurrence: (ai) —H; (ii) linear-, branched, or cyclic alkyl of up to 6 carbon atoms; or (aiii) aryl;

(ii) a moiety of the formula:

$$H_2N-\overset{A^3}{\underset{(\ )_{n^6}}{\diagup\!\!\!\diagdown}}N-\xi$$

wherein:
n$^6$ is 0 or 1;
if n$^6$=0, then A$^3$ is —(CH$_2$)$_2$—;
if n$^6$=1, then A$^3$ is a bond between the two ring carbon atoms;

(iii) a moiety of the formula:

$$HN\overset{(\ )_{p^7}\ (\ )_{n^7}}{\underset{(\ )_{q^7}\ (\ )_{m^7}}{\diagup\!\!\!\diagdown}}N-\xi,$$

wherein:
p=1-3;
q$^7$ and m$^7$ are independently=0 or 1;
n$^7$=1 or 2;

(iv) a moiety of the formula:

$$HN\overset{q^8\ n^8}{\underset{p^8\ m^8}{\diagup\!\!\!\diagdown}}N-\xi,$$

wherein:
m$^8$ and q$^8$ are independently 1, 2 or 3;
n$^8$ and p$^8$ are independently 0 or 1; and
m+n≤4; or (v) a moiety of the formula:

$$\begin{array}{c}R^{1e}\\HN\diagdown\!\!\!\diagup\!\!\!\diagdown N-\xi,\\R^{1e}\end{array}$$

wherein: (i) both R$^{1e}$ are —H; or (ii) both R$^{1e}$ taken together form a bridge of the formula —(CH$_2$)$_{1-3}$—.

3. A compound according to claim 1 of the structure of Formula A$^3$, or a pharmaceutically acceptable salt thereof:

$$\begin{array}{c}R^{1A3}\ \ \ O\\ \diagdown\!\!\!\diagup\!\!\!\diagdown\ \|\\ R^{4A3}-\diagdown\!\!\!\diagup-S-NH-Het^3,\\ \|\ \|\\ Q^3-CH_2-NH-\diagup-R^{3A3}\\ \ \ R^{2A3}\end{array}$$ Formula A$^3$ wherein:
Het$^3$ is a five or six member heteroaryl moiety comprising up to 5 carbon atoms and one or more heteroatoms selected from N and S, which is optionally substituted on any ring carbon thereof by a halogen or methyl, which methyl may optionally be fluorine substituted;
R$^{1A3}$ to R$^{4A3}$ are independently —F, —Cl, —Br, —CN, —H, or a linear, branched or cyclic alkyl of up to 4 carbon atoms which may optionally be substituted on any carbon thereof with one or more fluorine, with the proviso that at least one of R$^{1A3}$ to R$^{4A3}$ is not —H and at least two of R$^{1A3}$ to R$^{4A3}$ are selected to be —H;
Q$^3$ is
(a) a moiety of the formula A$^{1c}$-NH—X$^{1c}$—, wherein:
X$^{1c}$ is:
(i) alkyl of three or four carbon atoms which is optionally substituted on one or more carbon atoms thereof with halogen, benzyl, aryl, or linear or branched alkyl of up to 4 carbon atoms with the proviso that X$^{1c}$ is not —CH(Y)—CH$_2$—CH$_2$— wherein Y is —H or CH$_3$; or
(ii) a moiety of the formula:

$$\xi-\overset{\diagup\!\!\!\diagdown_{0-1}}{\underset{\diagdown\!\!\!\diagup_{1-4}}{}}-\xi;$$

and
A$^{1c}$ is:
(i) R$^{1b}$—CHR$^{2b}$—, wherein
R$^{2b}$ is: (ai) -aryl; (aii) —CH$_3$; (aiii) —H; or (aiv) halogen; and
R$^{1b}$ is:
(ai) a moiety of the formula:

$$\begin{array}{c}\diagup\!\!\!\diagdown\!\!\!\diagup CH_2\\ |\ \ |\ \ \ \ \ NH\\ \diagdown\!\!\!\diagup\!\!\!\diagdown_{n^1}\xi\end{array}$$

wherein n$^1$ is 0 or 1;
(aii) a moiety of the formula:

R$^{3b}$NH—CH$_2$—(CHR$^{4b}$)$_{0-3}$—, wherein:
(ai) R$^{3b}$ is —H; linear or branched alkyl of up to 4 carbon atoms, or a moiety of the formula:

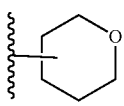

wherein the moiety is bonded via a carbon beta or gamma to the oxygen; and
(aii) $R^{4b}$ is —H or —F;
(aiii) a moiety of the formula:

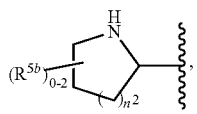

wherein:
$n^2$ is 1 or 2; and
$R^{5b}$ is up to two optional substituents bonded to one or more available ring carbon atoms which are independently for each occurrence: —F; —O-aryl; aryl; —CN; —O—$CH_3$; or

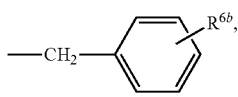

wherein $R^{6b}$ is an optional substituent bonded to an available ring carbon atom which, if present, is halogen or —O—$CH_3$; or
(aiv) aryl, which is substituted on one ring carbon atom thereof with —$CH_2NH_2$;
(ii) a moiety of the formula:

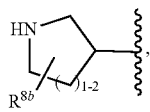

wherein $R^{8b}$ is —H or aryl;
(iii) a moiety of the formula:

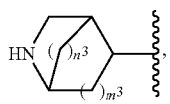

wherein $n^3$ is 1 or 2 and $m^3$ is 0 or 1; or
(iv) adamantyl bonded to the nitrogen via any available carbon atom;
(b) a moiety of the formula:

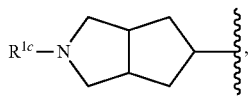

wherein $R^{1c}$ is a moiety of the formula:

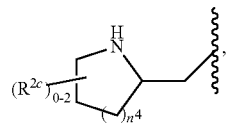

wherein:
$n^4$ is 1 or 2; and
$R^{2c}$ is up to two optional substituents which are independently for each occurrence: —F; —O-aryl; aryl; —CN; —O—$CH_3$; or

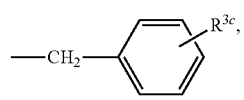

wherein $R^{3c}$ is an optional substituent bonded to an available ring carbon atom which, if present, is —O—$CH_3$; or
(c) a moiety of the formula $A^2$-$X^2$—, wherein:
$X^2$ is a linear or branched alkyl three or four carbon atoms; and
$A^2$ is:
(i) a moiety of the formula:

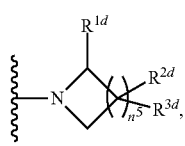

wherein:
$n^5$=1-4;
$R^{1d}$ is —H or —$CH_2NH_2$; and
$R^{2d}$ and $R^{3d}$ are selected as follows:
if $R^{1d}$ is selected to be —$CH_2$—$NH_2$, then for all occurrences, $R^{2d}$ and $R^{3d}$ are —H; or if $R^{1d}$ is —H, then at least one of $R^{2d}$ or $R^{3d}$ is: (ai) —$CH_2$—$NH_2$; (aii) —NH—$CH_3$; or (aiii) —$NH_2$, and the others of $R^{2d}$ and $R^{3d}$ are independently for each occurrence: (ai) —H; (ii) linear-, branched, or cyclic alkyl of up to 6 carbon atoms; or (aiii) aryl;
(ii) a moiety of the formula:

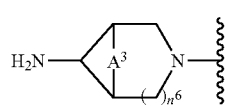

wherein:
$n^6$ is 0 or 1;
if $n^6$=0, then $A^3$ is —$(CH_2)_2$—;
if $n^6$=1, then $A^3$ is a bond between the two ring carbon atoms;

(iii) a moiety of the formula:

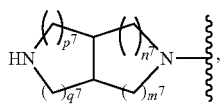

wherein:
p$^7$=1-3;
q$^7$ and m$^7$ are independently=0 or 1;
n$^7$=1 or 2;
(iv) a moiety of the formula:

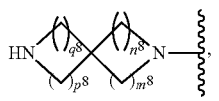

wherein:
m$^8$ and q$^8$ are independently 1, 2 or 3;
n$^8$ and p$^8$ are independently 0 or 1; and
m$^8$+n$^8$≤4; or
(v) a moiety of the formula:

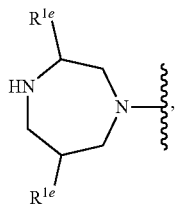

wherein: (i) both R$^{1e}$ are —H; or (ii) both R$^{1e}$ taken together form a bridge of the formula —(CH$_2$)$_{1-3}$—.

4. A compound of claim 1, or a salt thereof, wherein: (i) R$^{1A}$ is —F, R$^{3A}$ and R$^{4A}$ are —H, and R$^{2A}$ is —F, —Cl, —Br, —CN, —CH$_3$, or —CF$_3$; (ii) R$^{1A2}$, R$^{2A2}$ and R$^{3A2}$ are —H, and R$^{4A2}$ is —Cl; (iii) R$^{1A}$, R$^{3A}$ and R$^{4A}$ are —H, and R$^{2A}$ is —CF$_3$; or (iv) R$^{1A}$ and R$^{2A}$ are —H, and R$^{3A}$ and R$^{4A}$ are —F.

5. A compound of claim 2, or a salt thereof, wherein: (i) R$^{1A2}$ is —F, R$^{3A2}$ and R$^{4A2}$ are —H, and R$^{2A2}$ is —CN, —CH$_3$, or —CF$_3$; (ii) R$^{1A2}$, R$^{2A2}$ and R$^{3A2}$ are —H, and R$^{4A2}$ is —Cl; (iii) R$^{1A2}$, R$^{3A2}$ and R$^{4A2}$ are —H, and R$^{2A2}$ is —CF$_3$; or (iv) R$^{1A2}$ and R$^{2A2}$ are —H, and R$^{3A2}$ and R$^{4A2}$ are —F.

6. A compound of claim 3, or a salt thereof, wherein: (i) R$^{1A3}$ is —F, R$^{3A3}$ and R$^{4A3}$ are —H, and R$^{2A3}$ is —F, —Cl, —Br, —CN, —CH$_3$, or —CF$_3$; (ii) R$^{1A3}$, R$^{2A3}$ and R$^{4A3}$ are —H, and R$^{4A3}$ is —Cl; (iii) R$^{1A3}$, R$^{3A3}$ and R$^{4A3}$ are —H, and R$^{2A3}$ is —CF$_3$; or (iv) R$^{1A3}$ and R$^{2A3}$ are —H, and R$^{3A3}$ and R$^{4A3}$ are —F.

7. A compound of claim 1, or a salt of any thereof, wherein X$^1$ is:

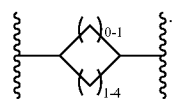

8. A compound of claim 1, or a salt of any thereof, wherein said Het$^1$ is, independently, a heterocycle of the formula:

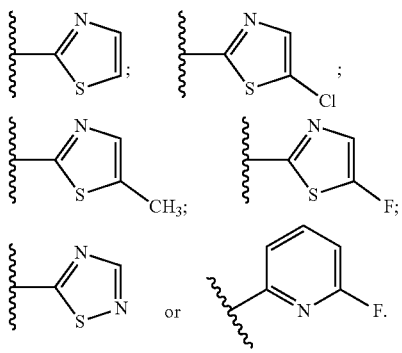

9. A compound according to claim 1, or a salt thereof, having the formula:

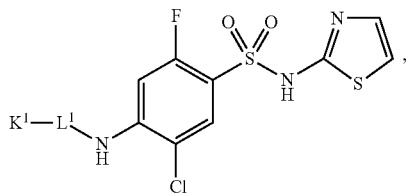

wherein:
K$^1$ is the formula:

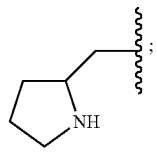 [SMILES: *CC1CCCN1]

and
L$^1$ is:

(i)

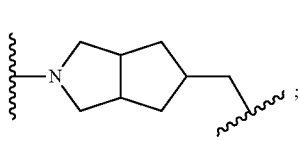

(ii)

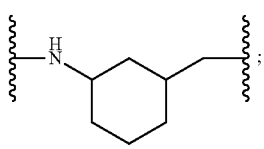

(iii)

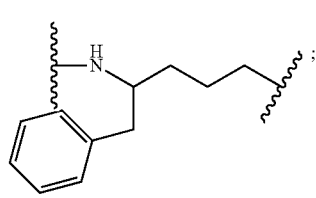

-continued

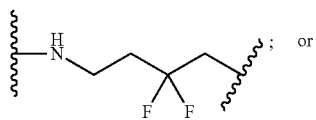  or

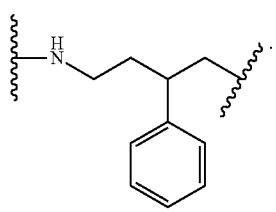

10. A compound or a salt thereof, having the formula:

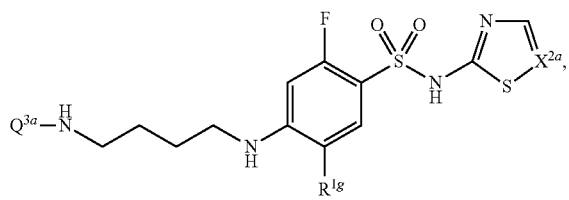

wherein $X^{2a}$ is —N=, —CH=, or —CF=;

$R^{1g}$ is —Cl or —Br; and $Q^{2a}$ is:

(i) a heterocycle of the formula:

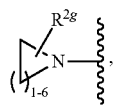

where $R^{2g}$ is optionally bonded to any carbon at any available position and is: (ai) —CH$_2$—NH$_2$; (aii) —NH—CH$_3$; (aiii) aryl; or (aiv) —NH$_2$;

(ii) a heterocycle of the formula:

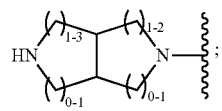

(iii) a heterocycle of the formula:

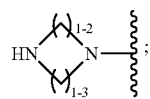

(iv) a heterocycle of the formula:

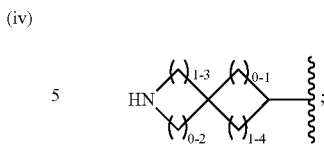

or (v) a heterocycle of the formula:

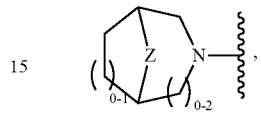

wherein Z is: —NH—; CR$^{3g}$H—, wherein R$^{3g}$ is —H or —NH$_2$; or a bond.

11. A compound, or a salt thereof, having the formula:

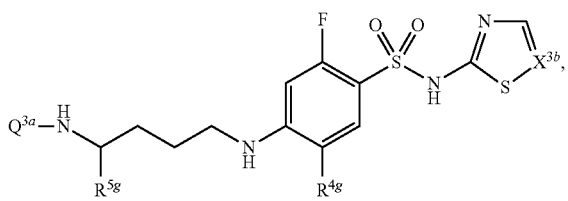

wherein:

$R^{4g}$ is —Cl or —Br;

$R^{5g}$ is —H or —CH$_3$;

$X^{3b}$ is:

—N=; or

—C(R$^{6g}$)=, wherein R$^{6g}$ is: (i) —H; (ii) —CH$_3$; (iii) —Cl; or (iv) —F; and $Q^{3a}$ is:

(a) a bridged heterocycle comprising a central ring of at least one nitrogen atom and up to 7 carbon atoms, and wherein a linear or branched alkyl of up to 3 carbon atoms forms a "bridge" between any two non-adjacent ring carbon atoms, and wherein said heterocycle is bonded to the nitrogen via any carbon atom therein which is not adjacent to a heteroatom therein;

(b) a heterocycle comprising at least one nitrogen atom and up to 6 carbon atoms which is substituted on at least one carbon thereof with aryl, and which is bonded via a carbon atom that is not adjacent to a ring heteroatom;

(c) a linear, branched or cyclic alkyl of up to 8 carbon atoms which is substituted on at least one carbon atom thereof with: (ai) —F; (aii) aryl; (aiii) tetrahydropyranyl; or (aiv) benzyl, and on another carbon atom thereof is substituted with (R$^{7g}$)$_2$N—, wherein R$^{7g}$ is independently —H, or lower alkyl;

(d) a linear or branched alkyl of up to 5 carbon atoms which is substituted on at least one carbon thereof with:

(i) a heterocycle bonded via any available ring carbon atom, said heterocycle comprising a ring of up to 6 carbon atoms and at least one nitrogen atom which is substituted on at least one ring carbon atom with:

(ai) aryl which is optionally substituted with a linear-, branched- or cyclic-alkoxy of up to 6 carbon atoms;

(aii) —F;
(aiii) —O-aryl;
(aiv) —O-alkyl;
(av) —CN; or
(avi) benzyl which is optionally substituted on any available ring carbon with a linear-, branched- or cyclic-alkoxy of up to 6 carbon atoms;
(ii) $R^{8g}$—NH—, wherein $R^{8g}$ is:
(ai) aryl;
(aii) benzyl;
(aiii) adamantyl; or
(aiv) tetrahydropyran; or
(e) $R^{9g}$—NH—$(C(R^{10g})_2)_{2-4}^-$, wherein:
at least one $R^{10g}$ is —F, aryl, or —CN and the others of $R^{10g}$ are independently —H, —F, aryl, benzyl, or lower alkyl; and
$R^{9g}$ is:
(ai) —H; or
(aii) lower alkyl optionally substituted on one or more carbon atoms thereof with —F.

12. The compound of claim 11 wherein $Q^{3a}$ is a bridged heterocycle of the formula:

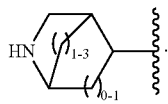

13. A compound which is:
4-[(4-{[2-(benzylamino)ethyl]amino}butyl)amino]-5-chloro-2-fluoro-N-1,3-thiazol-2-ylbenzenesulfonamide;
5-chloro-2-fluoro-4-[(4-{[(3R,5S)-5-phenylpyrrolidin-3-yl]amino}butyl)amino]-N-1,3-thiazol-2-ylbenzenesulfonamide;
5-chloro-2-fluoro-4-({4-[(1,2,3,4-tetrahydroisoquinolin-3-ylmethyl)amino]butyl}amino)-N-1,3-thiazol-2-ylbenzenesulfonamide;
4-({4-[(3S)-3-aminopyrrolidin-1-yl]butyl}amino)-5-chloro-2-fluoro-N-1,3-thiazol-2-ylbenzenesulfonamide;
5-chloro-4-{[4-(1,7-diazaspiro[4.4]non-1-yl)butyl]amino}-2-fluoro-N-1,3-thiazol-2-ylbenzenesulfonamide;
5-chloro-2-fluoro-4-{[4-(octahydro-6H-pyrrolo[3,4-b]pyridin-6-yl)butyl]amino}-N-1,3-thiazol-2-ylbenzenesulfonamide;
5-chloro-4-{[4-(1,8-diazaspiro[4.5]dec-8-yl)butyl]amino}-2-fluoro-N-1,3-thiazol-2-ylbenzenesulfonamide;
(R)-5-chloro-2-fluoro-4-{[4-({[2-(4-methoxybenzyl)pyrrolidin-2-yl]methyl}amino) butyl]amino}-N-1,3-thiazol-2-ylbenzenesulfonamide;
(S)-5-chloro-2-fluoro-4-{[4-({[2-(4-methoxybenzyl)pyrrolidin-2-yl]methyl}amino) butyl]amino}-N-1,3-thiazol-2-ylbenzenesulfonamide;
5-chloro-2-fluoro-4-{[4-({[2-(4-methoxybenzyl)pyrrolidin-2-yl]methyl}amino) butyl]amino}-N-1,3-thiazol-2-ylbenzenesulfonamide;
4-({4-[(1R,4R,7S)-2-azabicyclo[2.2.1]hept-7-ylamino]butyl}amino)-5-chloro-2-fluoro-N-1,3-thiazol-2-ylbenzenesulfonamide;
(R) 5-chloro-2-fluoro-4-({4-[(1,2,3,4-tetrahydroisoquinolin-3-ylmethyl)amino]butyl}amino)-N-1,3-thiazol-2-ylbenzenesulfonamide;
(S) 5-chloro-2-fluoro-4-({4-[(1,2,3,4-tetrahydroisoquinolin-3-ylmethyl)amino]butyl}amino)-N-1,3-thiazol-2-ylbenzenesulfonamide;
5-chloro-2-fluoro-4-({4-[(1,2,3,4-tetrahydroisoquinolin-3-ylmethyl)amino]butyl}amino)-N-1,3-thiazol-2-ylbenzenesulfonamide;
4-({4-[(1R,4R,7S)-7-amino-2-azabicyclo[2.2.1]hept-2-yl]butyl}amino)-5-chloro-2-fluoro-N-1,3-thiazol-2-ylbenzenesulfonamide;
5-chloro-2-fluoro-4-({4-[(3aS,7aR)-octahydro-1H-pyrrolo[2,3-c]pyridin-1-yl]butyl}amino)-N-1,3-thiazol-2-ylbenzenesulfonamide;
5-chloro-2-fluoro-4-({4-[(3aR,6aS)-hexahydropyrrolo[3,4-c]pyrrol-2(1H)-yl]butyl}amino)-N-1,3-thiazol-2-ylbenzenesulfonamide;
5-chloro-2-fluoro-4-({4-[(3aR,7aR)-octahydro-2H-pyrrolo[3,4-c]pyridin-2-yl]butyl}amino) -N-1,3-thiazol-2-ylbenzenesulfonamide;
4-({4-[(1S,4S)-2-azabicyclo[2.2.1]hept-5-ylamino]butyl}amino)-5-chloro-2-fluoro-N-1,3-thiazol-2-ylbenzenesulfonamide;
4-({4-[(1S,4S,7R)-2-azabicyclo[2.2.1]hept-7-ylamino]butyl}amino)-5-chloro-2-fluoro-N-1,3-thiazol-2-ylbenzenesulfonamide;
5-chloro-2-fluoro-4-[(4-{[(1R)-1-methyl-2-(tetrahydro-2H-pyran-4-ylamino)ethyl]amino}butyl)amino]-N-1,3-thiazol-2-ylbenzenesulfonamide;
5-chloro-2-fluoro-4-({4-[(5-phenylpiperidin-3-yl)amino]butyl}amino)-N-1,3-thiazol-2-ylbenzenesulfonamide;
4-({4-[(2-amino-1-phenylethyl)amino]butyl}amino)-5-chloro-2-fluoro-N-1,3-thiazol-2-ylbenzenesulfonamide;
5-chloro-2-fluoro-4-{[4-({[2-(3-methoxybenzyl)pyrrolidin-2-yl]methyl}amino)butyl]amino}-N-1,3-thiazol-2-ylbenzenesulfonamide;
4-({4-[(3R)-3-aminopiperidin-1-yl]butyl}amino)-5-chloro-2-fluoro-N-1,3-thiazol-2-ylbenzenesulfonamide;
4-({4-[(3R)-3-aminopyrrolidin-1-yl]butyl}amino)-5-chloro-2-fluoro-N-1,3-thiazol-2-ylbenzenesulfonamide;
4-({4-[(3S)-3-aminopiperidin-1-yl]butyl}amino)-5-chloro-2-fluoro-N-1,3-thiazol-2-ylbenzenesulfonamide;
5-chloro-4-{[4-(2,7-diazaspiro[4.4]non-2-yl)butyl]amino}-2-fluoro-N-1,3-thiazol-2-ylbenzenesulfonamide;
5-chloro-4-{[4-(1,7-diazaspiro[4.5]dec-7-yl)butyl]amino}-2-fluoro-N-1,3-thiazol-2-ylbenzenesulfonamide;
5-chloro-4-{[4-(1,6-diazaspiro[3.5]non-1-yl)butyl]amino}-2-fluoro-N-1,3-thiazol-2-ylbenzenesulfonamide;
4-({4-[(2R)-2-(aminomethyl)pyrrolidin-1-yl]butyl}amino)-5-chloro-2-fluoro-N-1,3-thiazol-2-ylbenzenesulfonamide;
4-{[4-(6-amino-3-azabicyclo[3.1.0]hex-3-yl)butyl]amino}-5-chloro-2-fluoro-N-1,3-thiazol-2-ylbenzenesulfonamide;
4-{[4-(4-aminoazepan-1-yl)butyl]amino}-5-chloro-2-fluoro-N-1,3-thiazol-2-ylbenzenesulfonamide;
4-{[4-(3-aminoazetidin-1-yl)butyl]amino}-5-chloro-2-fluoro-N-1,3-thiazol-2-ylbenzenesulfonamide;
4-({4-[4-(aminomethyl)-4-phenylpiperidin-1-yl]butyl}amino)-5-chloro-2-fluoro-N-1,3-thiazol-2-ylbenzenesulfonamide;

4-({4-[3-(aminomethyl)piperidin-1-yl]butyl}amino)-5-chloro-2-fluoro-N-1,3-thiazol-2-ylbenzenesulfonamide;
4-({4-[3-(aminomethyl)pyrrolidin-1-yl]butyl}amino)-5-chloro-2-fluoro-N-1,3-thiazol-2-ylbenzenesulfonamide;
5-chloro-2-fluoro-4-{[4-(octahydro-5H-pyrrolo[3,4-c]pyridin-5-yl)butyl]amino}-N-1,3-thiazol-2-ylbenzenesulfonamide;
4-{[4-(4-aminopiperidin-1-yl)butyl]amino}-5-chloro-2-fluoro-N-1,3-thiazol-2-ylbenzenesulfonamide;
4-({4-[3-(aminomethyl)-3-phenylpyrrolidin-1-yl]butyl}amino)-5-chloro-2-fluoro-N-1,3-thiazol-2-ylbenzenesulfonamide;
4-({4-[3-(aminomethyl)azetidin-1-yl]butyl}amino)-5-chloro-2-fluoro-N-1,3-thiazol-2-ylbenzenesulfonamide;
5-chloro-4-{[4-(3,9-diazabicyclo[4.2.1]non-3-yl)butyl]amino}-2-fluoro-N-1,3-thiazol-2-ylbenzenesulfonamide;
5-chloro-4-{[4-(1,4-diazepan-1-yl)butyl]amino}-2-fluoro-N-1,3-thiazol-2-ylbenzenesulfonamide;
(R)-5-chloro-2-fluoro-4-((4-((isoindolin-1-ylmethyl)amino)butyl)amino)-N-(thiazol-2-yl)benzenesulfonamide;
(S)-5-chloro-2-fluoro-4-((4-((isoindolin-1-ylmethyl)amino)butyl)amino)-N-(thiazol-2-yl)benzenesulfonamide;
5-chloro-2-fluoro-4-((4-((isoindolin-1-ylmethyl)amino)butyl)amino)-N-(thiazol-2-yl)benzenesulfonamide;
4-((4-((2-(aminomethyl)benzyl)amino)butyl)amino)-5-chloro-2-fluoro-N-(thiazol-2-yl)benzenesulfonamide;
5-chloro-2-fluoro-4-(((1S,3R)-3-(((S)-pyrrolidin-2-ylmethyl)amino)-cyclohexyl)methyl)amino)-N-(thiazol-2-yl)benzenesulfonamide;
5-chloro-2-fluoro-4-(((1R,3S)-3-(((S)-pyrrolidin-2-ylmethyl)amino)-cyclohexyl)methyl)amino)-N-(thiazol-2-yl)benzenesulfonamide;
5-chloro-2-fluoro-4-[({(3aR,5R,6aS)-2-[(2S)-pyrrolidin-2-ylmethyl]octahydro-cyclopenta[c]pyrrol-5-yl}methyl)amino]-N-1,3-thiazol-2-ylbenzenesulfonamide;
5-chloro-2-fluoro-4-[(5-phenyl-4-{[(2S)-pyrrolidin-2-ylmethyl]amino}pentyl)amino]-N-1,3-thiazol-2-ylbenzenesulfonamide;
4-[(4-1{[(2S)-pyrrolidin-2-ylmethyl]amino}butyl)amino]-N-1,3-thiazol-2-yl-3-(trifluoromethyl)benzenesulfonamide;
2,5-difluoro-4-[(4-{[(2S)-pyrrolidin-2-ylmethyl]amino}butyl)amino]-N-1,2,4-thiadiazol-5-ylbenzenesulfonamide;
3-chloro-4-[(4-{[(2S)-pyrrolidin-2-ylmethyl]amino}butyl)amino]-N-1,3-thiazol-2-ylbenzenesulfonamide;
3-chloro-N-(5-fluoro-1,3-thiazol-2-yl)-4-[(4-{[(2S)-pyrrolidin-2-ylmethyl]amino}butyl)amino]benzenesulfonamide;
(S)-5-chloro-4-((4-(((4,4-difluoropyrrolidin-2-yl)methyl)amino)butyl)amino)-2-fluoro-N-(thiazol-2-yl)benzenesulfonamide;
5-chloro-2-fluoro-4-{[4-({[(2S,5R)-5-phenylpyrrolidin-2-yl]methyl}amino)butyl]amino}-N-1,3-thiazol-2-ylbenzenesulfonamide;
5-chloro-2-fluoro-4-{[4-({[(2S,4S)-4-phenylpyrrolidin-2-yl]methyl}amino)butyl]amino}-N-1,3-thiazol-2-ylbenzenesulfonamide;
5-chloro-2-fluoro-4-{[4-({[(2S,4S)-4-phenoxypyrrolidin-2-yl]methyl}amino)butyl]amino}-N-1,3-thiazol-2-ylbenzenesulfonamide;
5-chloro-2-fluoro-4-{[4-({[(2S,3R)-3-phenylpyrrolidin-2-yl]methyl}amino)butyl]amino}-N-1,3-thiazol-2-ylbenzenesulfonamide;
5-chloro-4-{[4-({[(2S,4R)-4-cyanopyrrolidin-2-yl]methyl}amino)butyl]amino}-2-fluoro-N-1,3-thiazol-2-ylbenzenesulfonamide;
5-chloro-2-fluoro-4-{[4-({[(2R,4S)-4-phenylpyrrolidin-2-yl]methyl}amino)butyl]amino}-N-1,3-thiazol-2-ylbenzenesulfonamide;
5-chloro-2-fluoro-4-{[4-({[(2S,4R)-4-phenylpyrrolidin-2-yl]methyl}amino)butyl]amino}-N-1,3-thiazol-2-ylbenzenesulfonamide;
5-chloro-2-fluoro-4-[(4-{[(5-phenylpiperidin-2-yl)methyl]amino}butyl)amino]-N-1,3-thiazol-2-ylbenzenesulfonamide;
5-chloro-4-{[4-({[(2R)-4,4-difluoropyrrolidin-2-yl]methyl}amino)butyl]amino}-2-fluoro-N-1,3-thiazol-2-ylbenzenesulfonamide;
5-chloro-2-fluoro-4-{[4-({[(2S,4R)-4-methoxypyrrolidin-2-yl]methyl}amino)butyl]amino}-N-1,3-thiazol-2-ylbenzenesulfonamide;
(S)-5-chloro-2-fluoro-N-(6-fluoropyridin-2-yl)-4-((5-((pyrrolidin-2-ylmethyl)amino)pentyl)-amino)benzenesulfonamide;
5-chloro-2-fluoro-4-({5-[(piperidin-2-ylmethyl)-amino]pentyl}amino)-N-1,3-thiazol-2-yl-benzenesulfonamide;
5-chloro-2-fluoro-4-({5-[(piperidin-3-ylmethyl)-amino]pentyl}amino)-N-1,3-thiazol-2-yl-benzenesulfonamide;
4-[(5-{[(2R)-2-aminopropyl]-amino}pentyl)amino]-5-chloro-2-fluoro-N-1,3-thiazol-2-yl-benzenesulfonamide;
4-({5-[(azetidin-2-ylmethyl)amino]-pentyl}amino)-5-chloro-2-fluoro-N-1,3-thiazol-2-yl-benzenesulfonamide;
5-chloro-2-fluoro-4-((2-phenyl-4-(((S)-pyrrolidin-2-ylmethyl)amino)butyl)amino)-N-(thiazol-2-yl)benzenesulfonamide;
5-chloro-4-[(2,2-difluoro-4-{[(2R)-pyrrolidin-2-ylmethyl]amino}butyl)amino]-2-fluoro-N-1,3-thiazol-2-ylbenzenesulfonamide;
5-chloro-4-[(2,2-difluoro-4-{[(2S)-pyrrolidin-2-ylmethyl]amino}butyl)amino]-2-fluoro-N-1,3-thiazol-2-ylbenzenesulfonamide,
4-({4-[(2R)-2-(aminomethyl)azetidin-1-yl]butyl}amino)-5-chloro-2-fluoro-N-1,2,4-thiadiazol-5-ylbenzenesulfonamide;
5-chloro-2-fluoro-4-({4-[(3R)-3-(methylamino)pyrrolidin-1-yl]butyl}-amino)-N-1,2,4-thiadiazol-5-ylbenzene-sulfonamide;
5-chloro-2-fluoro-N-(5-fluoro-1,3-thiazol-2-yl)-4-[(4-{[2-(tricyclo[3.3.1.1~3,7~]dec-2-ylamino)-ethyl]amino}butyl)amino]benzene-sulfonamide;
4-({4-[(2R)-2-(aminomethyl)azetidin-1-yl]butyl}amino)-5-chloro-2-fluoro-N-(5-fluoro-1,3-thiazol-2-yl)benzene-sulfonamide;
4-({4-[(2S)-2-(aminomethyl)azetidin-1-yl]butyl}amino)-5-chloro-2-fluoro-N-(5-fluoro-1,3-thiazol-2-yl)benzene-sulfonamide;
5-chloro-2-fluoro-N-(5-fluoro-1,3-thiazol-2-yl)-4-({4-[(4aR,7aR)-octahydro-6H-pyrrolo[3,4-b]pyridin-6-yl]butyl}amino)benzene-sulfonamide;

5-chloro-2-fluoro-4-({4-[(4aR,7aR)-octahydro-6H-pyrrolo[3,4-b]pyridin-6-yl]-butyl}amino)-N-1,2,4-thiadiazol-5-ylbenzene-sulfonamide;

4-((4-(3-(aminomethyl)azetidin-1-yl)butyl)amino)-5-bromo-2-fluoro-N-(1,2,4-thiadiazol-5-yl)benzene-sulfonamide;

4-{[4-(3-aminoazetidin-1-yl)-butyl]amino}-5-chloro-2-fluoro-N-1,2,4-thiadiazol-5-yl-benzenesulfonamide;

5-cyano-2-fluoro-4-({4-[(3R)-pyrrolidin-3-ylamino]-butyl}amino)-N-1,3-thiazol-2-yl-benzenesulfonamide;

5-cyano-2-fluoro-N-(5-fluoro-1,3-thiazol-2-yl)-4-({4-[(3R)-pyrrolidin-3-yl-amino]butyl}amino)benzene-sulfonamide;

4-({4-[(1S,4R)-2-azabicyclo[2.2.1]hept-6-yl-amino]butyl}amino)-5-chloro-2-fluoro-N-1,3-thiazol-2-yl-benzene-sulfonamide;

2-fluoro-N-(5-fluoro-1,3-thiazol-2-yl)-5-methyl-4-({4-[(3R)-pyrrolidin-3-ylamino]-butyl}amino)benzene-sulfonamide;

5-bromo-2-fluoro-N-(5-fluoro-1,3-thiazol-2-yl)-4-({4-[(4aR,7aR)-octahydro-6H-pyrrolo[3,4-b]pyridin-6-yl]butyl}amino)benzene-sulfonamide;

5-cyano-2-fluoro-4-({4-[(3R)-pyrrolidin-3-yl-amino]butyl}amino)-N-1,2,4-thiadiazol-5-ylbenzene-sulfonamide;

4-({4-[(3-amino-2-fluoro-propyl)amino]butyl}amino)-5-chloro-2-fluoro-N-(5-fluoro-1,3-thiazol-2-yl)-benzenesulfonamide;

2,5-difluoro-4-[(4-{[2-(methylamino)ethyl]amino}-butyl)amino]-N-1,2,4-thiadiazol-5-ylbenzene-sulfonamide;

5-chloro-2-fluoro-4-[(4-{[2-(methylamino)ethyl]amino}-butyl)amino]-N-(4-methyl-1,3-thiazol-2-yl)benzene-sulfonamide;

(R) 4-({4-[2-(aminomethyl)-azetidin-1-yl]butyl}amino)-5-chloro-2-fluoro-N-1,3-thiazol-2-ylbenzene-sulfonamide;

(S) 4-({4-[2-(aminomethyl)-azetidin-1-yl]butyl}amino)-5-chloro-2-fluoro-N-1,3-thiazol-2-ylbenzene-sulfonamide;

4-({4-[2-(aminomethyl)-azetidin-1-yl]butyl}amino)-5-chloro-2-fluoro-N-1,3-thiazol-2-ylbenzene-sulfonamide; or 5-chloro-2-fluoro-N-(5-fluoro-1,3-thiazol-2-yl)-4-({4-[(3R)-3-(methylamino)-pyrrolidin-1-yl]butyl}-amino)-benzenesulfonamide, or a pharmaceutically acceptable salt of any thereof.

14. A formulation comprising at least one compound of claim 1 or a pharmaceutically acceptable salt thereof, and at least one pharmaceutically acceptable excipient.

15. A pharmaceutical formulation of claim 14 comprising additionally an effective amount of at least one pharmaceutically active ingredient which is: (i) an opiate agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP), and a pharmaceutically acceptable carrier.

16. The formulation of claim 14 which is adapted for IV infusion or IV administration.

17. A method of treating an inflammatory or neuropathic pain disorder, cough, or acute itch or chronic itch disorder comprising administering to a patient in need thereof a therapeutically effective amount of a formulation of claim 14.

18. A method of treating a neuropathic pain disorder comprising administering to a patient in need thereof a therapeutically effective amount of a formulation of claim 14.

19. A method of treating acute pain comprising administering to a patient in need thereof a therapeutically effective amount of a formulation of claim 16.

\* \* \* \* \*